US011142769B2

(12) United States Patent
Aoki et al.

(10) Patent No.: US 11,142,769 B2
(45) Date of Patent: Oct. 12, 2021

(54) SINGLE-STRANDED NUCLEIC ACID MOLECULE HAVING DELIVERY FUNCTION AND GENE EXPRESSION REGULATING ABILITY

(71) Applicant: BONAC CORPORATION, Kurume (JP)

(72) Inventors: Eriko Aoki, Kurume (JP); Shiori Kato, Kurume (JP); Tadaaki Ohgi, Kurume (JP)

(73) Assignee: BONAC CORPORATION, Kurume (JP)

( * ) Notice: Subject to any disclaimer, the term of this patent is extended or adjusted under 35 U.S.C. 154(b) by 0 days.

(21) Appl. No.: 15/562,231

(22) PCT Filed: Mar. 26, 2016

(86) PCT No.: PCT/JP2016/059779
§ 371 (c)(1),
(2) Date: Sep. 27, 2017

(87) PCT Pub. No.: WO2016/158809
PCT Pub. Date: Oct. 6, 2016

(65) Prior Publication Data
US 2018/0119151 A1 May 3, 2018

(30) Foreign Application Priority Data
Mar. 27, 2015 (JP) .............................. JP2015-065770

(51) Int. Cl.
| C12N 15/11 | (2006.01) |
| C12N 15/113 | (2010.01) |
| A61K 31/7125 | (2006.01) |
| A61K 48/00 | (2006.01) |
| A61P 29/00 | (2006.01) |

(52) U.S. Cl.
CPC ...... C12N 15/1136 (2013.01); A61K 31/7125 (2013.01); A61K 48/00 (2013.01); A61P 29/00 (2018.01); C12N 15/113 (2013.01); C12N 2310/14 (2013.01); C12N 2310/141 (2013.01); C12N 2310/351 (2013.01); C12N 2310/3513 (2013.01); C12N 2310/3515 (2013.01); C12N 2310/531 (2013.01)

(58) Field of Classification Search
CPC .............. C12N 15/113; C12N 2310/14; C12N 2310/141; C12N 2310/351
See application file for complete search history.

(56) References Cited

U.S. PATENT DOCUMENTS

| 3,687,808 | A | 8/1972 | Merigan, Jr. et al. |
| 4,550,163 | A | 10/1985 | Voss et al. |
| 6,905,827 | B2 | 6/2005 | Wohlgemuth et al. |
| 7,579,148 | B2 | 8/2009 | Wohlgemuth et al. |
| 7,595,301 | B2 | 9/2009 | Kunugiza et al. |
| 7,604,936 | B2 | 10/2009 | Wohlgemuth et al. |
| 7,655,768 | B2 | 2/2010 | Ohgi et al. |
| 7,771,950 | B2 | 8/2010 | Wohlgemuth et al. |
| 8,110,364 | B2 | 2/2012 | Wohlgemuth et al. |
| 8,691,782 | B2 | 4/2014 | Ohgi et al. |
| 8,785,121 | B2 | 7/2014 | Ohgi et al. |
| 8,933,046 | B2 | 1/2015 | Machuy et al. |
| 9,206,422 | B2 | 12/2015 | Ohgi et al. |
| 9,528,111 | B2 | 12/2016 | Ohgi et al. |
| 9,663,784 | B2 * | 5/2017 | Ohgi ..................... A61K 48/00 |
| 10,238,752 | B2 | 3/2019 | Ohgi et al. |
| 2002/0042059 | A1 | 4/2002 | Makarov et al. |
| 2002/0156261 | A1 | 10/2002 | Malvy et al. |
| 2003/0059789 | A1 | 3/2003 | Efimov et al. |
| 2003/0077608 | A1 | 4/2003 | Coull et al. |
| 2003/0232355 | A1 | 12/2003 | Norden et al. |
| 2004/0009479 | A1 | 1/2004 | Wohlgemuth et al. |
| 2004/0058886 | A1 | 3/2004 | Scaringe |
| 2004/0110296 | A1 | 6/2004 | Vargeese et al. |
| 2004/0241855 | A1 | 12/2004 | Cullis et al. |
| 2005/0053979 | A1 | 3/2005 | Livak et al. |

(Continued)

FOREIGN PATENT DOCUMENTS

| CN | 1860228 A | 11/2006 |
| CN | 101076592 A | 11/2007 |

(Continued)

OTHER PUBLICATIONS

Fire et al., "Potent and specific genetic interference by double-stranded RNA in *Caenorhabditis elegans*," Nature, 391(6669): 806-811 (1998).
Japanese Patent Office, International Search Report in International Patent Application No. PCT/JP2016/059779 (dated Jun. 7, 2016).
Kitamatsu et al., "Carrier PNA for shRNA delivery into cells," Bioorg. Med. Chem. Lett., 19(13): 3410-3413 (2009).
Mäkilä et al., "Synthesis of multi-galactose-conjugated 2'-O-methyl oligoribonucleotides and their in vivo imaging with positron emission tomography," Bioorg. Med. Chem., 22(24): 6806-6813 (2014).
Nitin et al., "Peptide-linked molecular beacons for efficient delivery and rapid mRNA detection in living cells," Nucleic Acids Res., 32(6): e58 (2004).

(Continued)

Primary Examiner — Ekaterina Poliakova-Georgantas
(74) Attorney, Agent, or Firm — Leydig, Voit & Mayer, Ltd.

(57) ABSTRACT

The present invention provides a single-stranded nucleic acid molecule having a delivery function and capable of inhibiting expression of a target gene. The single-stranded nucleic acid molecule of the present invention is a single-stranded nucleic acid molecule composed of a region (Xc), a linker region (Lx) and a region (X), wherein said region (Xc) is complementary to said region (X), at least one of said region (X) and said region (Xc) contains an expression inhibitory sequence that inhibits expression of the target gene, and a bio-related substance having a delivery function is bonded to at least one selected from the group consisting of the 5'-terminus, the 3'-terminus, and said linker region (Lx).

22 Claims, 17 Drawing Sheets

Specification includes a Sequence Listing.

(56) References Cited

U.S. PATENT DOCUMENTS

| | | |
|---|---|---|
| 2005/0075492 A1 | 4/2005 | Chen et al. |
| 2005/0209141 A1 | 9/2005 | Silver et al. |
| 2005/0222009 A1 | 10/2005 | Lamensdorf et al. |
| 2005/0233455 A1 | 10/2005 | Damha et al. |
| 2006/0111312 A1 | 5/2006 | Eshleman et al. |
| 2006/0130176 A1 | 6/2006 | Reyes-Taboada et al. |
| 2006/0276421 A1 | 12/2006 | Kunugiza et al. |
| 2007/0037167 A1 | 2/2007 | Wohlgemuth et al. |
| 2007/0244058 A1 | 10/2007 | Ohgi et al. |
| 2007/0270365 A1 | 11/2007 | Jimenez et al. |
| 2008/0032918 A1 | 2/2008 | Silver et al. |
| 2008/0050744 A1 | 2/2008 | Brown et al. |
| 2008/0199853 A1 | 8/2008 | Wohlgemuth et al. |
| 2009/0005332 A1 | 1/2009 | Hauser et al. |
| 2009/0081274 A1 | 3/2009 | Silver et al. |
| 2009/0123501 A1* | 5/2009 | Levitt ............. A61K 39/0011 424/277.1 |
| 2009/0130751 A1 | 5/2009 | Davidson et al. |
| 2009/0176723 A1 | 7/2009 | Brown et al. |
| 2009/0239814 A1 | 9/2009 | Manoharan et al. |
| 2009/0263796 A1 | 10/2009 | Wohlgemuth et al. |
| 2009/0292005 A1 | 11/2009 | Ohgi et al. |
| 2010/0009377 A1 | 1/2010 | Wohlgemuth et al. |
| 2010/0137407 A1 | 6/2010 | Abe et al. |
| 2010/0221266 A1 | 9/2010 | Gregory et al. |
| 2010/0292310 A1 | 11/2010 | Kelley et al. |
| 2010/0317714 A1 | 12/2010 | Xi et al. |
| 2011/0034545 A1 | 2/2011 | Kubo et al. |
| 2011/0052666 A1 | 3/2011 | Kaemmerer et al. |
| 2011/0055965 A1 | 3/2011 | Abe et al. |
| 2011/0064792 A1 | 3/2011 | Humphries et al. |
| 2011/0070584 A1 | 3/2011 | Wohlgemuth et al. |
| 2011/0159586 A1 | 6/2011 | Hauser |
| 2011/0190142 A1 | 8/2011 | Funke-Kaiser et al. |
| 2011/0200582 A1 | 8/2011 | Baryza et al. |
| 2011/0262914 A1 | 10/2011 | Wohlgemuth et al. |
| 2012/0004280 A1* | 1/2012 | Jadhav ............. C12N 15/1138 514/44 A |
| 2012/0010271 A1 | 1/2012 | Ohgi et al. |
| 2012/0021516 A1 | 1/2012 | Hannon et al. |
| 2012/0035246 A1 | 2/2012 | Ohgi et al. |
| 2012/0135521 A1 | 5/2012 | Eshleman et al. |
| 2012/0184598 A1 | 7/2012 | Hauser |
| 2013/0017223 A1* | 1/2013 | Hope ............... A61K 9/1272 424/278.1 |
| 2013/0178514 A1 | 7/2013 | Deshmukh et al. |
| 2013/0179999 A1 | 7/2013 | Hannon et al. |
| 2013/0190494 A1 | 7/2013 | Carson et al. |
| 2013/0225652 A1 | 8/2013 | Chorn et al. |
| 2013/0253038 A1 | 9/2013 | Koizumi et al. |
| 2014/0171486 A1 | 6/2014 | Ohgi et al. |
| 2014/0171633 A1 | 6/2014 | Ohgi et al. |
| 2014/0329886 A1 | 11/2014 | Ohgi et al. |
| 2015/0073124 A1 | 3/2015 | Ohgi et al. |
| 2015/0105443 A1 | 4/2015 | Ohgi et al. |
| 2016/0319282 A1 | 11/2016 | Kuroda et al. |
| 2017/0037398 A1 | 2/2017 | Kuroda et al. |
| 2017/0088837 A1 | 3/2017 | Singer et al. |
| 2017/0306325 A1 | 10/2017 | Ohgi et al. |
| 2018/0326091 A1 | 11/2018 | Aoki et al. |
| 2019/0010503 A1 | 1/2019 | Ishida et al. |
| 2019/0270707 A1 | 9/2019 | Baiocchi et al. |

FOREIGN PATENT DOCUMENTS

| | | |
|---|---|---|
| CN | 101121934 A | 2/2008 |
| CN | 101679962 A | 3/2010 |
| CN | 101981185 A | 2/2011 |
| CN | 101845071 B | 2/2012 |
| CN | 102559666 A | 7/2012 |
| CN | 102784398 A | 11/2012 |
| CN | 102918158 A | 2/2013 |
| CN | 103052711 A | 4/2013 |
| CN | 103370416 A | 10/2013 |
| DE | 873543 C | 4/1953 |
| EP | 1013770 A1 | 6/2000 |
| EP | 1669450 A1 | 6/2006 |
| EP | 2143792 A1 | 1/2010 |
| EP | 2233573 A1 | 9/2010 |
| EP | 2256191 A1 | 12/2010 |
| EP | 2302055 A1 | 3/2011 |
| EP | 1669450 B1 | 11/2011 |
| EP | 2431466 A1 | 3/2012 |
| EP | 2436767 A1 | 4/2012 |
| EP | 2527440 A1 | 11/2012 |
| EP | 2562257 A1 | 2/2013 |
| EP | 2647713 A1 | 10/2013 |
| EP | 2801617 A1 | 11/2014 |
| JP | 2004-524032 A | 8/2004 |
| JP | 2005-508634 A | 4/2005 |
| JP | 2005-521393 A | 7/2005 |
| JP | 2007-508030 A | 4/2007 |
| JP | 2007-516695 A | 6/2007 |
| JP | 2008-510786 A | 4/2008 |
| JP | 2008-519606 A | 6/2008 |
| JP | 2008-526213 A | 7/2008 |
| JP | 2008-220366 A | 9/2008 |
| JP | 2008-239596 A | 10/2008 |
| JP | 2008-278784 A | 11/2008 |
| JP | 2010-104368 A | 5/2010 |
| JP | 2010-527616 A | 8/2010 |
| JP | 2011-501662 A | 1/2011 |
| JP | 2011-504730 A | 2/2011 |
| JP | 2011-220969 A | 11/2011 |
| JP | 2013-055913 A | 3/2013 |
| JP | 2013-153736 A | 8/2013 |
| RU | 2410430 C2 | 1/2011 |
| WO | WO 1995/029241 A2 | 11/1995 |
| WO | WO 1998/016550 A1 | 4/1998 |
| WO | WO 2003/068798 A1 | 8/2003 |
| WO | WO 2003/079757 A2 | 10/2003 |
| WO | WO 2004/015075 A2 | 2/2004 |
| WO | WO 2004/015107 A2 | 2/2004 |
| WO | WO 2004/058886 A1 | 7/2004 |
| WO | WO 2004/090108 A2 | 10/2004 |
| WO | WO 2005/019453 A2 | 3/2005 |
| WO | WO 2005/030960 A1 | 4/2005 |
| WO | WO 2005/037317 A2 | 4/2005 |
| WO | WO 2006/022325 A1 | 3/2006 |
| WO | WO 2006/024880 A2 | 3/2006 |
| WO | WO 2006/074108 A2 | 7/2006 |
| WO | WO 2006/088490 A2 | 8/2006 |
| WO | WO 2006/137941 A2 | 12/2006 |
| WO | WO 2007/099981 A1 | 9/2007 |
| WO | WO 2007/131237 A2 | 11/2007 |
| WO | WO 2008/116094 A2 | 9/2008 |
| WO | WO 2008/137862 A2 | 11/2008 |
| WO | WO 2008/137867 A2 | 11/2008 |
| WO | WO 2008/140126 A1 | 11/2008 |
| WO | WO 2008/147839 A1 | 12/2008 |
| WO | WO 2009/000520 A1 | 12/2008 |
| WO | WO 2009/029690 A1 | 3/2009 |
| WO | WO 2009/054551 A2 | 4/2009 |
| WO | WO 2009/065022 A2 | 5/2009 |
| WO | WO 2009/073809 A2 | 6/2009 |
| WO | WO 2009/076321 A2 | 6/2009 |
| WO | WO 2009/102081 A1 | 8/2009 |
| WO | WO 2009/126563 A1 | 10/2009 |
| WO | WO 2009/143619 A1 | 12/2009 |
| WO | WO 2010/056737 A2 | 5/2010 |
| WO | WO 2010/058824 A1 | 5/2010 |
| WO | WO 2011/008730 A2 | 1/2011 |
| WO | WO 2011/009624 A1 | 1/2011 |
| WO | WO 2011/055888 A1 | 5/2011 |
| WO | WO 2011/076807 A2 | 6/2011 |
| WO | WO 2011/119887 A1 | 9/2011 |
| WO | WO 2011/132672 A1 | 10/2011 |
| WO | WO 2011/133889 A2 | 10/2011 |
| WO | WO 2012/005368 A1 | 1/2012 |
| WO | WO 2012/012676 A2 | 1/2012 |
| WO | WO 2012/017919 A1 | 2/2012 |
| WO | WO 2012/030683 A2 | 3/2012 |
| WO | WO 2012/074038 A1 | 6/2012 |

(56) References Cited

FOREIGN PATENT DOCUMENTS

| | | |
|---|---|---|
| WO | WO 2012/106591 A1 | 8/2012 |
| WO | WO 2012/161124 A1 | 11/2012 |
| WO | WO 2013/077446 A1 | 5/2013 |
| WO | WO 2013/103146 A1 | 7/2013 |
| WO | WO 2003/072745 A2 | 9/2013 |
| WO | WO 2013/133221 A1 | 9/2013 |
| WO | WO 2013/166155 A1 | 11/2013 |
| WO | WO 2013/180038 A1 | 12/2013 |
| WO | WO 2014/190157 A1 | 11/2014 |
| WO | WO 2015/093495 A1 | 6/2015 |
| WO | WO 2015/099187 A1 | 7/2015 |
| WO | WO 2015/099188 A1 | 7/2015 |
| WO | WO 2015/179724 A1 | 11/2015 |

OTHER PUBLICATIONS

Nitin et al., "NLS Peptide Conjugated Molecular Beacons for Visualizing Nuclear RNA in Living Cells," *Bioconjug. Chem.*, 19(11): 2205-2211 (2008).
Zhu et al., "Targeted Delivery of siRNA to Hepatocytes and Hepatic Stellate Cells by Bioconjugation," *Bioconjug. Chem.*, 21(11): 2119-2127 (2010).
European Patent Office, Extended European Search Report in European Patent Application No. 16772690.0 (dated Jan. 18, 2019).
Baumann et al., "miRNA-based therapies: strategies and delivery platforms for oligonucleotide and non-oligonucleotide agents," *Future Med. Chem.*, 6(17): 1967-1984 (2014).
Jeong et al., "siRNA Conjugate Delivery Systems," *Bioconjug. Chem.*, 20(1): 5-14 (2009).
Seo et al., "Cholesterol-Linked Fluorescent Molecular Beacons with Enhanced Cell Permeability," *Bioconjug. Chem.*, 17(5): 1151-1155 (2006).
Shim et al., "Efficient and targeted delivery of siRNA in vivo," *FEBS J.*, 277(23): 4814-4827 (2010).
Upert et al., "Inhibition of HIV Replication by Cyclic and Hairpin PNAs Targeting the HIV-1 TAR RNA Loop," *J. Nucleic Acids*, 2012: 591025 (2012).
Abe et al., "Specific inhibition of influenza virus RNA polymerase and nucleoprotein gene expression by circular dumbbell RNA/DNA chimeric oligonucleotides containing antisense phosphodiester oligonucleotides," *FEBS Lett.*, 425(1): 91-96 (1998).
Abe et al., "Dumbbell-Shaped Nanocircular RNAs for RNA Interference," *J. Am. Chem. Soc.*, 129(49): 15108-15109 (2007).
Abe et al., "Synthesis, Structure, and Biological Activity of Dumbbell-Shaped Nanocircular RNAs for RNA Interference," *Bioconjug. Chem.*, 22(10): 2082-2092 (2011).
Anderson et al., "Bispecific Short Hairpin siRNA Constructs Targeted to CD4, CXCR4, and CCR5 Confer HIV-1 Resistance," *Oligonucleotides*, 13(5): 303-312 (2003).
Bailén et al., "Direct synthesis of hydroxamates from carboxylic acids using 2-mercaptopyridone-1-oxide-based thiouronium salts," *Tetrahedron Letters*, 42(30): 5013-5016 (2001).
Bosi et al., "Antimycobacterial Activity of Ionic Fullerene Derivatives," *Bioorg. Med. Chem. Lett.*, 10(10): 1043-1045 (2000).
Bradshaw et al., "A Simple and Convenient Method for the Preparation of N,N'-Dibenzyldiaza-crown Compounds," *Journal of Organic Chemistry*, 53(8): 1808-1810 (1988).
Bramsen et al., "Improved silencing properties using small internally segmented interfering RNAs," *Nucleic Acids Res.*, 35(17): 5886-5897 (2007).
Cifuentes et al., "A Novel miRNA Processing Pathway Independent of Dicer Requires Argonaute2 Catalytic Activity," *Science*, 328(5986): 1694-1698 (2010).
Cheloufi et al., "A Dicer-independent miRNA biogenesis pathway that requires Ago catalysis," *Nature*, 465(7298): 584-589 (2010).
Chen et al., "The hsa-let-7a miRNA Enhances Ara-C Induced Apoptosis in Human Acute Myeloid Leukemia Cells," *Clinical Lymphoma, Myeloma & Leukemia*, 13 (Supplement 2): S368, Abstract 203 (Sep. 2013).

Cheng et al., "TGF-β1 Gene Silencing for Treating Liver Fibrosis," *Mol. Pharm.*, 6(3): 772-779 (2009).
Chorn et al., "Single-stranded microRNA mimics," *RNA*, 18(10): 1796-1804 (2012).
Clusel et al., "Ex vivo regulation of specific gene expression by nanomolar concentration of double-stranded dumbbell oligonucleotides," *Nucleic Acids Res.*, 21(15): 3405-3411 (1993).
Collins et al., "The Schistosomicidal and Toxic Effects on Some aω-DI(p-aminophenoxy)alkanes and Related Monoamines," *Br. J. Pharmacol. Chemother.*, 13(3): 238-243 (1958).
Confalone et al., "Design and Synthesis of Potential DNA Cross-Linking Reagents Based on the Anthramycin Class of Minor Groove Binding Compounds," *J. Org. Chem.*, 53(3): 482-487 (1988).
Dankwardt, "Solid Phase Synthesis of Hydroxamic Acids," *Synlett*, 1998(7): 761 (Jul. 1998).
De La Torre et al., "Synthesis of Oligonucleotides Carrying Anchoring Groups and Their Use in the Preparation of Oligonucleotide-Gold Conjugates," *Helvetica Chimica Acta*, 85: 2594-2607 (2002).
Deiters, Alexander, "Small Molecule Modifiers of the microRNA and RNA Interference Pathway," *The AAPS Journal*, 12(1): 51-60 (Mar. 2010).
Elbashir et al., "Functional anatomy of siRNAs for mediating efficient RNAi in Drosophila melanogaster embryo lysate," *EMBO J.*, 20(23): 6877-6888 (2001).
Gatto et al., "Syntheses and Binding Properties of Bibracchial Lariat Ethers (BiBLEs): Survey of Synthetic Methods and Cation Selectivities," *J. Org. Chem.*, 51(26): 5373-5384 (1986).
Ge et al., "Minimal-length short hairpin RNAs: The relationship of structure and RNAi activity," *RNA*, 16(1): 106-117 (2010).
Genbank, "Homo sapiens periostin, osteoblast specific factor (POSTN), transcript variant 1, mRNA," Accession No. NM_006475.2 (2008).
Graubaum et al., "New Cryptands with 1,3,5-Triazines as Ring Building Blocks," *J. Prakt. Chem.*, 337(1): 534-537 (1995).
Guennewig et al., "Synthetic pre-microRNAs reveal dual-strand activity of miR-34a on TNF-α," *RNA*, 20(1): 61-75 (2013).
Hamazaki et al., "Inhibition of Influenza Virus Replication in MDCK Cells by Circular Dumbbell RNA/DNA Chimeras with Closed Alkyl Loop Structures," *Helvetica Chimica Acta*, 85(7): 2183-2194 (2002).
Hoogerhout et al., "Synthesis of fragments of the capsular polysaccharide of Haemophilus influenzae type B, comprising two or three repeating units," *Tetrahedron Letters*, 28(14): 1553-1556 (1987).
Hosoya et al., "Sequence-specific inhibition of a transcription factor by circular dumbbell DNA oligonucleotides," *FEBS Lett.*, 461(3): 136-140 (1999).
Ihara et al., "Enantioselective ester hydrolysis by hydroxamic acids of N-benzyloxycarbonyl-L-amino acids or optically active amines in cetyltrimethylammonium bromide," *Journal of Organic Chemistry*, 45(9): 1623-1625 (1980).
Jakobsen et al., "Polyaza crown ethers as nonnucleosidic building blocks in DNA-conjugates," 234th American Chemical Society (ACS) National Meeting, Abstract BIOL-071 (Aug. 19, 2007).
Johnson et al., "Somatic activation of the K-ras oncogene causes early onset lung cancer in mice," *Nature*, 410(6832): 1111-1116 (2001).
Kumar et al., "Pyrrolidine Nucleic Acids: DNA/PNA Oligomers with 2-Hydroxy/Aminomethyl-4-(thymin-1-yl)pyrrolidine-N-acetic acid," *Org. Lett.*, 3(9): 1269-1272 (2001).
Kunugiza et al., "Inhibitory effect of ribbon-type NF-κB decoy oligodeoxynucleotides on osteoclast induction and activity in vitro and in vivo," *Arthritis Res. Ther.*, 8(4): R103 (2006).
Leirdal et al., "Gene silencing in mammalian cells by preformed small RNA duplexes," *Biochem. Biophys. Res. Commun.*, 295(3): 744-748 (2002).
Limbach et al., "Summary: the modified nucleosides of RNA," *Nucleic Acids Res.*, 22(12): 2183-2196 (1994).
Li et al., "miRNA arm selection and isomiR distribution in gastric cancer," *BMC Genomics*, 13(Suppl. 1): S13 (2012).
Liu et al., "Enhanced proliferation, invasion, and epithelial-mesenchymal transition of nicotine-promoted gastric cancer by periostin," *World J. Gastroenterol.*, 17(21): 2674-2680 (2011).

(56) References Cited

OTHER PUBLICATIONS

Liu et al., "Membrane Anchored Immunostimulatory Oligonucleotides for in Vivo Cell Modification and Localized Immunotherapy," *Angewandte Chemie, International Edition*, 50(31): 7052-7055 and supporting information (2011).

Lonkar et al., "Design and synthesis of conformationally frozen peptide nucleic acid backbone: chiral piperidine PNA as a hexitol nucleic acid surrogate," *Bioorg. Med. Chem. Lett.*, 14(9): 2147-2149 (2004).

Ma et al., "Designing Ago2-specific siRNA/shRNA to Avoid Competition with Endogenous miRNAs," *Mol. Ther. Nucleic Acids*, 3: e176 (2014).

Maeda et al., "Synthesis of N-Unsubstituted Di- and Triaza Crown Ethers," *Bulletin of the Chemical Society of Japan*, 56(10): 3073-3077 (1983).

McAnuff et al., "Potency of siRNA Versus shRNA Mediated Knockdown in Vivo," *J. Pharm. Sci.*, 96(11): 2922-2930 (2007).

McManus et al., "Gene silencing using micro-RNA designed hairpins," *RNA*, 8(6): 842-850 (2002).

Michlewski et al., "Posttranscriptional Regulation of miRNAs Harboring Conserved Terminal Loops," *Mol. Cell*, 32(3): 383-393 (2008).

Ming et al., "The Tumor Research Frontiers," *Fourth Military Medical University Press*, 10 (Chinese Edition): 25 (2010), Office Action and Search Report in CN 20148007073.4 (dated Mar. 30, 2018).

Myburgh et al., "Optimization of Critical Hairpin Features Allows miRNA-based Gene Knockdown Upon Single-copy Transduction," *Mol. Ther.—Nucleic Acids*, 3: e207 (2014).

Neilsen et al., "IsomiRs—the overlooked repertoire in the dynamic MicroRNAome," *Trends in Genetics*, 28(11): 544-549 (2012).

Nilsson et al., "Padlock probes: Circularizing Oligonucleotides for Localized DNA Detection," *Science*, 265(5181): 2085-2088 (1994).

Nykanen et al., "ATP Requirements and Small Interfering RNA Structure in the RNA Interference Pathway," *Cell*, 107(3): 309-321 (2001).

Oliveira et al., "Efficient and Expeditious Protocols for the Synthesis of Racemic and Enantiomerically Pure Endocyclic Enecarbamates from N-Acetyl Lactams and N-Acyl Pyrrolidines," *J. Org. Chem.*, 64(18): 6646-6652 (1999).

Paddison et al., "Short hairpin RNAs (shRNAs) induce sequence-specific silencing in mammalian cells," *Genes Dev.*, 16(8): 948-958 (2002).

Püschl et al., "Pyrrolidine PNA: A Novel Conformationally Restricted PNA Analogue," *Org. Lett.*, 2(26): 4161-4163 (2000).

Schmitter et al., "Effects of Dicer and Argonaute down-regulation on mRNA levels in human HEK293 cells," *Nucleic Acids Res.*, 34(17): 4801-4815 (2006).

She et al., "Organic and Biochemistry," *China Forestry Publishing House*, 3rd Edition (Chinese Edition), p. 280 (2009), Office Action and Search Report in CN 20148007073.4 (dated Mar. 30, 2018).

Sommer et al., "Synthesis of Potentially Cytoactive Amino Acid Amide Mustards," *Journal of Medicinal Chemistry*, 9(1): 84-88 (1966).

Sonoke et al., "Tumor Regression in Mice by Delivery of Bcl-2 Small Interfering RNA with Pegylated Cationic Liposomes," *Cancer Research*, 68(21): 8843-8851 (Nov. 1, 2008).

Takaoka, "Natural Immunity and Viral Infection" (2011) [obtained at http://www.igm.hokudai.ac.jp/sci/files/innate_virus.pdf on Sep. 19, 2018], Office Action in JP 2016-566558 (dated Oct. 2, 2018).

Takeshita et al., "Systemic Delivery of Synthetic MicroRNA-16 Inhibits the Growth of Metastatic Prostate Tumors via Downregulation of Multiple Cell-cycle Genes," *Molecular Therapy*, 18(1): 181-187 (Jan. 2010).

Teramoto et al., "Prediction of siRNA functionality using generalized string kernel and support vector machine," *FEBS Lett.*, 579(13): 2878-2882 (2005).

Trang et al., "Systemic Delivery of Tumor Suppressor microRNA Mimics Using a Neutral Lipid Emulsion Inhibits Lung Tumors in Mice," *Mol. Ther.*, 19(6): 1116-1122 (2011).

Völler et al., "Strong reduction of AGO2 expression in melanoma and cellular consequences," *Br. J. Cancer*, 109(12): 3116-3124 (2013).

Wang et al., "Predicting siRNA potency with random forests and support vector machines," *BMC Genomics*, 11(Suppl. 3): S2 (2010).

Watanabe et al., "Periostin regulates MMP-2 expression via the $\alpha v\beta 3$ integrin/ERK pathway in human periodontal ligament cells," *Archives of Oral Biology*, 57(1): 52-59 (2012).

Webster et al., "Comparison of Solution-Phase and Solid-Phase Syntheses of a Restrained Proline-Containing Analogue of the Nodularin Macrocycle," *Tetrahedron Lett.*, 38(32): 5713-5716 (1997).

Winter et al., "Loop-miRs: active microRNAs generated from single-stranded loop regions," *Nucleic Acids Res.*, 41(10): 5503-5512 (2013).

Wu et al., "Improved siRNA/shRNA Functionality by Mismatched Duplex," *PLoS One*, 6(12): e28580 (2011).

Yamakawa et al. "Properties and Anti-HIV Activity of Nicked Dumbbell Oligonucleotides," *Nucleosides & Nucleotides*, 15(1-3): 519-529 (1996).

Yang et al., "Conserved vertebrate mir-451 provides a platform for Dicer-independent, Ago2-mediated microRNA biogenesis," *Proc. Natl. Acad. Sci. U.S.A.*, 107(34): 15163-15168 (2010).

Yang et al., "Functional parameters of Dicer-independent microRNA biogenesis," *RNA*, 18(5): 945-957 (2012).

Yin et al., "HAS-miR-34a as a molecular marker for early diagnosis of renal cell carcinoma," *Modern Oncology*, 20(7): 1398-1401 (2012).

Yoshida et al., "Increased Expression of Periostin in Vitreous and Fibrovascular Membranes Obtained from Patients with Proliferative Diabetic Retinopathy," *Investigative Ophthalmology & Visual Science*, 52(8): 5670-5678 (2011).

Yu et al., "RNA interference by expression of short-interfering RNAs and hairpin RNAs in mammalian cells," *Proc. Natl. Acad. Sci. USA*, 99(9): 6047-6052 (2002).

Zeng et al., "Structural requirements for pre-microRNA binding and nuclear export by Exportin 5," *Nucleic Acids Res.*, 32(16): 4776-4785 (2004).

Australian Patent Office, Patent Examination Report No. 1 in Australian Patent Application No. 2011274854 (dated Oct. 24, 2014).

Chinese Patent Office, Office Action and Search Report in Chinese Patent Application No. 201180027223.1 (dated Nov. 21, 2013), Search Report identifies references and relevance thereof.

Chinese Patent Office, Office Action and Search Report in Chinese Patent Application No. 201180037592.9 (dated Sep. 23, 2014), Search Report identifies references and relevance thereof.

Chinese Patent Office, Notification of the Second Office Action in Chinese Patent Application No. 201380028696.2 (dated Jul. 18, 2016).

Chinese Patent Office, Office Action and Search Report in Chinese Patent Application No. 201480070373.4 (dated Mar. 30, 2018), partial English translation of Search Report.

Chinese Patent Office, The First Office Action in Chinese Patent Application No. 201480076467.2 (dated Jul. 25, 2018).

European Patent Office, Supplementary European Search Report in European Patent Application No. 11746147.5 (dated Mar. 26, 2012).

European Patent Office, Communication Pursuant to Article 94(3) EPC in European Patent Application No. 11746147.5 (dated Apr. 20, 2012).

European Patent Office, Communication Pursuant to Article 94(3) EPC in European Patent Application No. 11746147.5 (dated Sep. 26, 2012).

European Patent Office, Communication Pursuant to Article 94(3) EPC in European Patent Application No. 11746147.5 (dated Mar. 25, 2013).

European Patent Office, Communication Pursuant to Article 94(3) EPC in European Patent Application No. 14873783.6 (dated Sep. 10, 2018).

European Patent Office, Supplementary European Search Report in European Patent Application No. 11748250.5 (dated Apr. 5, 2012).

European Patent Office, Communication Pursuant to Article 94(3) EPC in European Patent Application No. 11748250.5 (dated May 29, 2012).

(56) References Cited

OTHER PUBLICATIONS

European Patent Office, Supplementary European Search Report in European Patent Application No. 12864101.6 (dated Sep. 1, 2015).
European Patent Office, Extended European Search Report in European Patent Application No. 13184178.5 (dated Oct. 25, 2013).
European Patent Office, Extended European Search Report in European Patent Application No. 15169933.7 (dated Jul. 29, 2015).
European Patent Office, Extended European Search Report in European Patent Application No. 14873783.6 (dated Jul. 11, 2017).
European Patent Office, Communication Pursuant to Rule 164(1) EPC in European Patent Application No. 13167541.5 (dated Jul. 31, 2013).
European Patent Office, Communication Pursuant to Rule 164(1) EPC in European Patent Application No. 13797956.3 (dated Jan. 4, 2016).
Japanese Patent Office, International Search Report in International Patent Application No. PCT/JP2012/080461 (dated Jan. 22, 2013).
Japanese Patent Office, International Search Report in International Patent Application No. PCT/JP2012/084247 (dated Apr. 16, 2013).
Japanese Patent Office, International Search Report in International Patent Application No. PCT/JP2013/059494 (dated Jun. 4, 2013).
Japanese Patent Office, International Search Report in International Patent Application No. PCT/JP2013/064541 (dated Jul. 2, 2013).
Japanese Patent Office, International Search Report in International Patent Application No. PCT/JP2014/084724 (dated Mar. 24, 2015).
Japanese Patent Office, International Search Report in International Patent Application No. PCT/JP2015/086378 (dated Mar. 15, 2016).
Japanese Patent Office, Notice of Reasons for Refusal in Japanese Patent Application No. 2014-518427 (dated May 17, 2016).
Japanese Patent Office, Notice of Reasons for Refusal in Japanese Patent Application No. 2016-566558 (dated Oct. 2, 2018).
Japanese Patent Office, Notification of Reasons for Refusal in Japanese Patent Application No. 2015-555042 (dated Dec. 4, 2018).
U.S. Patent and Trademark Office, Supplemental Structure Search Results (ACS on STN) Referring to WO 2009/000520, HCAPLUS Accession No. 2009: 1297, Document No. 150: 95775, in U.S. Appl. No. 13/254,159, filed Nov. 9, 2012.
United States Patent and Trademark Office, Office Action in U.S. Appl. No. 13/254,159 (dated Nov. 21, 2012).
United States Patent and Trademark Office, Office Action in U.S. Appl. No. 14/135,468 (dated May 8, 2015).
Ivashchenko et al., "Specific Features of System Silencing of Homologous Sequences in the Course of RNA Interference," *Uspekhi Sovremennoj Biologii*, 129(5): 419-439 (2009), English abstract (p. 439).
Müller (editor), *Nucleic Acids from A to Z: A Concise Encyclopedia*, entry for "micro-RNA (miRNA)" p. 197 (2008), English version (p. 175).
Batenburg et al., "Combined Renin Inhibition/(Pro)Renin Receptor Blockade in Diabetic Retinopathy—A Study in Transgenic (mREN2)27 Rats," *PLoS One*, 9(6): e100954 (2014).
Danser et al., "Renin, Prorenin, and Immunoreactive Renin in Vitreous Fluid from Eyes With and Without Diabetic Retinopathy," *J. Clin. Endocrinol. Metabol.*, 68(1): 160-167 (1989).
Genbank, "*Homo sapiens* glyceraldehyde-3-phosphate dehydrogenase (GADPH), transcript variant 1, mRNA," Accession No. NM_002046 (2014) [obtained at www.ncbi.nlm.nih.gov on Oct. 7, 2019].
Genbank, "*Homo sapiens* ATPase H+ transporting accessory protein 2 (ATP6AP2), mRNA.," Accession No. NM_005765 (2019) [obtained at www.ncbi.nlm.nih.gov on Oct. 7, 2019].
Hamasaki et al., "Efficacy of a Novel Class of RNA Interference Therapeutic Agents," *PLoS One*, 7(8): e42655 (2012).
Kanda et al., "(Pro)renin receptor is associated with angiogenic activity in proliferative diabetic retinopathy," *Diabetologia*, 55: 3104-3443 (2012).
Kanda, "(Pro)renin Receptor in the Pathogenesis of Proliferative Diabetic Retinopathy," *Jpn. J. Ophthalmol.*, 118(11): 916-926 (2014), English abstract and Int'l Search Report in PCT/JP2016/089216 (dated Mar. 28, 2017).
Satofuka et al., "Suppression of Ocular Inflammation in Endotoxin-Induced Uveitis by Inhibiting Nonproteolytic Activation of Prorenin," *Invest. Ophthalmol. Vis. Sci.*, 47(6): 2686-2692 (2006).
Zuyeva et al., "Changes of retinal neurons and Muller glial cells in patients with type II diabetes in treatment of diabetic retinopathy with angiotensin-converting enzyme inhibitor," *Vestnik Oftamologii*, 129(3): 44-47 (2013), English abstract and Office Action in RU 2018127481 (dated Mar. 27, 2019).
European Patent Office, Extended European Search Report in European Patent Application No. 16881846 (dated Apr. 16, 2019).
Japanese Patent Office, International Search Report in International Patent Application No. PCT/JP2016/089216 (dated Mar. 28, 2017).
Russian Patent Office, Office Action and Search Report in Russian Patent Application No. 2018127481 (dated Mar. 27, 2019).
China National Intellectual Property Office, Office Action and Search Report in Chinese Patent Application No. 201180027223.1 (dated Nov. 21, 2013).
China National Intellectual Property Office, Office Action and Search Report in Chinese Patent Application No. 201180037592.9 (dated Sep. 23, 2014).
China National Intellectual Property Office, Office Action and Search Report in Chinese Patent Application No. 201480070373.4 (dated Mar. 30, 2018).
Genbank, "*Homo sapiens* catenin (cadherin-associated protein), beta 1, 88kDa (CTNNB1), transcript variant 1, mRNA," Accession No. NM_001904.3 (2010) [obtained at https://www.ncbi.nlm.nih.gov/nuccore/148228165?sat=14&satkey=4105514].
China National Intellectual Property Office, The Second Office Action in Chinese Patent Application No. 201480076467.2 (dated Jun. 5, 2019).
Japanese Patent Office, Office Action in Japanese Patent Application No. 2018-113017 (dated Jun. 11, 2019).
Japanese Patent Office, Office Action in Japanese Patent Application No. 2017-509942 (dated Jul. 2, 2019).
Russian Federal Service for Intellectual Property, Office Action in Russian Patent Application No. 2017126566 (dated Jun. 6, 2019).
NCBI, "*Homo sapiens* renin (REN), mRNA," NCBI Reference Sequence No. NM_000537.4 (2019).
Tarantul et al., "Single-stranded DNA (ssDNA)," Slovar biotekhnologicheskikh terminov (Dictionary of Bioengineering Terms), publication page and entry p. 478 (2009).
U.S. Appl. No. 13/254,150, filed Aug. 31, 2011.
U.S. Appl. No. 13/254,159, filed Aug. 31, 2011.
U.S. Appl. No. 14/134,704, filed Dec. 19, 2013.
U.S. Appl. No. 14/362,762, filed Jun. 4, 2014.
U.S. Appl. No. 14/403,259, filed Nov. 24, 2014.
U.S. Appl. No. 15/106,958, filed Jun. 21, 2016.
U.S. Appl. No. 15/108,453, filed Jun. 27, 2016.
U.S. Appl. No. 15/496,143, filed Apr. 25, 2017.
U.S. Appl. No. 15/539,226, filed Jun. 23, 2017.
U.S. Appl. No. 16/065,779, filed Jun. 22, 2018.
Kanda et al., "A Novel Single-Strand RNAi Therapeutic Agent Targeting the (Pro)renin Receptor Suppresses Ocular Inflammation," *Mol. Ther. Nucleic Acids*, 7: 116-126 (2017).

\* cited by examiner (A)

(B)

SINGLE-STRANDED NUCLEIC ACID MOLECULE HAVING DELIVERY FUNCTION AND GENE EXPRESSION REGULATING ABILITY

CROSS-REFERENCE TO RELATED APPLICATIONS

This patent application is the U.S. national phase of International Patent Application No. PCT/JP2016/059779, filed Mar. 26, 2016, which claims the benefit of Japanese Patent Application No. 2015-065770, filed on Mar. 27, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 8,901 bytes ASCII (Text) file named "733239Replacement-SequenceListing-2nd.txt," created Sep. 7, 2018.

TECHNICAL FIELD

The present invention relates to a single-stranded nucleic acid molecule having a delivery function and gene expression regulating ability, a composition containing same and use thereof.

BACKGROUND ART

As a technique for inhibiting gene expression, for example, RNA interference (RNAi) is known (Non-Patent Document 1). Inhibition of gene expression by RNA interference is generally carried out, for example, by administering a short double-stranded RNA molecule to a cell or the like. The aforementioned double-stranded RNA molecule is generally called siRNA (small interfering RNA). It has been reported that gene expression can also be inhibited by a circular RNA molecule having a double strand partially formed therein by intramolecular annealing (Patent Document 1). However, in these techniques, the RNA molecules to induce the inhibition of the gene expression have the following problems.

First, in order to produce the aforementioned siRNA, it is necessary to synthesize a sense strand and an antisense strand separately and to hybridize these strands at the end of the process. Thus, there is a problem of low manufacturing efficiency. Furthermore, when the aforementioned siRNA is administered to a cell, it is necessary to administer the siRNA to the cell while repressing the dissociation to single-stranded RNAs, which requires a laborious task of setting the conditions for handling the siRNA. The circular RNA molecule has a problem in that its synthesis is difficult. To deal with the situation, the present inventors constructed a new single-stranded nucleic acid molecule which solves the problem (patent documents 2, 3).

DOCUMENT LIST

Patent Documents patent document 1: JP-A-2008-278784
patent document 2: WO 2012/017919
patent document 3: WO 2013/180038

Non-Patent Document non-patent document 1: Fire, et al., Nature, vol. 391, p. 806-811, 1998

SUMMARY OF THE INVENTION

Problems to be Solved by the Invention

Moreover, such new single-stranded nucleic acid molecule is requested to further realize a superior delivery function to the target tissue or cell.

Therefore, the present invention aims to provide a single-stranded nucleic acid having a delivery function and capable of inhibiting expression of a target gene.

Means of Solving the Problems

To achieve the aforementioned object, the single-stranded nucleic acid molecule of the present invention is a single-stranded nucleic acid molecule for inhibiting expression of a target gene, which is composed of a region (X), a linker region (Lx) and a region (Xc), wherein
the aforementioned region (X) is complementary to the aforementioned region (Xc),
at least one of the aforementioned region (X) and the aforementioned region (Xc) comprises an expression inhibitory sequence that inhibits expression of the target gene, and a bio-related substance having a delivery function is bonded to at least one selected from the group consisting of the 5'-terminus, the 3'-terminus, and the aforementioned linker region (Lx) of the single-stranded nucleic acid molecule for inhibiting expression of a target gene.

Effect of the Invention

The single-stranded nucleic acid molecule of the present invention can realize a superior delivering function to a target tissue or cell without essentially requiring, for example, a carrier for the delivery. Therefore, for example, the toxicity of the carrier does not need to be considered, and a study for setting various conditions relating to the formation of a complex of a nucleic acid molecule and a carrier can be obviated. Consequently, for example, the labor and cost in terms of production and use can be reduced.

DESCRIPTION OF EMBODIMENTS

Figure 1:
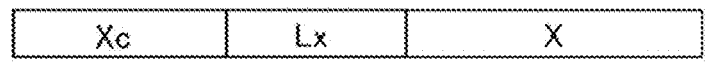
FIG. 1 shows schematic views illustrating an example of the single-stranded nucleic acid molecule of the present invention.
Figure 1:
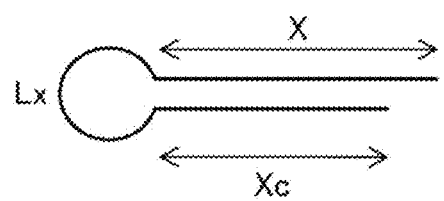

Unless otherwise specified, the terms used in the present specification mean what is generally meant by them in the art.

1. ssNc Molecule

The single-stranded nucleic acid molecule of the present invention is, as mentioned above, a single-stranded nucleic acid molecule for inhibiting expression of a target gene, which is composed of a region (X), a linker region (Lx) and a region (Xc), and is characterized in that the aforementioned region (X) is complementary to the aforementioned region (Xc), at least one of the aforementioned region (X) and the aforementioned region (Xc) comprises an expression inhibitory sequence that inhibits expression of the target gene, and a bio-related substance having a delivery function is bonded to at least one selected from the group consisting of the 5'-terminus, the 3'-terminus, and the aforementioned linker region (Lx) of the single-stranded nucleic acid molecule.

In the present invention, "inhibition of expression of a target gene" means, for example, inhibiting the expression of the aforementioned target gene. The mechanism by which the aforementioned inhibition is achieved is not particularly limited, and may be, for example, downregulation or silencing. The aforementioned inhibition of the expression of the target gene can be verified by, for example, a decrease in the amount of a transcription product derived from the target gene; a decrease in the activity of the aforementioned transcription product; a decrease in the amount of a translation product generated from the aforementioned target gene; a decrease in the activity of the aforementioned translation product; or the like. The aforementioned translation product may be, for example, mature proteins, precursor proteins before being subjected to processing or post-translational modification.

The single-stranded nucleic acid molecule of the present invention hereinafter also may be referred to as the "ssNc molecule" of the present invention. The ssNc molecule of the present invention can be used to inhibit, for example, the expression of a target gene in vivo or in vitro and can also be referred to as an "ssNc molecule for inhibiting the expression of a target gene" or "inhibitor of the expression of a target gene". Furthermore, the ssNc molecule of the present invention can inhibit the expression of the aforementioned target gene by, for example, RNA interference, and it can also be referred to as an "ssNc molecule for RNA interference", "molecule for inducing RNA interference", "RNA interference agent" or "RNA interference-inducing agent". The ssNc molecule of the present invention can also inhibit, for example, a side effect such as interferon induction.

In the ssNc molecule of the present invention, the 5'-terminus and the 3'-terminus are not linked to each other. Thus, it can also be referred to as a linear single-stranded nucleic acid molecule.

In the ssNc molecule of the present invention, the aforementioned region (Xc) is complementary to the aforementioned region (X), the aforementioned region (Xc) folds back toward the aforementioned region (X), and the aforementioned region (Xc) and the aforementioned region (X) can form a double strand by self-annealing.

In the ssNc molecule of the present invention, the aforementioned expression inhibitory sequence is a sequence that exhibits, for example, an activity of inhibiting the aforementioned expression of a target gene when the ssNc molecule of the present invention is introduced into a cell in vivo or in vitro. The aforementioned expression inhibitory sequence is not particularly limited, and can be set as appropriate depending on the kind of a target gene. As the aforementioned expression inhibitory sequence, for example, a sequence involved in RNA interference caused by siRNA can be used as appropriate. Generally, RNA interference is a phenomenon in which a long double-stranded RNA (dsRNA) is cleaved in a cell by Dicer to produce a double-stranded RNA (siRNA: small interfering RNA) composed of about 19 to 21 base pairs and having a protruding 3'-terminus, and one of the single-stranded RNAs binds to a target mRNA to degrade the aforementioned mRNA, whereby the translation of the mRNA is inhibited. As the sequence of the single-stranded RNA of the aforementioned siRNA binding to the aforementioned target mRNA, for example, various kinds of sequences for various kinds of target genes have been reported. In the present invention, for example, the sequence of the single-stranded RNA of the aforementioned siRNA can be used as the aforementioned expression inhibitory sequence. In the present invention, not only the sequences of the single-stranded RNA of the siRNA known at the time of the filing of the present application but also sequences that would be identified in the future can be used, for example, as the aforementioned expression inhibitory sequence.

The aforementioned expression inhibitory sequence is, for example, preferably at least 90% complementary, more preferably 95% complementary, still more preferably 98% complementary, and particularly preferably 100% complementary to a predetermined region of the aforementioned target gene. When such complementarity is satisfied, for example, an off-target effect can be reduced sufficiently.

It is speculated that the aforementioned inhibition of the expression of a target gene by the ssNc molecule of the present invention is achieved, for example, by RNA interference or a phenomenon similar to RNA interference (RNA interference-like phenomenon), which is caused by a structure configuring the aforementioned expression inhibitory sequence, in at least one of the aforementioned region (X) and the aforementioned region (Xc). It should be noted, however, that the present invention is by no means limited by this mechanism. Unlike the so-called siRNA, for example, the ssNc molecule of the present invention is not introduced to a cell or the like in the form of dsRNA composed of two-chains single-stranded RNAs, and it is not always necessary to cleave out the aforementioned expression inhibitory sequence in the cell. Thus, it can be said, for example, that the ssNc molecule of the present invention exhibits an RNA interference-like function.

In the ssNc molecule of the present invention, the aforementioned expression inhibitory sequence is included in at least one of the aforementioned region (X), and the aforementioned region (Xc), as described above. The ssNc molecule of the present invention may include, for example, one expression inhibitory sequence or two or more expression inhibitory sequences mentioned above.

In the latter case, the ssNc molecule of the present invention may include, for example, two or more identical expression inhibitory sequences for the same target gene; two or more different expression inhibitory sequences for the same target gene; or two or more different expression inhibitory sequences for different target genes. When the ssNc molecule of the present invention includes two or more expression inhibitory sequences mentioned above, the positions of the respective expression inhibitory sequences are not particularly limited, and they may be in one region or different regions selected from the aforementioned region (X), and the aforementioned region (Xc). When the ssNc molecule of the present invention includes two or more expression inhibitory sequences mentioned above for different target genes, for example, the ssNc molecule of the present invention can inhibit the expressions of two or more kinds of different target genes.

In the ssNc molecule of the present invention, the aforementioned expression inhibitory sequence only needs to have, for example, an expression inhibitory activity and may also be a mature miRNA sequence. The miRNA generation process and protein expression inhibitory process by miRNA in the body are as described below. First, a single-stranded miRNA transcript (Pri-miRNA) having a cap structure at the 5'-terminus and a poly A structure at the 3'-terminus is expressed in the nucleus. The aforementioned Pri-miRNA has a hairpin structure. The aforementioned Pri-miRNA is cleaved by RNase (Drosha) to produce a single-stranded precursor (Pre-miRNA). The aforementioned Pre-miRNA has a hairpin structure having a stem region and a loop region. The aforementioned Pre-miRNA is transported to the cytoplasm, cleaved by RNase (Dicer) and, from the stem structure thereof, a double-stranded miRNA having overhung of several bases (e.g., 1-4 bases) at the 3'-terminus is produced. A single-stranded mature miRNA from the double-stranded miRNA is bonded to a complex similar to RISC (RNA induced Silencing Complex) and the mature miRNA/RISC complex is bonded to a particular mRNA, whereby translation of protein from the aforementioned mRNA is suppressed. In the present invention, the sequence of the aforementioned mature miRNA can be used as the aforementioned expression inhibitory sequence.

It should be noted that the point of the present invention is not the sequence information of the aforementioned expression inhibitory sequence for the aforementioned target gene, but, for example, the structure of a nucleic acid molecule that allows function of the aforementioned target gene expression inhibitory activity due to the aforementioned expression inhibitory sequence in a cell. Therefore, in the present invention, not only the sequences of the single-stranded mature miRNA of the miRNA known at the time of the filing of the present application but also sequences that would be identified in the future can be used, for example, as the aforementioned expression inhibitory sequence.

As mentioned above, in the body, the aforementioned Pre-miRNA is cleaved, and the aforementioned mature miRNA sequence is produced from one of the strands (also referred to as guide strand) of the stem structure. In this case, a minor miRNA* sequence (also referred to as passenger strand) is produced from the other strand of the aforementioned stem structure. The aforementioned minor miRNA* sequence is generally a complementary strand having mismatch in one to several bases when aligned with the aforementioned Pre-miRNA. The ssNc molecule of the present invention may further have, for example, the aforementioned minor miRNA* sequence.

The aforementioned mature miRNA sequence and the aforementioned minor miRNA* sequence may have a base that becomes noncomplementary when the both are aligned. The aforementioned minor miRNA* has, for example, complementarity of, for example, 60-100% to the aforementioned mature miRNA sequence. The aforementioned mature miRNA sequence and the aforementioned minor miRNA* may each have, in the inside thereof, the aforementioned base (e.g., one or several bases) that becomes noncomplementary. The number of the aforementioned base is, for example, 2-15 bases. The aforementioned noncomplementary base may be, for example, continuous or noncontinuous.

The length of the aforementioned minor miRNA* sequence is not particularly limited, and it is different from the length of the aforementioned mature miRNA sequence by, for example, 0-10 bases, preferably 0-7 bases, more preferably 0-5 bases. The aforementioned minor miRNA*sequence and the aforementioned mature miRNA sequence may have, for example, the same length or the former may be longer or the latter may be longer.

In the ssNc molecule of the present invention, the aforementioned region (Xc) is complementary to the aforementioned region (X). It is only necessary that the aforementioned region (Xc) has a sequence complementary to the entire region or part of the aforementioned region (X). Specifically, for example, preferably, the aforementioned region (Xc) includes or is composed of a sequence complementary to the entire region or part of the aforementioned region (X). The aforementioned region (Xc) may be, for example, perfectly complementary to the entire region or part of the aforementioned region (X), or one or a few bases in the aforementioned region (Xc) may be noncomplementary to the same.

The ssNc molecule of the present invention may be configured so that it has a linker region (Lx) between the aforementioned region (Xc) and the aforementioned region (X) and the aforementioned regions (Xc) and (X) are linked via the aforementioned linker region (Lx).

The aforementioned linker region (Lx) preferably has a structure free of self-annealing inside the very region.

As the structure of the aforementioned linker region (Lx), for example, the structures described in International Application No. PCT/JP2011/065737 (filing date: Jul. 8, 2011), International Application No. PCT/JP2011/067292 (filing date: Jul. 28, 2011) and International Application No. PCT/JP2012/001711 (filing date: Dec. 29, 2012) can be used, and these documents can be referred to for the present invention.

In the ssNc molecule of the present invention, the aforementioned bio-related substance is a substance that shows affinity for living organisms and can also be referred to as a biocompatible substance. The aforementioned bio-related substance is, for example, a substance contained in a component derived from a living organism or a substance having a structure the same as or similar to that of the component. The aforementioned bio-related substance is not particularly limited as long as it shows affinity for living organisms and, for example, various functional substances such as vitamin, hormone and the like can be mentioned. More specifically, for example, it is as follows.

For example, the first form of the aforementioned bio-related substance is lipid. The ssNc molecule of the present invention can improve, for example, delivery and introduction efficiency into a target cell and/or resistance to enzymatic degradation by having a lipid. This is assumed to be attributable to, for example, the following mechanism. That is, the ssNc molecule of the present invention has improved permeability of cellular membrane and improved resistance to enzymatic degradation by forming a micelle structure as a whole with the aforementioned lipid region and other nucleic acid regions. In addition, the ssNc molecule of the present invention is understood to have more improved mobility in living organisms since the aforementioned lipid region and other nucleic acid regions form an exosome-like complex as a whole. The present invention is not limited to such mechanisms.

Specific examples of the aforementioned lipid include simple lipid, complex lipid, derived lipid, liposoluble vitamin and the like. Examples of the aforementioned simple lipid include single-chain lipid which is an ester of fatty acid and alcohol. Examples of the aforementioned complex lipid include a double-chain phospholipid, glycolipid and the like. Examples of the aforementioned derived lipid include fatty acids such as saturated fatty acid, unsaturated fatty acid and the like, steroids such as cholesterol, steroid hormone and the like, and the like. Examples of the aforementioned liposoluble vitamin include retinol, tocopherol, calciferol and the like. Besides these, examples of the aforementioned lipid include fats and oils, hydrocarbons such as squalene and the like, higher alcohol and the like.

The aforementioned single-chain lipid is represented by, for example, RCOO—. The aforementioned double-chain lipid is represented by, for example, the following formula. R is, for example, saturated fatty acids such as palmitic acid, stearic acid, myristic acid and the like, unsaturated fatty acids such as oleic acid and the like, and the like. In addition, as the aforementioned double-chain lipid, DOPE can be mentioned. The aforementioned lipid is at least one selected from the group consisting of palmitic acid, myristic acid, stearic acid, oleic acid, DOPE and cholesterol.

[Chem. 1]

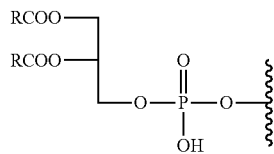

The second form of the aforementioned bio-related substance is, for example, peptide. The ssNc molecule of the present invention can improve, for example, delivery and introduction efficiency into a target cell and/or resistance to enzymatic degradation by having a peptide.

The aforementioned peptide is not particularly limited and examples include a protein bindable to a membrane protein of a target cell or a peptide thereof; a protein selectively incorporated into the target site or a peptide thereof (also referred to as membrane-permeable peptide), a biological molecule acting on a particular receptor or a peptide thereof, an antibody protein reacting with an antigen expressed on a cellular surface or a peptide thereof, a peptide interacting with a particular protein, and the like. Specific examples of the aforementioned peptide include polyarginine peptide (RRRRRRRRR, RRRRRRR) (SEQ ID NOs: 1 and 2), penetratin (RQIKIWFGNRRMKWKK, RRMKWKK) (SEQ ID NOs: 3 and 4), Tat fragment (GRKKRRQRRRPPQC, YGRKKRRQRRRPPQ, YGRKKRRQRRR, RKKRRQRRR) (SEQ ID NOs: 5-8), transportan (GWTLNSAGYLLKINLKALAALAKKIL, AGYLLGKINLKALAALAKKIL) (SEQ ID NOs: 9 and 10), amphiphilic model peptide (KLALKLALKAL-KAALKLA) (SEQ ID NO: 11), GE11 (YHWYGYTPQNVI) (SEQ ID NO: 12), GE11(7) (YHWYGY) (SEQ ID NO: 13), GE11(5) (YHWY) (SEQ ID NO: 14), PVEC (LLIILRRRIRKQAHAHSK) (SEQ ID NO: 15), K-FGF (AAVALLPAVLLALLAP) (SEQ ID NO: 16), Ku70 (VPMLKPMLKE) (SEQ ID NO: 17), muscarine receptor-activating peptide (YTWYTP, YSWYTP, HWHTP, YHRHTP, NAYTWYTPEWHTPA) (SEQ ID NOs: 18-22), SAP (VRLPPPVRLPPPVRLPPP) (SEQ ID NO: 23), MMP-1 inhibitory peptide (VTYGNP, VTVGNP) (SEQ ID NOs: 24 and 25), Pep-1 (KETWWETWWTEWS-QPKKKRKV) (SEQ ID NO: 26), Pep-7 (SDLWEMMMVSLACQY) (SEQ ID NO: 27), HN-1 (TSPLNIHNGQKL) (SEQ ID NO: 28) and the like. The aforementioned peptide is at least one selected from the group consisting of GE11(SEQ ID NO: 12), GE11(7) (SEQ ID NO: 13) and GE11(5) (SEQ ID NO: 14). The above-mentioned peptide sequences are each indicated using amino acid one letter codes and in the order from the N-terminus to the C-terminus.

A third form of the aforementioned bio-related substance is, for example, carbohydrate. The ssNc molecule of the present invention can improve, for example, delivery and introduction efficiency into a target cell and/or resistance to enzymatic degradation by having the aforementioned carbohydrate.

The aforementioned carbohydrate is not particularly limited, and includes, for example, monosaccharide, disaccharide, trisaccharide, tetrasaccharide, oligosaccharide, and polysaccharide. More specifically, the aforementioned monosaccharide includes, for example, fructose, galactose, glucose, mannose, galactosamine, glucosamine, N-acetylglucosamine, N-acetylgalactosamine, glycerol and the like, the aforementioned disaccharide includes, for example, sucrose, lactose, maltose and the like, the aforementioned trisaccharide includes, for example, raffinose, maltotriose and the like, the aforementioned tetrasaccharide includes, for example, acarbose, stachyose and the like, the aforementioned oligosaccharide includes, for example, galactooligosaccharide, mannanoligosaccharide and the like, and the aforementioned polysaccharide includes, for example, cellulose, glycogen, hyaluronic acid, chitosan and the like. In addition, the aforementioned carbohydrate is at least one selected from the group consisting of lactose, N-acetylglucosamine and N-acetylgalactosamine.

The aforementioned monosaccharide may be an isomer such as stereoisomer, conformational isomer and the like, and may be substituted by amino group, alcohol, thiol and the like. The above-mentioned description can similarly apply to the aforementioned disaccharide, trisaccharide, tetrasaccharide, oligosaccharide and polysaccharide.

Other forms of the aforementioned bio-related substance include, for example, polyethylene glycol (PEG), polyamine, fluorescence molecule, biotin, intercalator molecule, water-soluble vitamin, metal chelating agent, cross-linking agent and the like.

In the ssNc molecule of the present invention, the number of the aforementioned bio-related substance is not particularly limited and it is, for example, 1-4, preferably, 1-3, more preferably, 1 or 2.

When the ssNc molecule of the present invention contains two or more bio-related substances mentioned above, the combination thereof is not particularly limited and, for example, only one kind may be used or a combination of not less than two different kinds.

In the ssNc molecule of the present invention, the binding sites of the aforementioned bio-related substance are, as mentioned above, the 5'-terminus, 3'-terminus, the aforementioned linker region (Lx) of the aforementioned nucleic acid molecule.

In the ssNc molecule of the present invention, the aforementioned bio-related substance may be bonded at one site or not less than two sites.

In the ssNc molecule of the present invention, the aforementioned bio-related substance may be, for example, directly or indirectly bonded to the aforementioned nucleic acid molecule, preferably indirectly. When indirectly bonded, for example, binding via a binding linker is preferable. The structure of the aforementioned binding linker is not particularly limited and, for example, GMBS linker, ethylene glycol linker, or the structure of the following formula can be mentioned. In the following formula, n' is a positive integer, Y is, for example, NH, S, O, CO and the like. In the ssNc molecule of the present invention, when the aforementioned bio-related substance has an amino acid such as cysteine and the like, for example, the aforementioned bio-related substance may be bonded to the aforementioned nucleic acid molecule via a disulfide bond.

[Chem. 2]

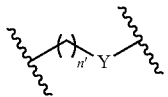

One embodiment of the nucleic acid structure of the ssNc molecule of the present invention is shown by the schematic view of FIG. 1. As one embodiment, FIG. 1A is a schematic view showing the order of the respective regions in the aforementioned ssNc molecule. FIG. 1B is a schematic view showing the state where double strands are formed in the aforementioned ssNc molecule. As shown in FIG. 1B, in the aforementioned ssNc molecule, a double strand is formed between the aforementioned region (Xc) and the aforementioned region (X), the aforementioned Lx region forms a loop structure according to the length thereof. The schematic views shown in FIG. 1 merely illustrates the order in which the aforementioned regions are linked and the positional relationship of the respective regions forming the double strand, and they do not limit, for example, the lengths of the respective regions, the shape of the aforementioned linker region (Lx), and the like.

In the ssNc molecule of the present invention, the aforementioned bio-related substance may be bonded to, as mentioned above, for example, any of an unbound terminal of the aforementioned region (Xc), an unbound terminal of the aforementioned region (X), and linker region (Lx) in FIG. 1.

In the ssNc molecule of the present invention, the base number of the aforementioned region (Xc) and the aforementioned region (X) is not particularly limited and it is, for example, as described below. In the present invention, "the number of bases" means the "length", for example, and it can also be referred to as the "base length".

As described above, for example, the aforementioned region (Xc) may be complementary to the entire region of the aforementioned region (X). In this case, it is preferable that, for example, the aforementioned region (Xc) has the same base length as the aforementioned region (X), and is composed of a base sequence complementary to the entire region of from the 5'-terminus to the 3'-terminus of the aforementioned region (X). It is more preferable that the aforementioned region (Xc) has the same base length as the aforementioned region (X) and all the bases in the aforementioned region (Xc) are complementary to all the bases in the aforementioned region (X), i.e., for example, preferably, the region (Xc) is perfectly complementary to the region (X). It is to be noted, however, that the configuration of the region (Xc) is not limited thereto, and one or a few bases in the region (Xc) may be noncomplementary to the corresponding bases in the region (X), for example, as described above.

Furthermore, as described above, the aforementioned region (Xc) may be complementary to, for example, a part of the aforementioned region (X). In this case, it is preferable that, for example, the aforementioned region (Xc) has the same base length as the part of the aforementioned region (X), i.e., the aforementioned region (Xc) is composed of a base sequence whose base length is shorter than the base length of the aforementioned region (X) by one or more bases. It is more preferable that the aforementioned region (Xc) has the same base length as the part of the aforementioned region (X) and all the bases in the aforementioned region (Xc) are complementary to all the bases in the part of the aforementioned region (X), i.e., for example, preferably, the region (Xc) is perfectly complementary to the part of the region (X). The part of the aforementioned region (X) is preferably a region (segment) having a base sequence composed of, for example, successive bases starting from the base at the 5'-terminus (the 1st base) in the aforementioned region (X).

In the ssNc molecule of the present invention, the relationship between the base number (X) of the aforementioned region (X) and the base number (Xc) of the aforementioned region (Xc) satisfies, for example, the conditions of the following expressions (1) or (2). In the former case, it specifically satisfies, for example, the following condition (3).

$$X > Xc \qquad (1)$$

$$X - Xc = 1\text{-}10, \text{ preferably } 1, 2 \text{ or } 3,$$

$$\text{more preferably } 1 \text{ or } 2 \qquad (3)$$

$$X = Xc \qquad (2)$$

While the length of each region of the ssNc molecule of the present invention is shown below, the present invention is not limited thereto. In the present invention, for example, the numerical range of the base number discloses all positive integers that fall within the range and, for example, "1-4 bases" means all of "1, 2, 3, 4 bases" (hereinafter the same).

The number of the bases in the aforementioned region (X) is, for example, 19 or more. The lower limit of the number of the bases is, for example, 19, preferably 20, and more preferably 21. The upper limit of the number of the aforementioned bases is, for example, 50, preferably 40, and more preferably 30.

When the aforementioned region (X) includes the aforementioned expression inhibitory sequence, the aforementioned region (X) may be, for example, a region composed of the aforementioned expression inhibitory sequence only or a region including the aforementioned expression inhibitory sequence. The number of bases of the aforementioned expression inhibitory sequence is, for example, 19 to 30, preferably 19, 20, or 21. When the aforementioned region (X) includes the aforementioned expression inhibitory sequence, the aforementioned expression inhibitory sequence further may have an additional sequence on its 5' side and/or 3' side. The number of bases in the aforementioned additional sequence is, for example, 1 to 31, preferably 1 to 21, more preferably 1 to 11, and still more preferably 1 to 7.

When the aforementioned region (Xc) includes the aforementioned expression inhibitory sequence, the aforementioned region (Xc) may be, for example, a region composed of the aforementioned expression inhibitory sequence only or a region including the aforementioned expression inhibitory sequence. For example, the length of the aforementioned expression inhibitory sequence is as described above. When the aforementioned region (Xc) includes the aforementioned expression inhibitory sequence, the aforementioned expression inhibitory sequence further may have an additional sequence on its 5' side and/or 3' side. The number of bases in the aforementioned additional sequence is, for example, 1 to 11, preferably 1 to 7.

In the ssNc molecule of the present invention, the length of the aforementioned linker region (Lx) is not particularly limited. The aforementioned linker region (Lx) preferably has a length permitting, for example, the aforementioned region (X) and the aforementioned region (Xc) to form a double strand. As for the base number of the aforementioned linker region (Lx), the lower limit of the number of bases is, for example, 1, preferably 2, and more preferably 3, and the upper limit of the same is, for example, 100, preferably 80, and more preferably 50. The number of bases in each of the aforementioned linker regions is specifically 1 to 50, 1 to 30, 1 to 20, 1 to 10, 1 to 7, or 1 to 4, for example, but it is not limited to these examples.

The full length of the ssNc molecule of the present invention is not particularly limited. In the ssNc molecule of the present invention, the lower limit of the total number of bases (the number of bases in the full length), is, for example, 38, preferably 42, more preferably 50, still more preferably 51, and particularly preferably 52, and the upper limit of the same is, for example, 300, preferably 200, more preferably 150, still more preferably 100, and particularly preferably 80. In the ssNc molecule of the present invention, the lower limit of the total number of bases excluding that in the aforementioned linker region (Lx) is, for example, 38, preferably 42, more preferably 50, still more preferably 51, and particularly preferably 52, and the upper limit of the same is, for example, 300, preferably 200, more preferably 150, still more preferably 100, and particularly preferably 80.

In the ssNc molecule of the present invention, the constitutional units are not particularly limited. Examples thereof include nucleotide residues. Examples of the aforementioned nucleotide residues include a ribonucleotide residue and a deoxyribonucleotide residue. The aforementioned nucleotide residue may be, for example, the one that is not modified (unmodified nucleotide residue) or the one that has been modified (modified nucleotide residue). By configuring the ssNc molecule of the present invention to include the aforementioned modified nucleotide residue, for example, the resistance of the ssNc molecule to nuclease can be improved, thereby allowing the stability of the ssNc molecule to be improved. Furthermore, the ssNc molecule of the present invention further may include, for example, a non-nucleotide residue in addition to the aforementioned nucleotide residue. The detail of the aforementioned nucleotide residue and the aforementioned non-nucleotide residue is described later.

In the ssNc molecule of the present invention, the constitutional unit of each of the aforementioned region (X) and the aforementioned region (Xc) is preferably the aforementioned nucleotide residue. Each of the aforementioned regions is composed of, for example, any of the following residues (1) to (3):
(1) an unmodified nucleotide residue(s)
(2) a modified nucleotide residue(s)
(3) an unmodified nucleotide residue(s) and a modified nucleotide residue(s).

In the ssNc molecule of the present invention, the constitutional units of the aforementioned linker region (Lx) are not particularly limited, and examples thereof include the aforementioned nucleotide residues and the aforementioned non-nucleotide residues. Each of the aforementioned linker regions may be composed of, for example, the aforementioned nucleotide residue(s) only, the aforementioned non-nucleotide residue(s) only, or both the aforementioned nucleotide residue(s) and the aforementioned non-nucleotide residue(s). Each of the aforementioned linker regions is composed of, for example, any of the following residues (1) to (7):
(1) an unmodified nucleotide residue(s)
(2) a modified nucleotide residue(s)
(3) an unmodified nucleotide residue(s) and a modified nucleotide residue(s)
(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s).

Examples of the ssNc molecule of the present invention include molecules composed of the aforementioned nucleotide residues only; and molecules including the aforementioned non-nucleotide residue(s) in addition to the aforementioned nucleotide residues. In the ssNc molecule of the present invention, for example, the aforementioned nucleotide residues may be the aforementioned unmodified nucleotide residues only; the aforementioned modified nucleotide residues only; or both the aforementioned unmodified nucleotide residue(s) and the aforementioned modified nucleotide residue(s), as described above. When the aforementioned ssNc molecule includes both the aforementioned unmodified nucleotide residue(s) and the aforementioned modified nucleotide residue(s), the number of the aforementioned modified nucleotide residue(s) is not particularly limited, and is, for example, "one to several", specifically, for example, 1 to 5, preferably 1 to 4, more preferably 1 to 3, and most preferably 1 or 2. When the ssNc molecule of the present invention include the aforementioned non-nucleotide residue(s), the number of the aforementioned non-nucleotide residue(s) is not particularly limited, and is, for example, "one to several", specifically, for example, 1 to 8, 1 to 6, 1 to 4, 1, 2 or 3.

In the ssNc molecule of the present invention, for example, the aforementioned nucleotide residue is preferably a ribonucleotide residue. In this case, for example, the ssNc molecule of the present invention also is referred to as an "RNA molecule" or "ssRNA molecule". Examples of the aforementioned ssRNA molecule include molecules composed of the aforementioned ribonucleotide residues only; and a molecule including the aforementioned non-nucleotide residue(s) in addition to the aforementioned ribonucleotide residues. As described above, as the aforementioned ribonucleotide residues, for example, the aforementioned ssRNA molecule may include: the aforementioned unmodified ribonucleotide residues only; the aforementioned modified ribonucleotide residues only; or both the aforementioned unmodified ribonucleotide residue(s) and the aforementioned modified ribonucleotide residue(s).

When the aforementioned ssRNA molecule includes, for example, the aforementioned modified ribonucleotide residue(s) in addition to the aforementioned unmodified ribonucleotide residues, the number of the aforementioned modified ribonucleotide residue(s) is not particularly limited, and is, for example, "one to several", specifically, for example, 1 to 5, preferably 1 to 4, more preferably 1 to 3, and most preferably 1 or 2. The aforementioned modified ribonucleotide residue as contrasted to the aforementioned unmodified ribonucleotide residue may be, for example, the aforementioned deoxyribonucleotide residue obtained by substituting a ribose residue with a deoxyribose residue. When the aforementioned ssRNA molecule includes, for example, the aforementioned deoxyribonucleotide residue(s) in addition to the aforementioned unmodified ribonucleotide residue(s), the number of the aforementioned deoxyribonucleotide residue(s) is not particularly limited, and is, for example, "one to several", specifically, for example, 1 to 5, preferably 1 to 4, more preferably 1 to 3, and most preferably 1 or 2.

In the ssNc molecule of the present invention, the aforementioned linker region (Lx) may contain a non-nucleotide residue and may contain, for example, a non-nucleotide residue represented by the following formula (I):

[Chem. I]

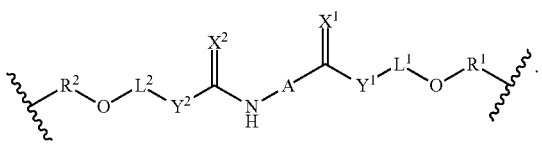

(I)

In the aforementioned formula (I), for example,
$X^1$ and $X^2$ are each independently $H_2$, O, S, or NH;
$Y^1$ and $Y^2$ are each independently a single bond, $CH_2$, NH, O, or S;

$L^1$ is an alkylene chain having n carbon atoms, and a hydrogen atom on an alkylene carbon atom may or may not be substituted
with OH, $OR^a$, $NH_2$, $NHR^a$, $NR^aR^b$, SH, or $SR^a$, or,
$L^1$ is a polyether chain obtained by substituting at least one carbon atom on the aforementioned alkylene chain with an oxygen atom,
provided that: when $Y^1$ is NH, O, or S, an atom bound to $Y^1$ in $L^1$ is carbon, an atom bound to $OR^1$ in $L^1$ is carbon, and oxygen atoms are not adjacent to each other;
$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or
$L^2$ is a polyether chain obtained by substituting at least one carbon atom on the aforementioned alkylene chain with an oxygen atom,
provided that: when $Y^2$ is NH, O, or S, an atom bound to $Y^2$ in $L^2$ is carbon, an atom bound to $OR^2$ in $L^2$ is carbon, and oxygen atoms are not adjacent to each other;
$R^a$, $R^b$, $R^c$, and $R^d$ are each independently a substituent or a protecting group;
m is an integer in the range from 0 to 30;
n is an integer in the range from 0 to 30;
the aforementioned regions (Xc) and (X) are each linked to the aforementioned linker region (Lx) via —$OR^1$— or —$OR^2$—,
wherein $R^1$ and $R^2$ may or may not be present, and when they are present, $R^1$ and $R^2$ are each independently a nucleotide residue or the aforementioned structure (I); and
A is any atomic group, the following formula (Ia) is the aforementioned amino acid, and the following formula (Ia) is an amino acid other than peptide:

[Chem. Ia]

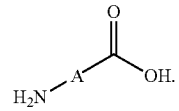

(Ia)

In the aforementioned formula (I), for example, $X^1$ and $X^2$ are each independently $H_2$, O, S, or NH. In the aforementioned formula (I), "$X^1$ is $H_2$" means that $X^1$ forms $CH_2$ (a methylene group) together with a carbon atom to which $X^1$ binds. The same applies to $X^2$.

In the aforementioned formula (I), $Y^1$ and $Y^2$ are each independently a single bond, $CH_2$, NH, O, or S.

In the aforementioned formula (I), $L^1$ is an alkylene chain having n carbon atoms. A hydrogen atom(s) on the aforementioned alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the aforementioned alkylene chain with an oxygen atom. The aforementioned polyether chain is, for example, polyethylene glycol. When $Y^1$ is NH, O, or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the aforementioned formula (I), $L^2$ is an alkylene chain having m carbon atoms. A hydrogen atom(s) on the aforementioned alkylene carbon atom(s) may or may not be substituted with, for example, OH, $OR^c$, $NH_2$, $NHR^c$, $NR^cR^d$, SH, or $SR^c$. Alternatively, $L^2$ may be a polyether chain obtained by substituting at least one carbon atom on the aforementioned alkylene chain with an oxygen atom. When $Y^2$ is NH, O, or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. For example, n and m can be set as appropriate depending on a desired length of the aforementioned linker region (Lx). For example, from the view point of manufacturing cost, yield, and the like, n and m are each preferably 0 to 30, more preferably to 20, and still more preferably 0 to 15. n and m may be the same (n=m) or different. n+m is, for example, 0 to 30, preferably 0 to 20, and more preferably 0 to 15.

For example, $R^a$, $R^b$, $R^c$ and $R^d$ are each independently a substituent or a protecting group, and may be the same or different. Examples of the aforementioned substituent include hydroxy, carboxy, sulfo, halogen, alkyl halide (haloalkyl, e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryl (e.g., phenyl, naphthyl), arylalkyl (e.g., benzyl, phenethyl), alkylaryl (e.g., p-methylphenyl), heteroaryl (e.g., pyridyl, furyl), heteroarylalkyl (e.g., pyridylmethyl), heterocyclyl (e.g., piperidyl), heterocyclylalkenyl, heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino [alkylamino (e.g., methylamino, ethylamino, dimethylamino), acylamino (e.g., acetylamino, benzoylamino), arylalkylamino (e.g., benzylamino, tritylamino), hydroxyamino], aminoalkyl (e.g., aminomethyl), alkylaminoalkyl (e.g., diethylaminomethyl), carbamoyl, sulfamoyl, oxo, silyl, silyloxyalkyl and the like. These substituents are optionally substituted by one or more further substituents or further protecting groups. While the aforementioned further substituent is not particularly limited, for example, it may be a substituent exemplified above. The aforementioned further protecting group is not particularly limited and, for example, it may be a protecting group exemplified below. Hereinafter the same.

The aforementioned protecting group (or the aforementioned further protecting group) is a functional group that inactivates, for example, a highly-reactive functional group. Examples of the protecting group include known protecting groups. Regarding the aforementioned protecting group, for example, the description in the literature (J. F. W. McOmie, "Protecting Groups in Organic Chemistry", Plenum Press, London and New York, 1973) can be incorporated herein. The aforementioned protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), and a dimethoxytrityl group (DMTr). When $R^3$ is $OR^4$, the aforementioned protecting group is not particularly limited, and examples thereof include a TBDMS group, an ACE group, a TOM group, a CEE group, a CEM group, and a TEM group. Other examples of the protecting group include silyl-containing groups represented by the chemical formulae (P1) and (P2) to be shown later. The same applies hereinafter.

In the aforementioned formula (I), hydrogen atoms each independently may be substituted with, for example, a halogen such as Cl, Br, F, or I.

The aforementioned regions (Xc) and (X) are each linked, for example, to the aforementioned linker region (Lx) via $—OR^1—$ or $—OR^2—$. $R^1$ and $R^2$ may or may not be present. When $R^1$ and $R^2$ are present, $R^1$ and $R^2$ are each independently a nucleotide residue or the structure represented by the aforementioned formula (I). When $R^1$ and/or $R^2$ are/is the aforementioned nucleotide residue, the aforementioned linker region (Lx) is composed of, for example, the aforementioned non-nucleotide residue having the structure of the aforementioned formula (I) excluding the nucleotide residue $R^1$ and/or $R^2$, and the aforementioned nucleotide residue(s). When $R^1$ and/or $R^2$ are/is the structure represented by the aforementioned formula (I), the structure of the aforementioned linker region (Xc) is such that, for example, two or more of the aforementioned non-nucleotide residues having the structure of the aforementioned formula (I) are linked to each other. The number of the structures of the aforementioned formula (I) may be, for example, 1, 2, 3, or 4. When the linker region (Lx) includes a plurality of the aforementioned structures, the structures of the aforementioned (I) may be linked, for example, either directly or via the aforementioned nucleotide residue(s). On the other hand, when $R^1$ and $R^2$ are not present, the aforementioned linker region (Lx) is composed of, for example, the aforementioned non-nucleotide residue having the structure of the aforementioned formula (I) alone.

The combination of the aforementioned regions (Xc) and (X) with $—OR^1—$ and $—OR^2—$ is not particularly limited, and may be, for example, any of the following conditions.
Condition (1):
the aforementioned regions (Xc) and (X) are linked to the structure of the aforementioned formula (I) via $—OR^2—$ and $—OR^1—$, respectively.
Condition (2):
the aforementioned regions (Xc) and (X) are linked to the structure of the aforementioned formula (I) via $—OR^1—$ and $—OR^2—$, respectively.

In the ssNc molecule of the present invention, the atomic group A in the aforementioned formula (I) is not particularly limited and is optional; however, it is an amino acid represented by the following formula (Ia), which is not a peptide, as mentioned above.

[Chem. Ia]

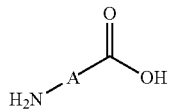

(Ia)

The atomic group A in the aforementioned formula (I), (IA) or (Ia) may or may not contain, for example, at least one selected from the group consisting of chain atomic group, alicyclic atomic group, and aromatic atomic group. While the aforementioned chain atomic group is not particularly limited, for example, alkyl, alkenyl, alkynyl, haloalkyl, hydroxyalkyl, alkoxyalkyl, aminoalkyl, silyl, silyloxyalkyl and the like can be mentioned. While the aforementioned alicyclic atomic group is not particularly limited, for example, cycloalkyl, cycloalkenyl, cycloalkylalkyl, cyclylalkyl and the like can be mentioned. While the aforementioned aromatic atomic group is not particularly limited, for example, aryl, arylalkyl, alkylaryl, condensed-ring aryl, condensed-ring arylalkyl, condensed-ring alkylaryl and the like can be mentioned. In the atomic group A in the aforementioned formula (I), (IA) or (Ia), each of the aforementioned atomic groups may or may not further have a substituent or a protecting group. When the aforementioned substituent or protecting group is in plurality, they may be the same or different. The aforementioned substituents are, for example, those exemplified for the aforementioned $R^a$, $R^b$, $R^c$ and $R^d$, more specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The aforementioned protecting groups are, for example, the same as those exemplified for the aforementioned $R^a$, $R^b$, $R^c$ and $R^d$.

In the present invention, the "amino acid" refers to any organic compound containing at least one amino group and at least one carboxy group in a molecule. The "peptide" refers to an organic compound having a structure wherein not less than 2 molecules of amino acid are bonded via a peptide bond. The aforementioned peptide bond may be an acid amide structure or an acid imide structure. When plural amino groups are present in the amino acid molecule represented by the aforementioned formula (Ia), the amino group clearly shown in the aforementioned formula (Ia) may be any amino group. In addition, when plural carboxy groups are present in the amino acid molecule represented by the aforementioned formula (Ia), the carboxy group clearly shown in the aforementioned formula (Ia) may be any carboxy group.

In the aforementioned linker region of the single-stranded nucleic acid of the present invention, the aforementioned amino acid may be, for example, natural amino acid or artificial amino acid. In the present invention, the "natural amino acid" refers to an amino acid having a naturally-occurring structure or an optical isomer thereof. The production method of the aforementioned natural amino acid is not particularly limited and, for example, it may be extracted from the nature, or may be synthesized. In the present invention, moreover, the "artificial amino acid" refers to an amino acid having a structure not occurring naturally. That is, the aforementioned artificial amino acid is an amino acid, i.e., a carboxylic acid derivative containing an amino group (organic compound containing at least one amino group and at least one carboxy group in a molecule) and having a structure not occurring naturally. The aforementioned artificial amino acid preferably does not contain, for example, a hetero ring. The aforementioned amino acid may be, for example, an amino acid constituting a protein. The aforementioned amino acid may be, for example, glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, tryptophan, β-alanine, 1-amino-2-carboxycyclopentane, or aminobenzoic acid, and may or may not further have a substituent or a protecting group.

Examples of the aforementioned substituent include the substituents exemplified for the aforementioned $R^a$, $R^b$, $R^c$ and $R^d$. More specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like can be mentioned. The aforementioned protecting group is the same as, for example, the protecting groups exemplified for the aforementioned $R^a$, $R^b$, $R^c$ and $R^d$. When the amino acid of the aforementioned formula (Ia), which is not peptide, contains isomers such as optical isomer, geometric isomer, stereoisomer and the like, any isomer can be used.

Examples of the structure of the aforementioned formula (I) include the structures of the following formulae (I-1) to (I-4). In the following formulae, n and m are the same as in the aforementioned formula (I).

[Chem. I-1]

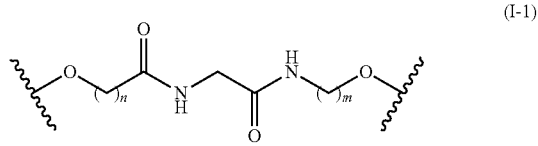

(I-1)

[Chem. I-2]

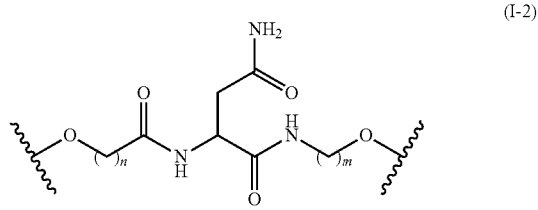

(I-2)

[Chem. I-3]

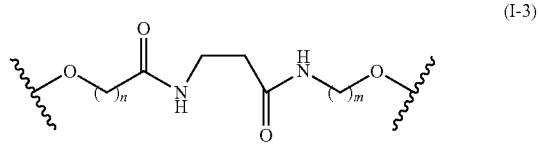

(I-3)

[Chem. I-4]

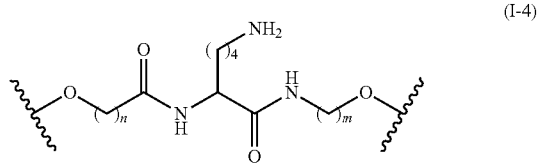

(I-4)

In the aforementioned formulae (I-1) to (I-4), n and m are as described above. Specific example thereof is the aforementioned formula (I-1) wherein n=11 and m=12. The structure thereof is shown by the following formula (I-1a). Another specific example is the aforementioned formula (I-1) wherein n=5 and m=4. The structure thereof is shown by the following formula (I-1b). Still another specific example is the aforementioned formula (I-4) wherein n=5 and m=4. The structure thereof is shown by the following formula (I-4a).

[Chem. I-1a]

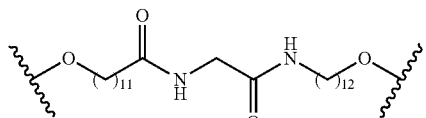

(I-1a)

[Chem. I-1b]

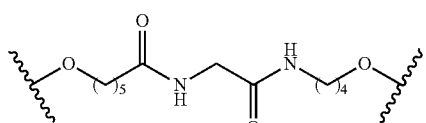

(I-1b)

[Chem. I-4a]

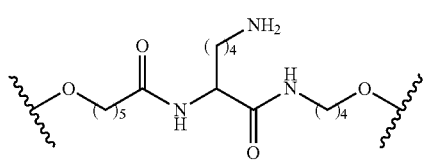

(I-4a)

In the ssNc molecule of the present invention, the aforementioned linker region (Lx) may contain, for example, lysine-cholesterol represented by the following formula:

[Chem. 3]

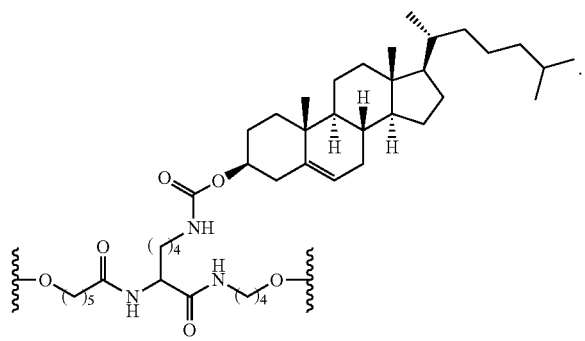

The ssNc molecule of the present invention may include, for example, a labeling substance, and may be labeled with the aforementioned labeling substance. The aforementioned labeling substance is not particularly limited, and may be, for example, a fluorescent substance, a dye, an isotope, or the like. Examples of the aforementioned labeling substance include: fluorophores such as pyrene, TAMRA, fluorescein, a Cy3 dye, and a Cy5 dye. Examples of the aforementioned dye include Alexa dyes such as Alexa 488. Examples of the aforementioned isotope include stable isotopes and radioisotopes. Among them, stable isotopes are preferable. For example, the aforementioned stable isotopes have a low risk of radiation exposure and they require no dedicated facilities. Thus, stable isotopes are excellent in handleability and can contribute to cost reduction. Moreover, for example, the aforementioned stable isotope does not change the physical properties of a compound labeled therewith and thus has an excellent property as a tracer. The aforementioned stable isotope is not particularly limited, and examples thereof include $^{2}H$, $^{13}C$, $^{15}N$, $^{17}O$, $^{18}O$, $^{33}S$, $^{34}S$, and $^{36}S$.

As described above, the ssNc molecule of the present invention can inhibit the aforementioned expression of a target gene. Thus, the ssNc molecule of the present invention can be used, for example, as a therapeutic agent for treating a disease caused by a gene. When the ssNc molecule of the present invention includes, for example, as the aforementioned expression inhibitory sequence, a sequence that inhibits expression of a gene causing the aforementioned disease, for example, it is possible to treat the aforementioned disease by inhibiting the expression of the aforementioned target gene. In the present invention, the term "treatment" encompasses: prevention of the aforementioned diseases; improvement of the diseases; and improvement in prognosis, for example, and it can mean any of them.

The method of using the ssNc molecule of the present invention is not particularly limited. For example, the aforementioned ssNc molecule may be administered to a subject having the aforementioned target gene.

Examples of the aforementioned subject to which the ssNc molecule of the present invention is administered include cells, tissues, organs and the like. Examples of the aforementioned subject also include humans, nonhuman animals and the like such as nonhuman mammals, i.e., mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

In the present invention, the aforementioned target gene whose expression is to be inhibited is not particularly limited, and any desired gene can be set to the target gene. Furthermore, as mentioned above, the aforementioned expression inhibitory sequence may be designed as appropriate depending on the kind of the aforementioned target gene.

As to the use of the ssNc molecule of the present invention, the following description regarding the composition, the expression inhibitory method, the treatment method, and the like according to the present invention to be describe below can be referred to.

Since the ssNc molecule of the present invention can inhibit the expression of a target gene as described above, for example, it is useful as a pharmaceutical product, a diagnostic agent, an agricultural chemical, and a tool for conducting research on the agricultural chemical, medical science, life science, and the like.

2. Nucleotide Residue

The aforementioned nucleotide residue includes, for example, a sugar, a base, and a phosphate as its components. The aforementioned nucleotide residue may be, for example, a ribonucleotide residue or a deoxyribonucleotide residue, as described above. The aforementioned ribonucleotide residue has, for example, a ribose residue as the sugar; and adenine (A), guanine (G), cytosine (C), or uracil (U) as the base. The aforementioned deoxyribose residue has, for example, a deoxyribose residue as the sugar; and adenine (A), guanine (G), cytosine (C), or thymine (T) as the base.

The aforementioned nucleotide residue may be, for example, an unmodified nucleotide residue or a modified nucleotide residue. The aforementioned components of the aforementioned unmodified nucleotide residue are the same or substantially the same as, for example, the components of a naturally-occurring nucleotide residue. Preferably, the components are the same or substantially the same as the components of a nucleotide residue occurring naturally in a human body.

The aforementioned modified nucleotide residue is, for example, a nucleotide residue obtained by modifying the aforementioned unmodified nucleotide residue. For example, the aforementioned modified nucleotide residue may be such that any of the components of the aforementioned unmodified nucleotide residue is modified. In the present invention, "modification" means, for example, substitution, addition, and/or deletion of any of the aforementioned components; and substitution, addition, and/or deletion of an atom (s) and/or a functional group(s) in the aforementioned component(s). It can also be referred to as "modification". Examples of the aforementioned modified nucleotide residue include naturally-occurring nucleotide residues and artificially-modified nucleotide residues. Regarding the aforementioned naturally-derived modified nucleotide residues, for example, Limbach et al. (Limbach et al., 1994, Summary: the modified nucleosides of RNA, Nucleic Acids Res. 22: pp. 2183 to 2196) can be referred to. The aforementioned modified nucleotide residue may be, for example, a residue of an alternative of the aforementioned nucleotide.

Examples of the modification of the aforementioned nucleotide residue include modification of a ribose-phosphate backbone (hereinafter referred to as a "ribophosphate backbone").

In the aforementioned ribophosphate backbone, for example, a ribose residue may be modified. In the aforementioned ribose residue, for example, the 2'-position carbon can be modified. Specifically, a hydroxyl group bound to, for example, the 2'-position carbon can be substituted with hydrogen or halogen such as fluoro. By substituting the hydroxyl group bound to the aforementioned 2'-position carbon with hydrogen, it is possible to substitute the ribose residue with deoxyribose. The aforementioned ribose residue can be substituted with its stereoisomer, for example, and may be substituted with, for example, an arabinose residue.

The aforementioned ribophosphate backbone may be substituted with, for example, a non-ribophosphate backbone having a non-ribose residue and/or a non-phosphate. The aforementioned non-ribophosphate backbone may be, for example, the aforementioned ribophosphate backbone modified to be uncharged. Examples of an alternative obtained by substituting the ribophosphate backbone with the aforementioned non-ribophosphate backbone in the aforementioned nucleotide include morpholino, cyclobutyl, and pyrrolidine. Other examples of the aforementioned alternative include artificial nucleic acid monomer residues. Specific examples thereof include PNA (Peptide Nucleic Acid), LNA (Locked Nucleic Acid), and ENA (2'-0,4'-C-Ethylenebridged Nucleic Acids). Among them, PNA is preferable.

In the aforementioned ribophosphate backbone, for example, a phosphate group can be modified. In the aforementioned ribophosphate backbone, a phosphate group in the closest proximity to the sugar residue is called an "α-phosphate group". The aforementioned α-phosphate group is charged negatively, and the electric charges are distributed evenly over two oxygen atoms that are not linked to the sugar residue. Among the four oxygen atoms in the aforementioned α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the aforementioned nucleotide residues hereinafter are referred to as "linking oxygens". For example, the aforementioned α-phosphate group is preferably modified to be uncharged, or to render the charge distribution between the aforementioned non-linking oxygens asymmetric.

In the aforementioned phosphate group, for example, the aforementioned non-linking oxygen(s) may be substituted. The aforementioned oxygen(s) can be substituted with, for example, any atom selected from S (sulfur), Se (selenium), B (boron), C (carbon), H (hydrogen), N (nitrogen), and OR (R is an alkyl group or an aryl group) and substitution with S is preferable. It is preferable that one of the non-linking oxygens is substituted with S, for example, and it is more preferable that both the aforementioned non-linking oxygens are substituted. Examples of the aforementioned modified phosphate group include phosphorothioates, phosphorodithioates, phosphoroselenates, borano phosphates, borano phosphate esters, hydrogen phosphonates, phosphoroamidates, alkyl or aryl phosphonates, and phosphotriesters. In particular, phosphorodithioate in which both of the aforementioned two non-linking oxygens are substituted with S is preferable.

In the aforementioned phosphate group, for example, the aforementioned linking oxygen(s) can be substituted. The aforementioned oxygen(s) can be substituted with, for example, any atom selected from S (sulfur), C (carbon), and N (nitrogen). Examples of the aforementioned modified phosphate group include: bridged phosphoroamidates resulting from the substitution with N; bridged phosphorothioates resulting from the substitution with S; and bridged methylenephosphonates resulting from the substitution with C. Preferably, substitution of the aforementioned linking oxygen(s) is performed in, for example, at least one of the 5'-terminus nucleotide residue and the 3'-terminus nucleotide residue of the ssNc molecule of the present invention. When the substitution is performed on the 5' side, substitution with C is preferable. When the substitution is performed on the 3' side, substitution with N is preferable.

The aforementioned phosphate group may be substituted with, for example, the aforementioned phosphate-free linker. The aforementioned linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylenecarbonylamino group and a methylenemethylimino group.

In the ssNc molecule of the present invention, for example, at least one of a nucleotide residue at the 3'-terminus and a nucleotide residue at the 5'-terminus may be modified. For example, the nucleotide residue at either one of the 3'-terminus and the 5'-terminus may be modified, or the nucleotide residues at both the 3'-terminus and the 5'-terminus may be modified. The aforementioned modification may be, for example, as described above, and it is preferable to modify a phosphate group(s) at the end(s). For example, the entire aforementioned phosphate group may be modified, or one or more atoms in the aforementioned phosphate group may be modified. In the former case, for example, the entire phosphate group may be substituted or deleted.

Modification of the aforementioned nucleotide residue(s) at the end(s) may be, for example, addition of any other molecule. Examples of the aforementioned other molecule include functional molecules such as labeling substances and protecting groups as described above. Examples of the aforementioned protecting groups include S (sulfur), Si (silicon), B (boron), and ester-containing groups. The functional molecules such as the aforementioned labeling substances can be used, for example, in the detection and the like of the ssNc molecule of the present invention.

The aforementioned other molecule may be, for example, added to the phosphate group of the aforementioned nucleotide residue or may be added to the aforementioned phosphate group or the aforementioned sugar residue via a spacer. For example, the terminal atom of the aforementioned spacer can be added to or substituted for either one of the aforementioned linking oxygens of the aforementioned phosphate group, or O, N, S, or C of the sugar residue. The binding site in the aforementioned sugar residue preferably is, for example, C at the 3'-position, C at the 5'-position, or any atom bound thereto. For example, the aforementioned spacer can also be added to or substituted for a terminal atom of the aforementioned nucleotide alternative such as PNA.

The aforementioned spacer is not particularly limited, and examples thereof include —$(CH_2)_n$—, —$(CH_2)_nN$—, —$(CH_2)_nO$—, —$(CH_2)_nS$—, —$O(CH_2CH_2O)_n$ $CH_2CH_2OH$, abasic sugars, amide, carboxy, amine, oxyamine, oxyimine, thioether, disulfide, thiourea, sulfonamide, and morpholino, and also biotin reagents and fluorescein reagents. In the aforementioned formulae, n is a positive integer, and n=3 or 6 is preferable.

Other examples of the aforementioned molecule to be added to the end include dyes, intercalating agents (e.g., acridines), crosslinking agents (e.g., psoralen, mitomycin C), porphyrins (TPPC4, texaphyrin, sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrenebutyric acid, dihydrotestosterone, 1,3-Bis-O (hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl)cholic acid, dimethoxytrityl, or phenoxathiine), peptide complexes (e.g., Antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), and synthetic ribonucleases (e.g., imidazole, bisimidazole, histamine, imidazole clusters, acridine-imidazole complexes, $Eu^{3+}$ complexes of tetraazamacrocycles).

In the ssNc molecule of the present invention, for example, the aforementioned 5'-teLminus may be modified with a phosphate group or a phosphate group analog. Examples of the aforementioned phosphate group include:
5'-monophosphate (($HO)_2(O)P$—O-5');
5'-diphosphate (($HO)_2(O)$ P—O—$P(HO)(O)$—O-5');
5'-triphosphate (($HO)_2$ (O)P—O—$(HO)(O)P$—O—$P(HO)(O)$—O-5');
5'-guanosine cap (7-methylated or non-methylated, 7 m-G-O-5'-(HO) (O)P—O—(HO)(O)P—O—P(HO)(O)—O-5');
5'-adenosine cap (Appp);
any modified or unmodified nucleotide cap structure (N—O-5'-(HO)(O)P—O—(HO)(O)P—O—P(HO)(O)—O-5');
5'-monothiophosphate (phosphorothioate: $(HO)_2(S)P$—O-5');
5'-monodithiophosphate (phosphorodithioate: (HO)(HS)(S)P—O-5');
5'-phosphorothiolate (($HO)_2(O)P$—S-5');
sulfur substituted monophosphate, diphosphate, and triphosphates (e.g., 5'-α-thiotriphosphate, 5'-γ-thiotriphosphate, and the like);
5'-phosphoramidates (($HO)_2(O)P$—NH-5', (HO) ($NH_2$)(O)P—O-5');
5'-alkylphosphonates (e.g., RP(OH)(O)—O-5', $(OH)_2(O)P$-5'-$CH_2$, where R is alkyl (e.g., methyl, ethyl, isopropyl, propyl, or the like)); and
5'-alkyletherphosphonates (e.g., RP(OH) (O)—O-5', where R is alkylether (e.g., methoxymethyl, ethoxymethyl, or the like)).

In the aforementioned nucleotide residue, the aforementioned base is not particularly limited. The aforementioned base may be, for example, a natural base or a non-natural base. The aforementioned base may be, for example, a naturally-derived base or a synthetic base. As the aforementioned base, for example, a common base, a modified analog thereof, and the like can be used.

Examples of the aforementioned base include: purine bases such as adenine and guanine; and pyrimidine bases such as cytosine, uracil, and thymine. Other examples of the aforementioned base include inosine, xanthine, hypoxanthine, nebularine, isoguanisine, and tubercidine. Examples of the aforementioned base also include: 2-aminoadenine, alkyl derivatives such as 6-methylated purine; alkyl derivatives such as 2-propylated purine; 5-halouracil and 5-halocytosine; 5-propynyluracil and 5-propynylcytosine; 6-azouracil, 6-azocytosine, and 6-azothymine; 5-uracil (pseudouracil), 4-thiouracil, 5-halouracil, 5-(2-aminopropyl)uracil, 5-aminoallyluracil; 8-halogenated, aminated, thiolated, thioalkylated, hydroxylated, and other 8-substituted purines; 5-trifluoromethylated and other 5-substituted pyrimidines; 7-methylguanine; 5-substituted pyrimidines; 6-azapyrimidines; N-2, N-6, and O-6 substituted purines (including 2-aminopropyladenine); 5-propynyluracil and 5-propynylcytosine; dihydrouracil; 3-deaza-5-azacytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazoles; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N4-acetylcytosine; 2-thiocytosine; N6-methyladenine; N6-isopentyladenine; 2-methylthio-N6-isopentenyladenine; N-methylguanine; and O-alkylated bases. Examples of the purines and pyrimidines include those disclosed in U.S. Pat. No. 3,687,808, "Concise Encyclopedia of Polymer Science and Engineering", pp. 858 to 859, edited by Kroschwitz J. I, John Wiley & Sons, 1990, and Englisch et al, Angewandte Chemie, International Edition, 1991, vol. 30, p. 613.

Other examples of the aforementioned modified nucleotide residue include those having no base, i.e., those having an abasic ribophosphate backbone. Furthermore, as the aforementioned modified nucleotide residue, for example, those described in U.S. Provisional Application No. 60/465,665 (filing date: Apr. 25, 2003) and International Application No. PCT/US04/07070 (filing date: Mar. 8, 2004) can be used and these documents are incorporated herein by reference.

3. Non-Nucleotide Residue

The aforementioned non-nucleotide residue is not particularly limited. The ssNc molecule of the present invention may have, as the aforementioned non-nucleotide residue, for example, a non-nucleotide structure containing an amino acid residue or a peptide residue. Examples of the amino acid composing the aforementioned amino acid residue or peptide residue include basic amino acid, acidic amino acid and the like. Examples of the aforementioned basic amino acid include lysine, arginine, histidine and the like. Examples of the aforementioned acidic amino acid include aspartic acid, glutamic acid and the like. The aforementioned non-nucleotide residue is preferably present at, for example, the aforementioned linker region (Lx).

In the single-stranded nucleic acid molecule of the present invention, a method for modifying the 5'-terminus, 3'-terminus, the aforementioned linker region (Lx) with the aforementioned bio-related substance is not particularly limited.

As a first embodiment of the modification method, for example, an example of the modification method of the 5'-terminus of the aforementioned nucleic acid molecule is shown, for example, in the following scheme 1.

scheme 1

[Chem. S1]

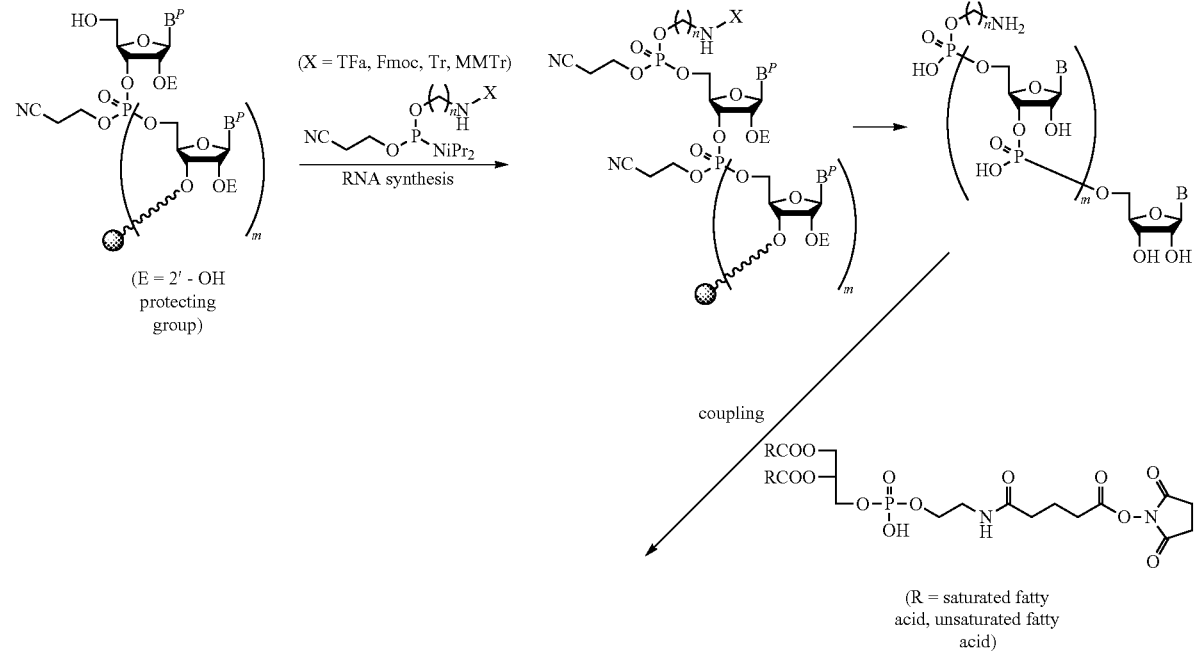

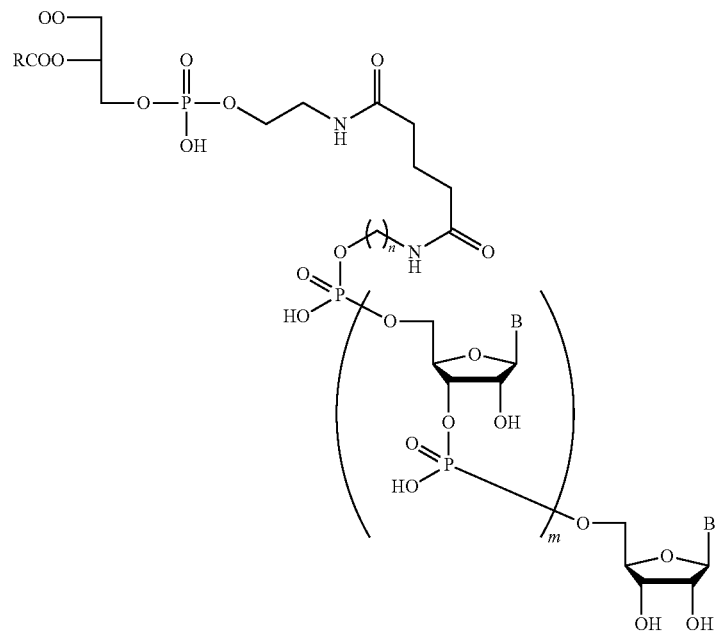

As a second embodiment of the modification method, for example, an example of the modification method of a linker region having an amino acid residue or peptide residue is shown below.

First, an amidite is synthesized by the synthesis method of the following scheme 2. The following scheme 2 is an example and the method is not limited thereto. For example, Fmoc is used as a protecting group of the amino group of the Lys side chain in the following scheme 2. However, for example, Tfa may be used as in scheme 6 in the below-mentioned Example, or other protecting group may also be used.

scheme 2

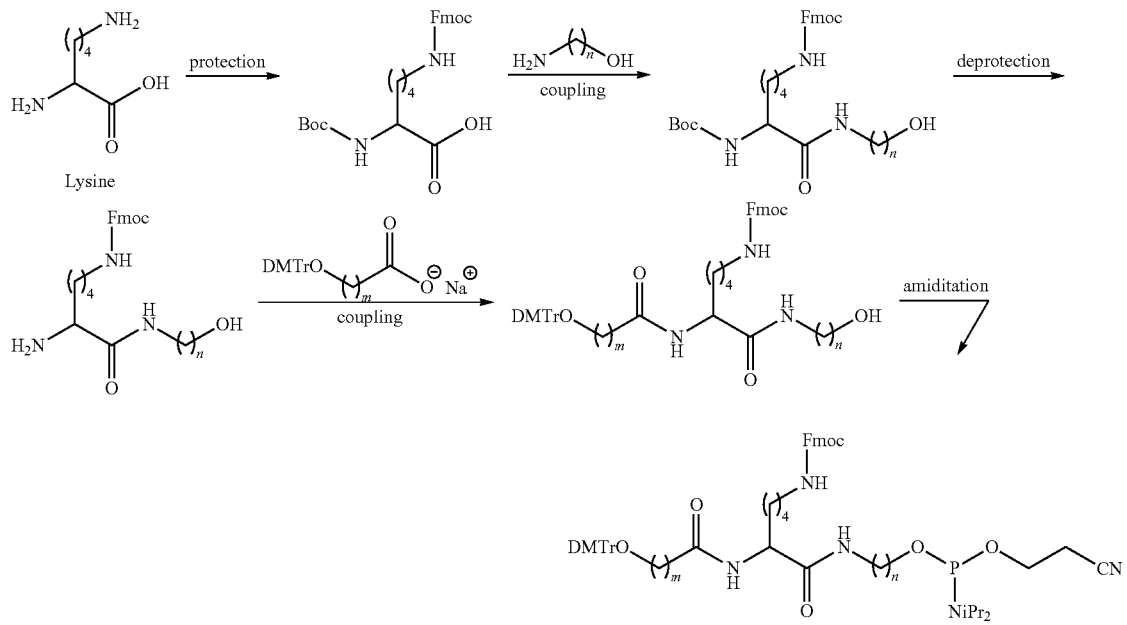

Then, using the aforementioned amidite having the aforementioned binding linker, and by the method of the following scheme 3, nucleic acid molecule is synthesized, and the aforementioned bio-related substance is linked to the aforementioned binding linker in the aforementioned nucleic acid molecule.

scheme 3

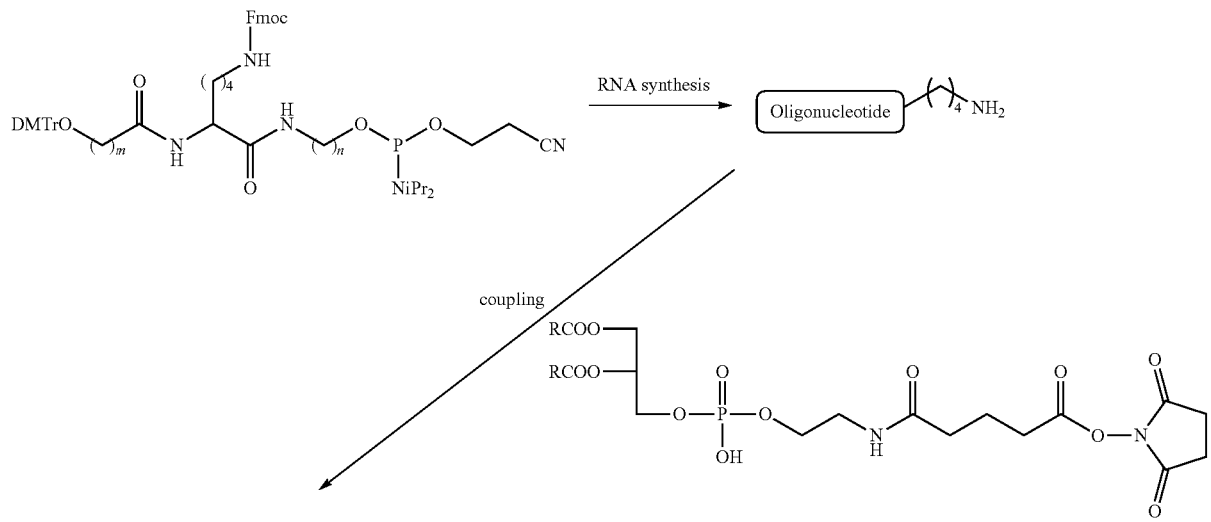

-continued

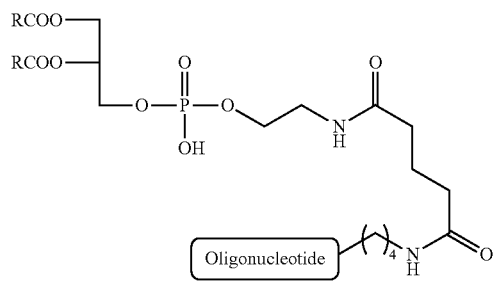

When a thiol linker is introduced as the aforementioned binding linker, the aforementioned nucleic acid molecule is synthesized by the synthesis method of the following scheme 4.

These methods are exemplifications and the present invention is not at all limited by these embodiments. For example, the aforementioned schemes 2 and 3 show one embodiment of the synthesis method when the aforemenscheme 4

[Chem. S4]

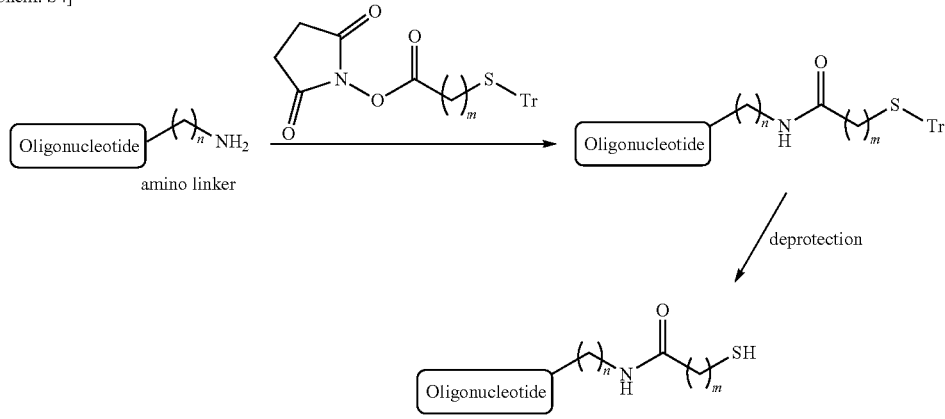

Then, as shown in the following scheme 5, the aforementioned bio-related substance is linked to the aforementioned thiol linker in the aforementioned nucleic acid molecule via an S—S bond.

tioned amino acid residue is a lysine residue. Even when the aforementioned amino acid residue or the aforementioned peptide residue has a structure derived from other amino acid, it can be synthesized in the same manner.

scheme 5

[Chem. S5]

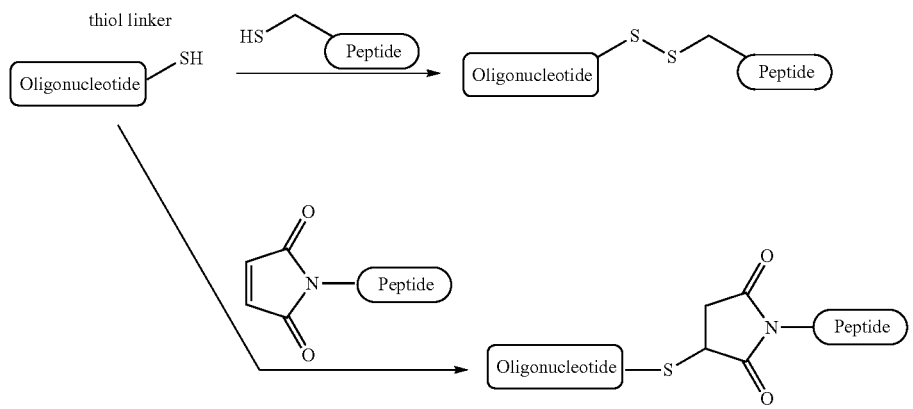

4. Composition

The expression inhibitory composition according to the present invention is, as described above, a composition for inhibiting the expression of a target gene, containing the aforementioned ssNc molecule of the present invention. The composition of the present invention is characterized in that it contains the aforementioned ssNc molecule of the present invention, and other configurations are by no means limited. The expression inhibitory composition of the present invention can also be referred to, for example, as an expression inhibitory reagent.

According to the present invention, for example, by administering to a subject in which the aforementioned target gene is present, it is possible to inhibit the expression of the aforementioned target gene.

Furthermore, as described above, the pharmaceutical composition according to the present invention contains the aforementioned ssNc molecule of the present invention. The composition of the present invention is characterized in that it contains the aforementioned ssNc molecule of the present invention, and other configurations are by no means limited. The pharmaceutical composition of the present invention can also be referred to, for example, as a pharmaceutical product.

According to the present invention, for example, administration to a patient with a disease caused by a gene can inhibit the expression of the aforementioned gene, thereby treating the aforementioned disease. In the present invention, the term "treatment" encompasses, as mentioned above, prevention of the aforementioned diseases; improvement of the diseases; and improvement in prognosis, for example, and it can mean any of them.

In the present invention, a disease to be treated is not particularly limited, and examples thereof include diseases caused by the expression of genes. Depending on the kind of the aforementioned disease, a gene that causes the disease may be set as the aforementioned target gene, and further, depending on the aforementioned target gene, the aforementioned expression inhibitory sequence may be set as appropriate.

A specific example is as follows. By setting the aforementioned TGF-β1 gene as the aforementioned target gene and incorporating an expression inhibitory sequence for the aforementioned gene into the aforementioned ssNc molecule, the ssNc molecule can be used for the treatment of, for example, inflammatory diseases, specifically, acute lung injury and the like.

The method of using the expression inhibitory composition and the pharmaceutical composition according to the present invention (hereinafter, both the compositions simply are referred to as "the compositions") are not particularly limited, and examples thereof include administering the aforementioned ssNc molecule to a subject having the aforementioned target gene.

Examples of the aforementioned subject to which the ssNc molecule of the present invention is administered include cells, tissues, and organs. Examples of the aforementioned subject also include humans, nonhuman animals such as nonhuman mammals, i.e., mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

The aforementioned administration method is not particularly limited, and can be determined, for example, as appropriate depending on the subject. When the aforementioned subject is a cultured cell, the administration method may be, for example, a method using a transfection reagent, an electroporation method, or the like.

For example, each of the compositions of the present invention may contain only the ssNc molecule of the present invention or further may contain an additive(s) in addition to the ssNc molecule. The aforementioned additive is not particularly limited, and is preferably, for example, a pharmaceutically acceptable additive. The kind of the aforementioned additive is not particularly limited, and can be selected as appropriate depending on, for example, the kind of the subject.

5. Expression Inhibitory Method

The expression inhibitory method according to the present invention is, as described above, a method for inhibiting the expression of a target gene, in which the aforementioned ssNc molecule of the present invention is used. The expression inhibitory method of the present invention is characterized in that the aforementioned ssNc molecule of the present invention is used therein, and other steps and conditions are by no means limited.

In the expression inhibitory method of the present invention, the mechanism by which the aforementioned gene expression is inhibited is not particularly limited, and examples thereof include inhibition of the expression by RNA interference or RNA interference-like phenomenon. The expression inhibitory method of the present invention is, for example, a method for inducing RNA interference that inhibits the aforementioned expression of a target gene, and it can also be referred to a method for inducing the expression that is characterized in that the aforementioned ssNc molecule of the present invention is used therein.

The expression inhibitory method of the present invention includes, for example, the step of administering the aforementioned ssNc molecule to a subject in which the aforementioned target gene is present. By the aforementioned administration step, for example, the aforementioned ssNc molecule is brought into contact with the aforementioned subject to which the ssNc molecule is administered. Examples of the aforementioned subject to which the ssNc molecule of the present invention is administered include cells, tissues, and organs. Examples of the aforementioned subject also include humans, nonhuman animals such as nonhuman mammals, i.e., mammals excluding humans. The aforementioned administration may be performed, for example, in vivo or in vitro.

In the expression inhibitory method of the present invention, for example, the aforementioned ssNc molecule may be administered alone, or the aforementioned composition of the present invention containing the aforementioned ssNc molecule may be administered. The aforementioned administration method is not particularly limited and, for example, can be selected as appropriate depending on the kind of the subject.

6. Treatment Method

As described above, the method for treating a disease according to the present invention includes the step of administering the aforementioned ssNc molecule of the present invention to a patient, and the aforementioned ssNc molecule includes, as the aforementioned expression inhibitory sequence, a sequence that inhibits expression of a gene causing the aforementioned disease. The treatment method of the present invention is characterized in that the aforementioned ssNc molecule of the present invention is used therein, and other steps and conditions are by no means limited.

The description regarding the aforementioned expression inhibitory method of the present invention also applies to, for example, the treatment method of the present invention, and the like. The aforementioned administration method is not particularly limited and may be any of, for example, oral administration and parenteral administration.

7. Use of ssNc Molecule

The use according to the present invention is the use of the aforementioned ssNc molecule of the present invention for the aforementioned inhibition of the expression of a target gene. Also, the use according to the present invention is the use of the aforementioned ssNc molecule of the present invention for inducing RNA interference.

The nucleic acid molecule according to the present invention is a nucleic acid molecule for use in treatment of a disease. The aforementioned nucleic acid molecule is the aforementioned ssNc molecule of the present invention, and the aforementioned ssNc molecule includes, as the aforementioned expression inhibitory sequence, a sequence that inhibits expression of a gene causing the aforementioned disease.

EXAMPLES

The Examples of the present invention are now explained. However, the present invention is not limited to the following Examples.

Example A1: Synthesis of Conjugate Single-Stranded Nucleic Acid Molecule (1) Synthesis of Single-Stranded Nucleic Acid Molecule The single-stranded nucleic acid molecules shown below were synthesized by a nucleic acid synthesizer (trade name: ABI Expedite (registered trademark) 8909 Nucleic Acid Synthesis System, Applied Biosystems) based on the phosphoramidite method. In the aforementioned synthesis, EMM amidite (WO 2013/027843) was used as RNA amidite (hereinafter the same). The aforementioned amidite was deprotected by a conventional method. The synthesized single-stranded nucleic acid molecule was purified by HPLC. The single-stranded nucleic acid molecule after purification was each freeze-dried. In the following single-stranded nucleic acid molecules, the underlined parts in KH-0001, NH-0005, PH-0009 are expression inhibitory sequences of human TGF-β1 gene, and the underlined part in KH-0010 is an expression inhibitory sequence of luciferase gene.

KH-0001
(SEQ ID NO: 29)
5'-GCAGAGUACACACAGCAUAUACC-Lx-GGUA<u>UAUGCUGUGUGUACUC</u>
<u>UGCUU</u>-3'

NH-0005
(SEQ ID NO: 30)
5'-GCAGAGUACACACAGCAUAUACCCACACCGGUA<u>UAUGCUGUGUGUA</u>
<u>CUCUGCUU</u>-3'

PH-0009
(SEQ ID NO: 29)
5'-GCAGAGUACACACAGCAUAUACC-Lx-GGUA<u>UAUGCUGUGUGUACUC</u>
<u>UGCUU</u>-3'

KH-0010
(SEQ ID NO: 31)
5'-CUUACGCUGAGUACUUCGAUUCC-Lx-GGAA<u>UCGAAGUACUCAGCGU</u>
<u>AAGUU</u>-3'

KH-0030
(SEQ ID NO: 29)
5'-GCAGAGUACACACAGCAUAUACC-Lx-GGUA<u>UAUGCUGUGUGUACUC</u>
<u>UGCUU</u>-3'

PH-0000
(SEQ ID NO: 32)
5'-UACUAUUCGACACGCGAAGUUCC-Lx-GGAACUUCGCGUGUCGAAUA
GUAUU-3'

KH-0001 which is the single-stranded nucleic acid molecule of the present invention is a single-stranded nucleic acid molecule using the following lysineamidite as a linker region (Lx).

[Chem. 4]

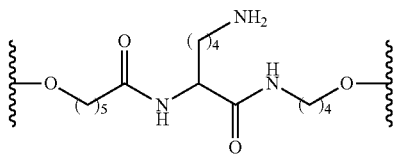

The aforementioned NH-0005 and PH-0009 are single-stranded nucleic acid molecules of Comparative Examples, NH-0005 is a single-stranded nucleic acid molecule using only nucleotide residues as a linker region (Lx), and PH-0009 is a single-stranded nucleic acid molecule using the following L-prolinediamideamidite as a linker region (Lx).

[Chem. 5]

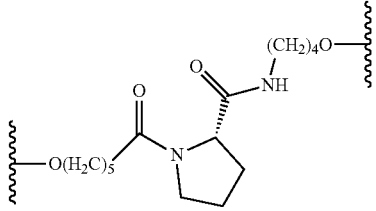

KH-0010 which is the single-stranded nucleic acid molecule of the present invention is a single-stranded nucleic acid molecule using the above-mentioned lysineamidite as a linker region (Lx).

KH-0030 which is the single-stranded nucleic acid molecule of the present invention is a single-stranded nucleic acid molecule using the following lysine-cholesterolamidite as a linker region (Lx).

[Chem. 6]

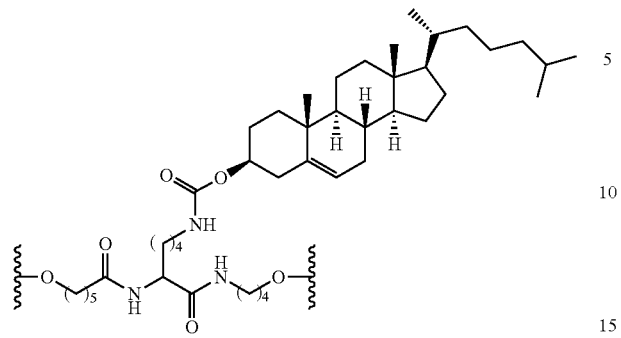

The aforementioned PH-0000 is a single-stranded nucleic acid molecule as a negative control and is a single-stranded nucleic acid molecule using the above-mentioned L-prolinediamideamidite as a linker region (Lx).

(2) Synthesis of Lipid-Conjugated Single-Stranded Nucleic Acid Molecule

The structure of KH-0001-C18 which is the lipid-conjugated single-stranded nucleic acid molecule of the present invention is shown below.

KH-0001-C18 is a single-stranded nucleic acid molecule in which stearic acid (C18) as a single-chain lipid is bonded to the linker region (Lx) of the aforementioned KH-0001 by the below-mentioned method.

KH-0001-C18 (SEQ ID NOs: 29 (guide strand) and 37 (passenger strand))

[Chem. KHC18]

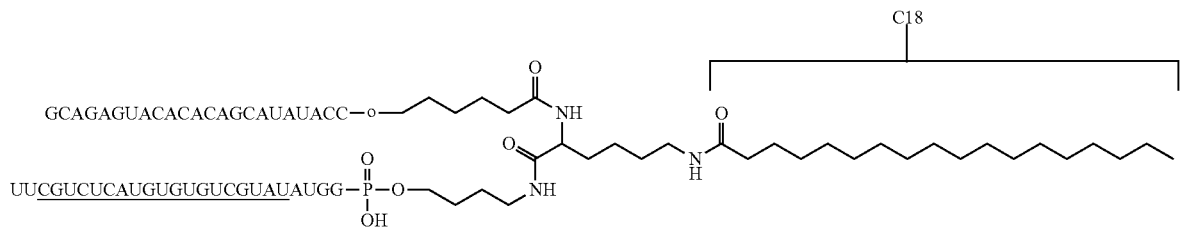

Synthesis of KH-0001-C18

Figure 2:
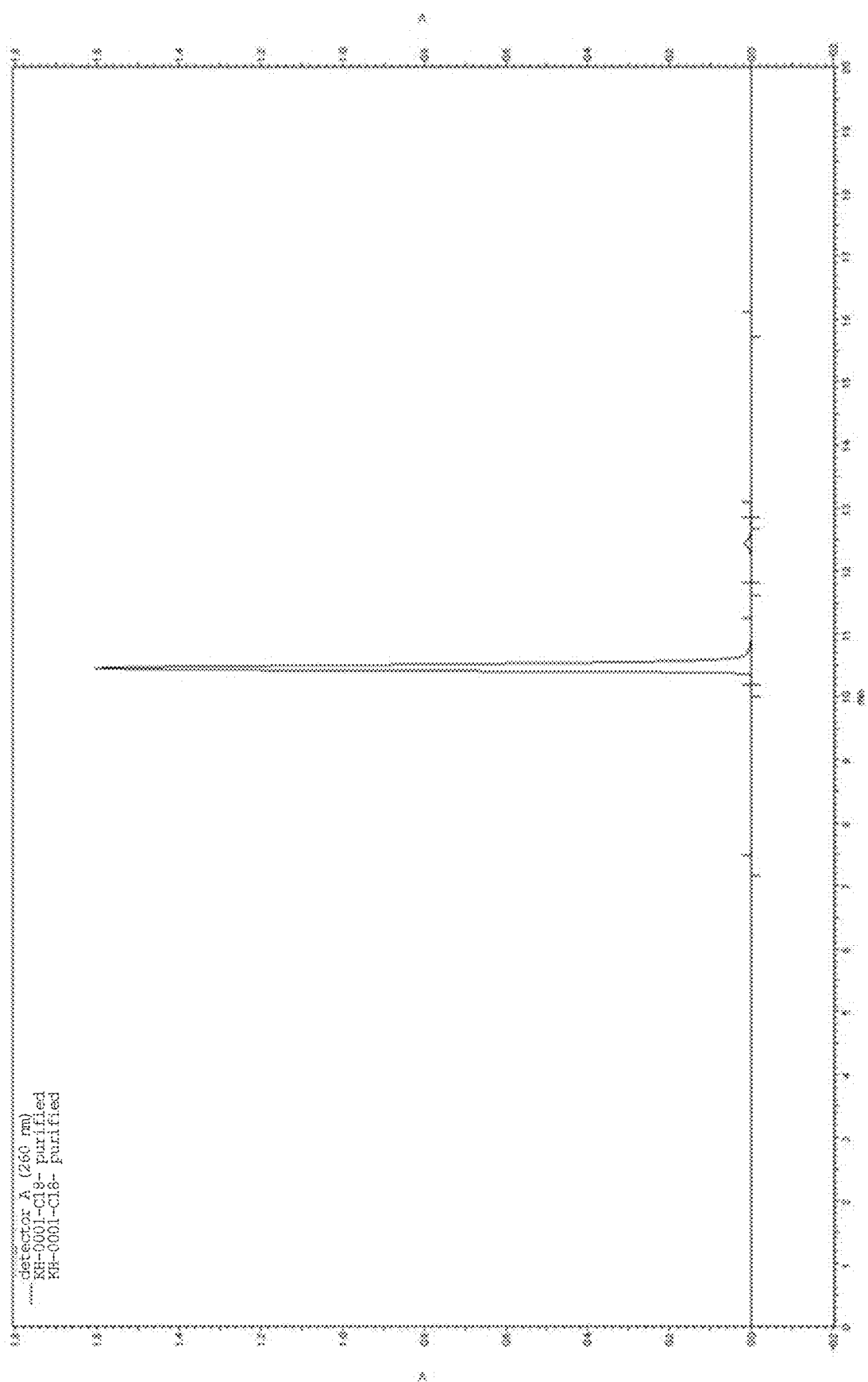
FIG. 2 is an HPLC chart of a C18-conjugated single-stranded nucleic acid molecule after purification in an Example of the present invention.

500 μmol/L KH-0001 (200 μL), 50 mmol/L C18-NHS/DMF solution (80 μL), isopropanol (320 μL), and carbonate buffer (400 μL) (pH 9.2, final concentration 100 mmol/L) were mixed, and the mixture was stirred at 40° C. for 3 hr. The reaction mixture was purified by HPLC (column: Develosil 08-UG-5, 5 μm, 10×50 mm; flow rate: 4.7 mL/min; detection: UV 260 nm; column oven: 35° C.; Buffer A: 50 mmol/L TEAA, 5% $CH_3CN$; Buffer B: $CH_3CN$) to separate the peak of the object product. The separated fraction was subjected to ethanol precipitation, and the resulting precipitate was dissolved in distilled water for injection (Otsuka Pharmaceutical Co., Ltd.). The absorbance at UV 260 nm was measured, and the yield was calculated to give KH-0001-C18 (6.5 mg) having a purity of 98.45%. Mass spectrometry: 15989.34 (Calculated: 15989.06). An HPLC chart after purification is shown in FIG. 2.

The structure of KH-0001-DOPE which is the lipid-conjugated single-stranded nucleic acid molecule of the present invention is shown below.

KH-0001-DOPE is a single-stranded nucleic acid molecule in which DOPE as a double-chain lipid is bonded to the linker region (Lx) of the aforementioned KH-0001 by the below-mentioned method.

KH-0001-DOPE (SEQ ID NOs: 29 (guide strand) and 37 (passenger strand))

[Chem. KHDOPE]
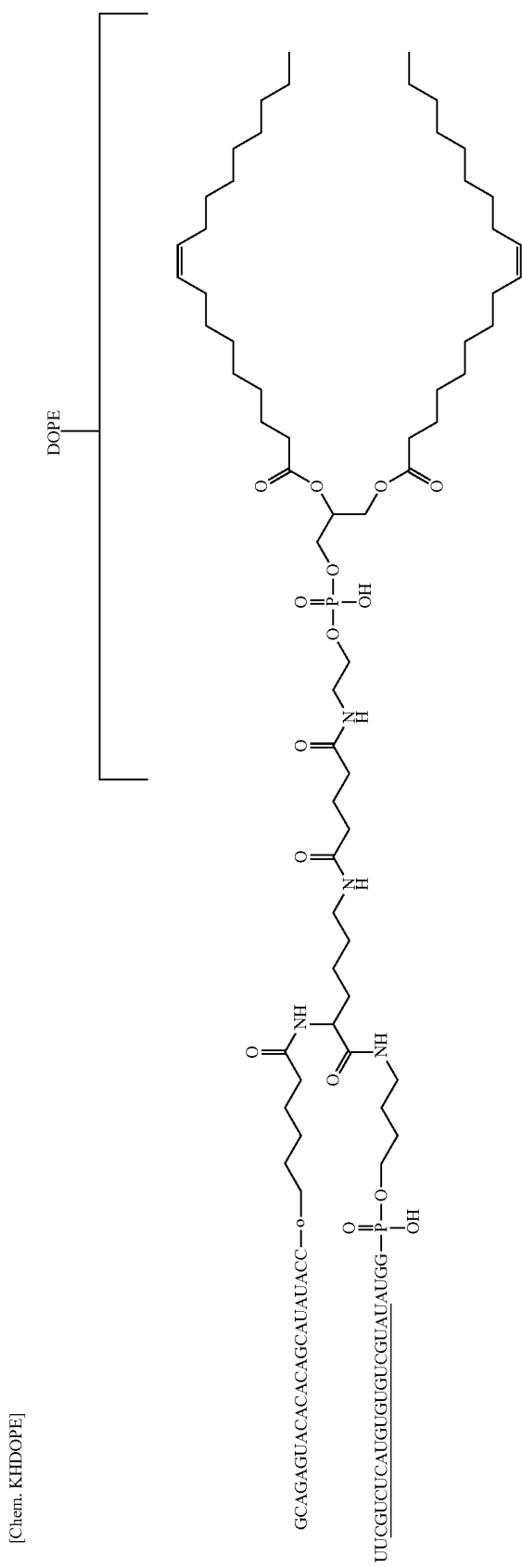

Synthesis of KH-0001-DOPE

Figure 3:
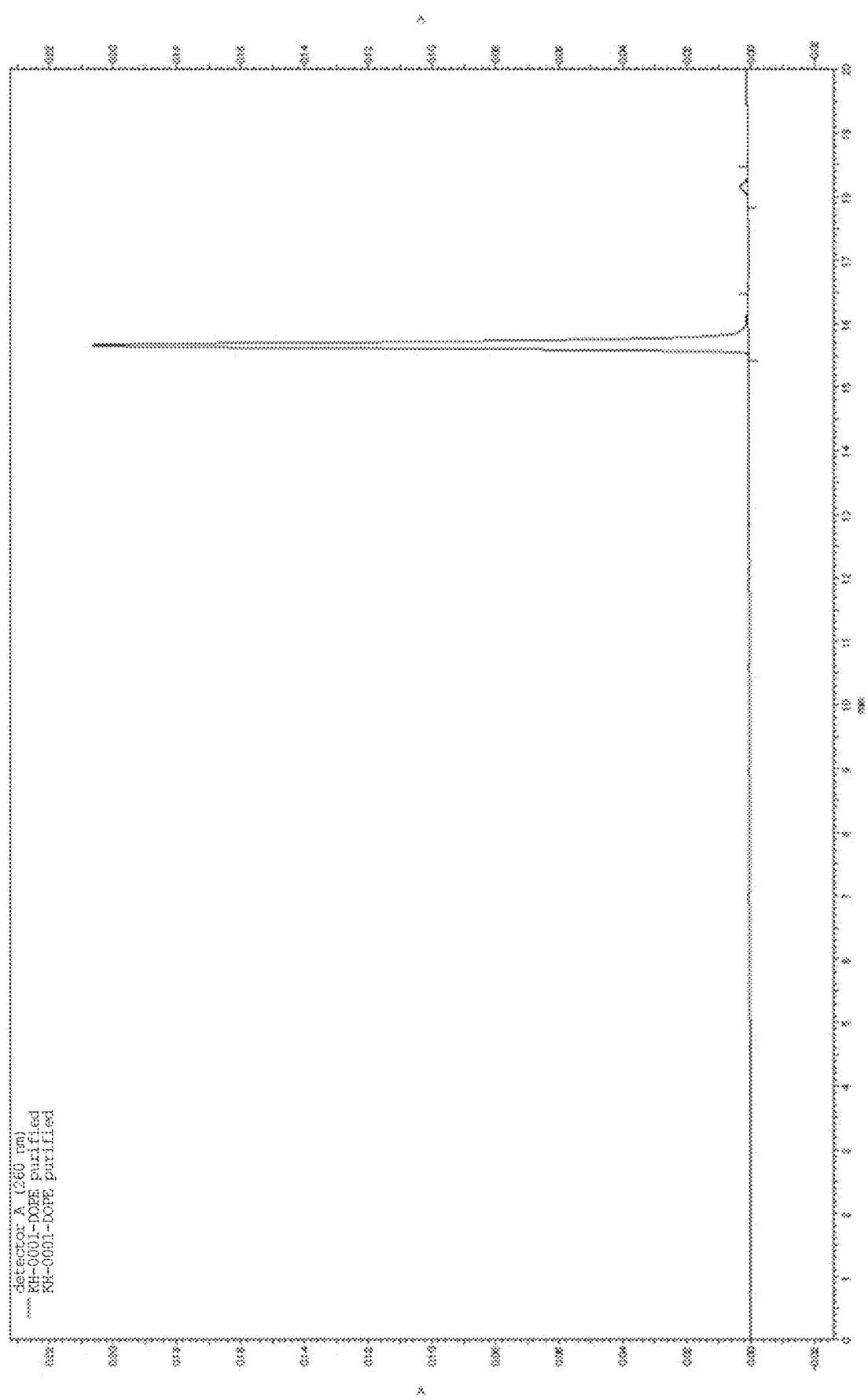
FIG. 3 is an HPLC chart of a DOPE-conjugated single-stranded nucleic acid molecule after purification in an Example of the present invention.

KH-0001 (1115 μM, 100 μL), 10 mM DOPE-NHS/ethanol solution (400 μL), ethanol (200 μL), 1% aqueous triethylamine solution (100 μL), and distilled water for injection (200 μL) were mixed, and the mixture was stirred at 40° C. for 3 hr. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mM TEAA, 5% CH$_3$CN; Buffer B: CH$_3$CN) and the peak of the object product was separated. The separated fraction was subjected to ethanol precipitation and the resulting precipitate was dissolved in distilled water for injection. The absorbance at UV 260 nm was measured and the yield was calculated to give KH-0001-DOPE (3.0 mg) having a purity of 98.64%. Mass spectrometry: 16562.52 (Calculated: 16562.71). An HPLC chart after purification is shown in FIG. 3.

The structure of KH-0001-Chol which is the lipid-conjugated single-stranded nucleic acid molecule of the present invention is shown below.

KH-0001-Chol is a single-stranded nucleic acid molecule in which cholesterol is bonded via an ethyleneglycol linker to the linker region (Lx) of the aforementioned KH-0001 by the below-mentioned method.

KH-0001-Chol (SEQ ID NOs: 29 (guide strand) and 37 (passenger strand))

[Chem. KHChol]

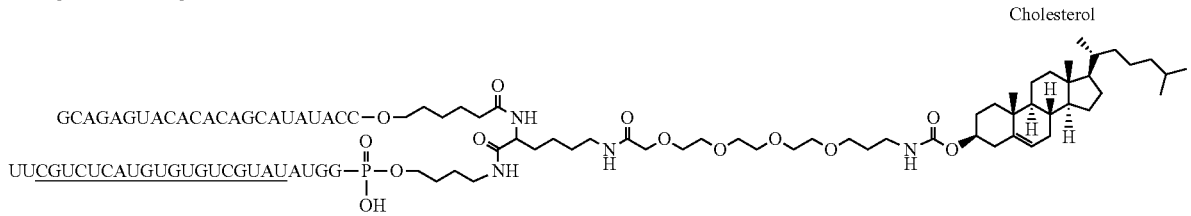

Synthesis of KH-0001-Chol

500 μmol/L KH-0001 (200 μL), 50 mmol/L Cholesteryl-EG-NHS Ester/DMF solution (80 μL), isopropanol (320 μL), and carbonate buffer (400 μL) (pH 9.2, final concentration 100 mmol/L) were mixed and the mixture was stirred at 50° C. overnight. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mmol/L TEAA, 5% CH$_3$CN; Buffer B: CH$_3$CN) and the peak of the object product was separated. The separated fraction was subjected to ethanol precipitation and the resulting precipitate was dissolved in distilled water for injection (Otsuka Pharmaceutical Co., Ltd.). The absorbance at UV 260 nm was measured and the yield was calculated to give KH-0001-Chol (0.9 mg) having a purity of 95.47%. Mass spectrometry: 16382.13 (Calculated: 16382.55).

(3) Synthesis of Carbohydrate-Conjugated Single-Stranded Nucleic Acid Molecule

The structure of KH-0001-Lac which is the carbohydrate-conjugated single-stranded nucleic acid molecule of the present invention is shown below.

KH-0001-Lac is a single-stranded nucleic acid molecule in which lactose as a disaccharide is bonded to the linker region (Lx) of the aforementioned KH-0001 by the below-mentioned method.

KH-0001-Lac (SEQ ID NOs: 29 (guide strand) and 37 (passenger strand))

[Chem. KHLac]

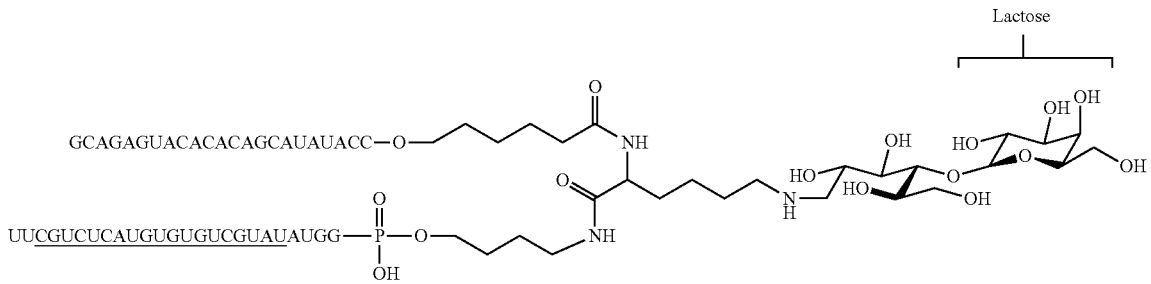

Figure 4:
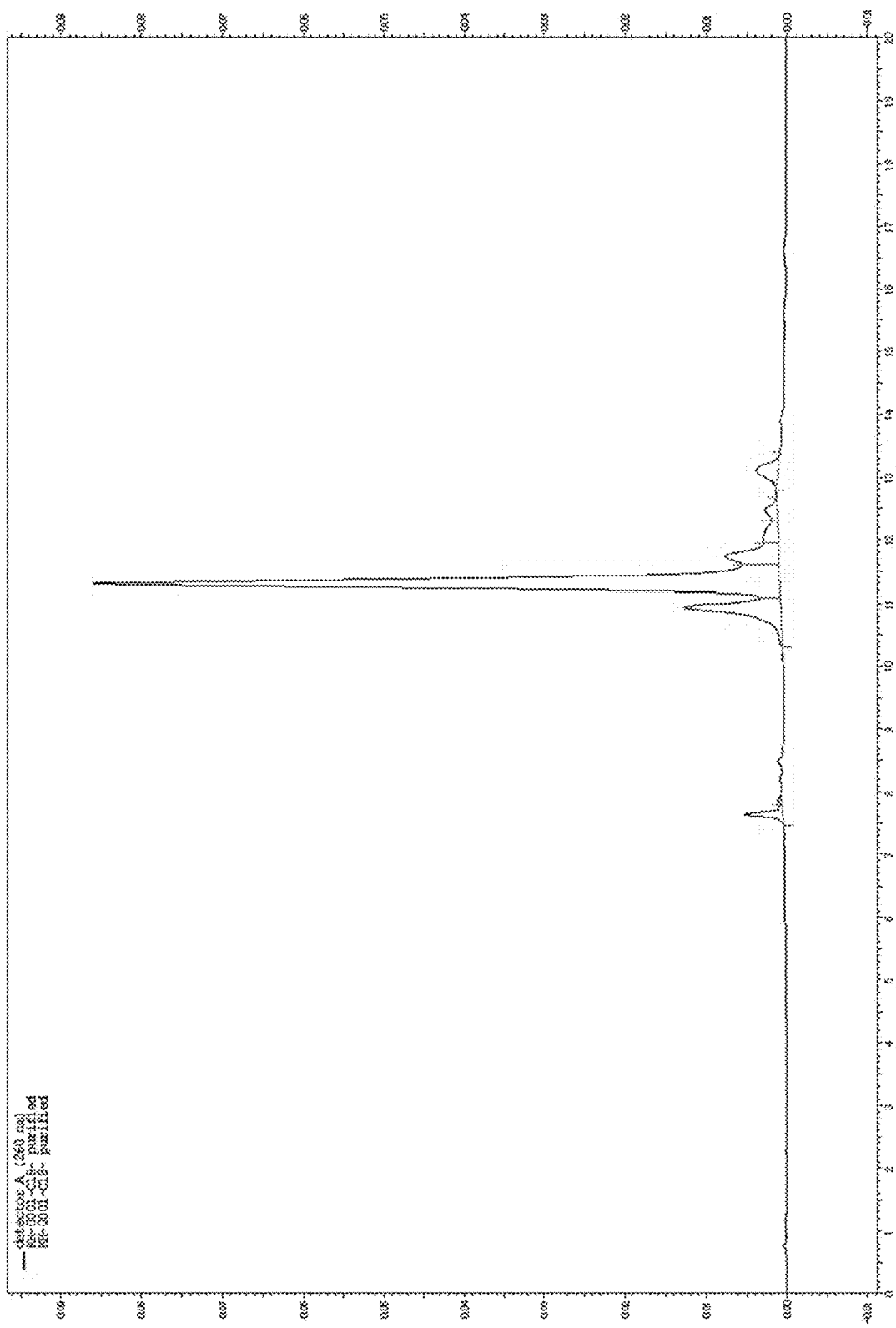
FIG. 4 is an HPLC chart of a lactose-conjugated single-stranded nucleic acid molecule after purification in an Example of the present invention.

Synthesis of KH-0001-Lac 1 mmol/L KH-0001 (100 μL), 2 mol/L lactose (50 μL), methanol (600 μL), acetate buffer (200 μL) (pH 3.8, final concentration 200 mmol/L), and 10 mol/L NaBH$_3$CN/methanol solution (50 μL) were mixed, and the mixture was stirred at 60° C. for 20 hr. The reaction mixture was purified by Sephadex G-25 (PD-10; GE Healthcare), and production of the object product was confirmed by mass spectrometry. Mass spectrometry: 16048.38 (Calculated: 16048.89). An HPLC chart after purification is shown in FIG. 4.

The structure of KH-0001-GalNAc which is the carbohydrate-conjugated single-stranded nucleic acid molecule of the present invention is shown below.

KH-0001-GalNAc is a single-stranded nucleic acid molecule in which N-acetylgalactosamine as a monosaccharide is bonded to the linker region (Lx) of the aforementioned KH-0001 by the below-mentioned method.

KH-0001-GalNAc (SEQ ID NOs: 29 (guide strand) and 37 (passenger strand))

Synthesis of KH-0001-GalNAc 1 mmol/L KH-0001 (100 μL), 2 mol/L N-acetylgalactosamine (50 μL), methanol (600 μL), acetate buffer (200 μL) (pH 3.8, final concentration 200 mmol/L), and 10 mol/L NaBH$_3$CN/methanol solution (50 μL) were mixed, and the mixture was stirred at 60° C. overnight. The reaction mixture was purified by Sephadex G-25 (PD-10; GE Healthcare), and production of the object product was confirmed by mass spectrometry. Mass spectrometry: 15927.54 (Calculated: 15927.81).

The structure of KH-0001-GlcNAc which is the carbohydrate-conjugated single-stranded nucleic acid molecule of the present invention is shown below.

KH-0001-GlcNAc is a single-stranded nucleic acid molecule in which N-acetylglucosamine as a monosaccharide is bonded to the linker region (Lx) of the aforementioned KH-0001 by the below-mentioned method.

KH-0001-GlcNAc (SEQ ID NOs: 29 (guide strand) and 37 (passenger strand))

[Chem. KHGalNAc]

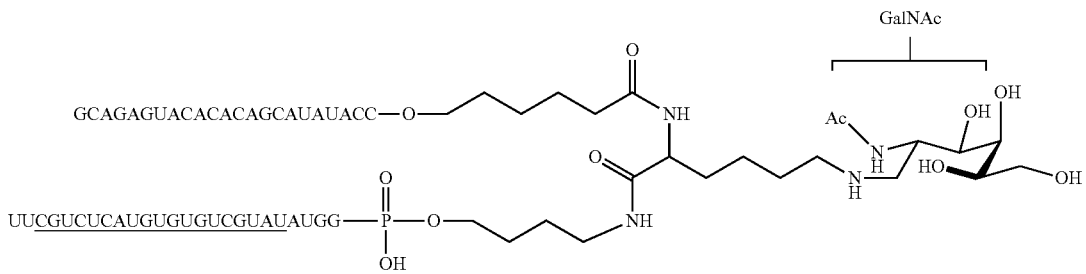

[Chem. KHGlcNAc]

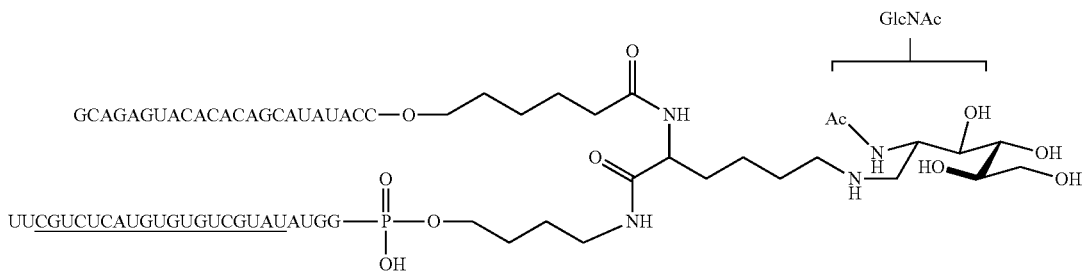

Synthesis of KH-0001-GlcNAc 1 mmol/L KH-0001 (100 μL), 2 mol/L N-acetylglucosamine (50 μL), methanol (600 μL), acetate buffer (200 μL) (pH 3.8, final concentration 200 mmol/L), and 10 mol/L NaBH$_3$CN/methanol solution (50 μL) were mixed, and the mixture was stirred at 60° C. overnight. The reaction mixture was purified by Sephadex G-25 (PD-10; GE Healthcare), and production of the object product was confirmed by mass spectrometry. Mass spectrometry: 15927.85 (Calculated: 15927.81).

(4) Synthesis of Peptide-Conjugated Single-Stranded Nucleic Acid Molecule

The structure of KH-0010-GE11 which is the peptide-conjugated single-stranded nucleic acid molecule of the present invention is shown below.

KH-0010-GE11 is a single-stranded nucleic acid molecule in which GE11 as a peptide shown by the aforementioned SEQ ID NO: 12 is bonded via a GMBS linker to the linker region (Lx) of the aforementioned KH-0010 by the below-mentioned method.

Figure 5:
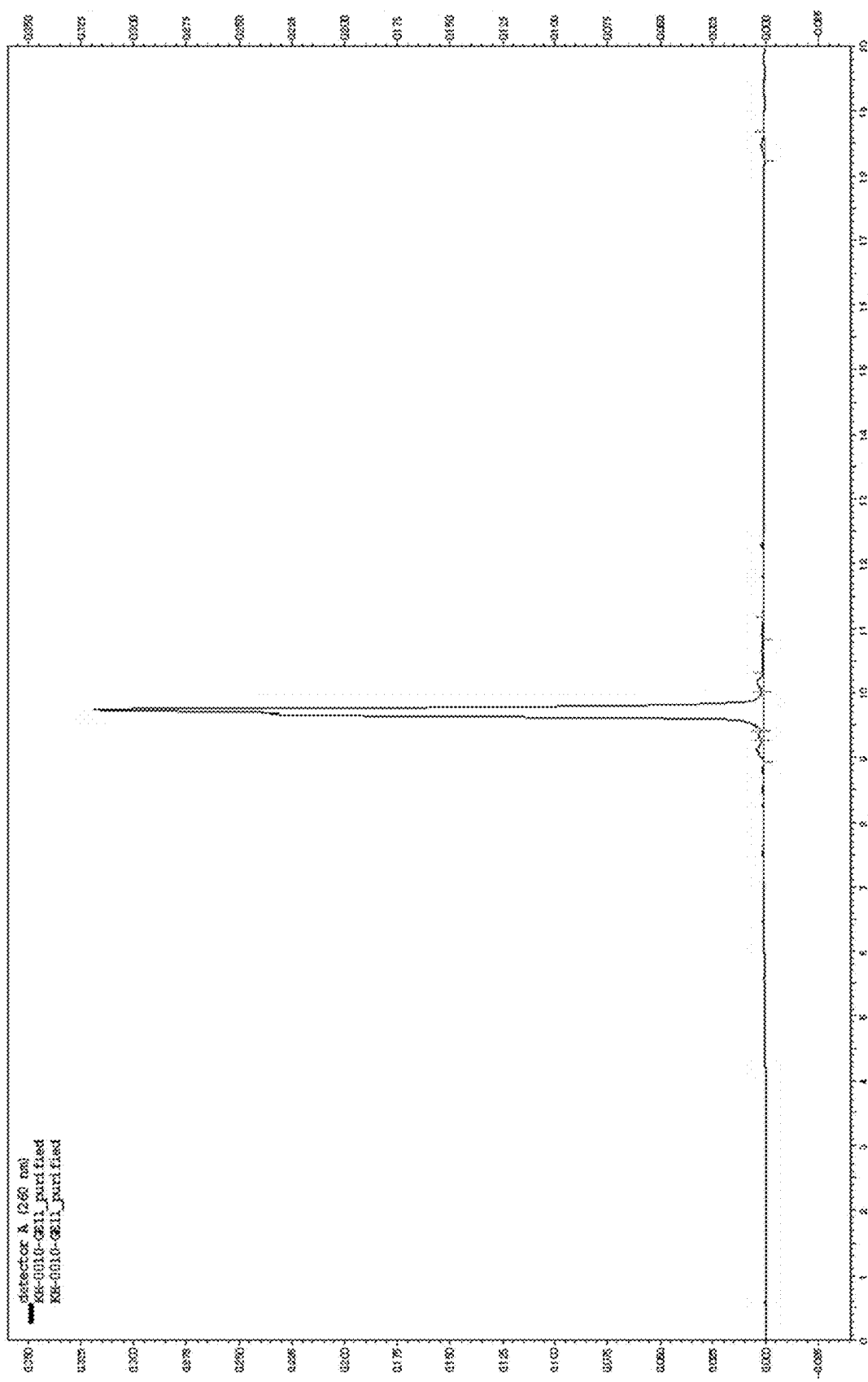
FIG. 5 is an HPLC chart of a GE11-conjugated single-stranded nucleic acid molecule after purification in an Example of the present invention.

KH-0010-GE11 (SEQ ID NOs: 31 (guide strand) and 38 (passenger strand))

was stirred at room temperature for 3 hr. The reaction mixture was purified by Sephadex G-25 (PD-10; GE Healthcare), 1 mg of GE11 peptide was added in 100 mmol/L phosphate buffer (pH 7.0), and the mixture was stirred at room temperature for 1 hr. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mmol/L TEAA, 5% CH$_3$CN; Buffer B: CH$_3$CN), and the peak of the object product was separated. The separated fraction was subjected to ethanol precipitation and the resulting precipitate was dissolved in distilled water for injection (Otsuka Pharmaceutical Co., Ltd.). The absorbance at UV 260 nm was measured and the yield was calculated to give KH-0010-GE11 (0.7 mg) having a purity of 95.97%. An HPLC chart after purification is shown in FIG. 5.

The structure of KH-0010-GE11(7) which is the peptide-conjugated single-stranded nucleic acid molecule of the present invention is shown below.

KH-0010-GE11(7) is a single-stranded nucleic acid molecule in which GE11(7) as a peptide shown by the afore-

[Chem. KHGE11]

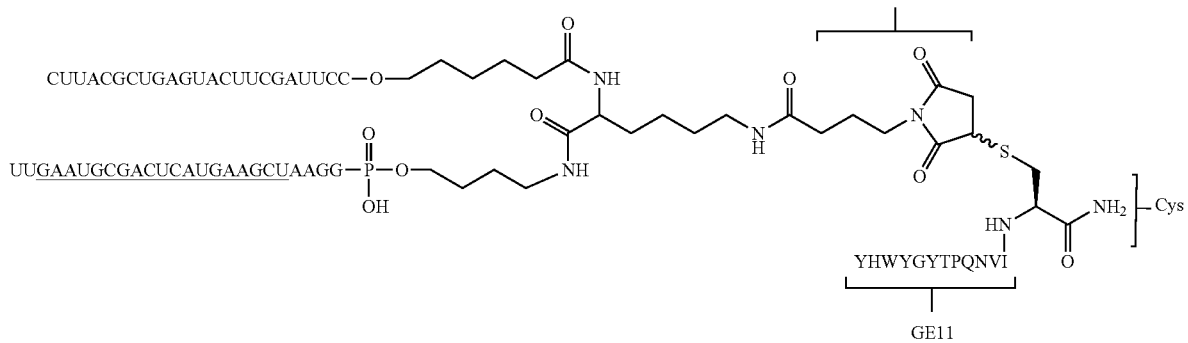

Synthesis of KH-0010-GE11

500 μmol/L KH-0010 (200 μL), 4 mmol/L GMBS/DMF solution (500 μL), and phosphate buffer (pH 7.0, final concentration 120 mmol/L) were mixed, and the mixture mentioned SEQ ID NO: 13 is bonded, via a GMBS linker, to the linker region (Lx) of the aforementioned KH-0010 by the below-mentioned method.

KH-0010-GE11(7) (SEQ ID NOs: 31 (guide strand) and 38 (passenger strand))

[Chem. KHGE11(7)]

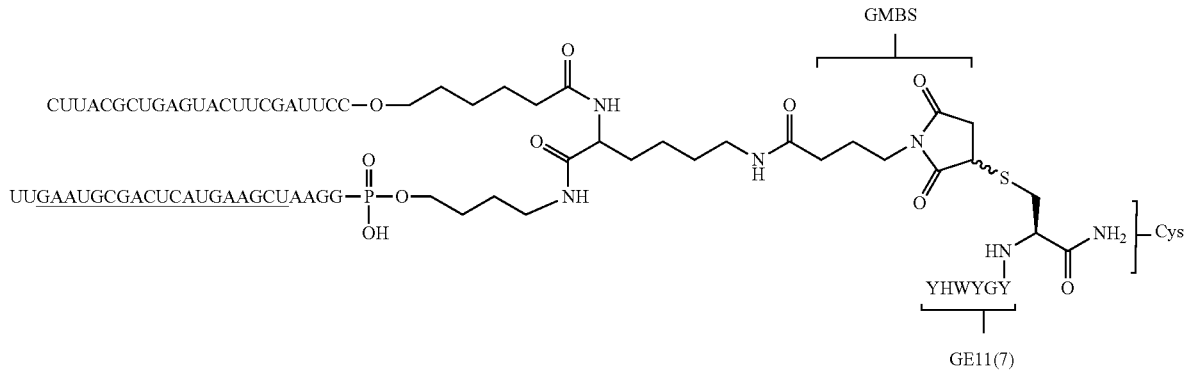

Synthesis of KH-0010-GE11(7)

Figure 6:
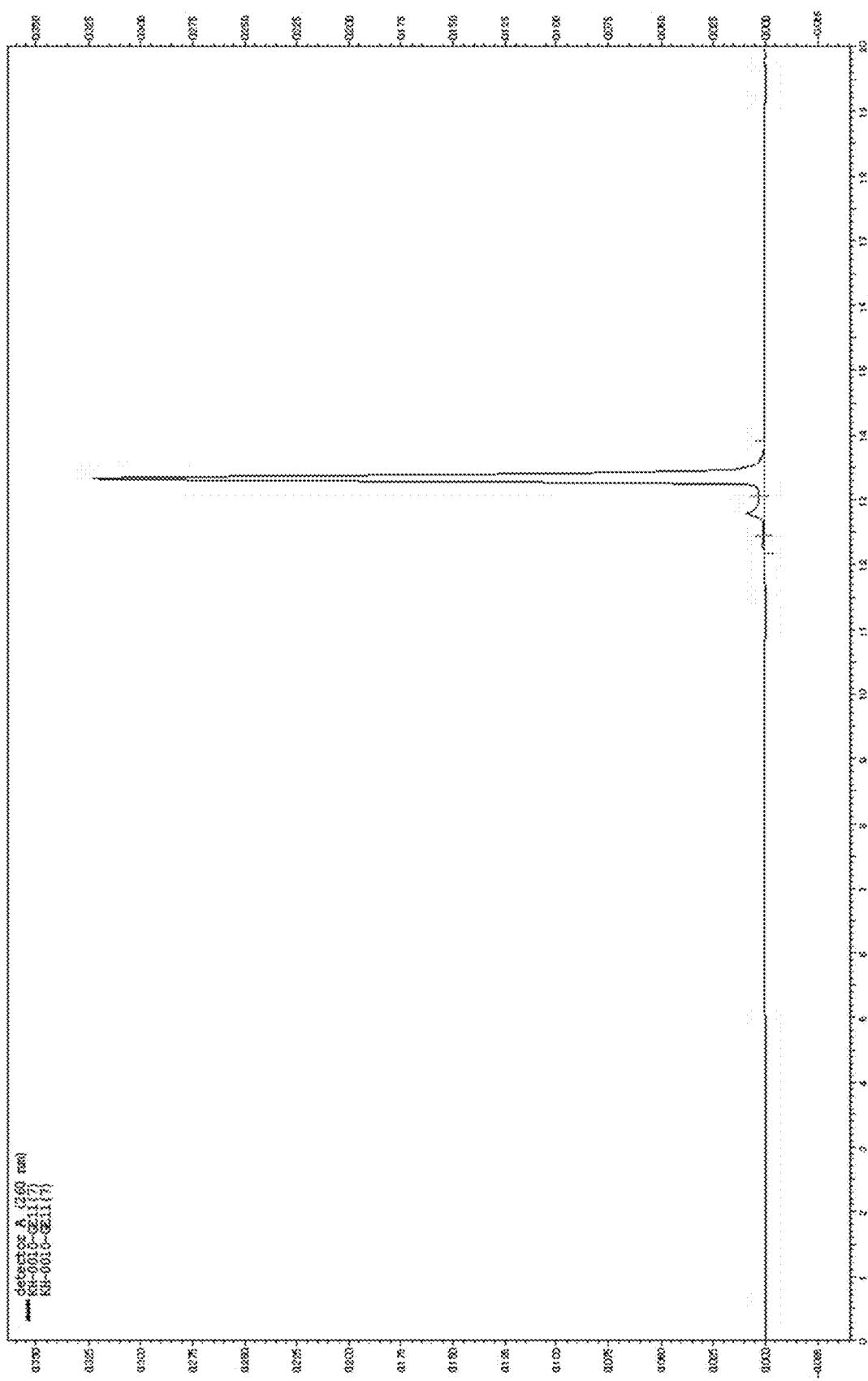
FIG. 6 is an HPLC chart of a GE11(7)-conjugated single-stranded nucleic acid molecule after purification in an Example of the present invention.

500 μmol/L KH-0010 (200 μL), 4 mmol/L GMBS/DMF solution (500 μL), and phosphate buffer (pH 7.0, final concentration 120 mmol/L) were mixed, and the mixture was stirred at room temperature for 3 hr. The reaction mixture was purified by Sephadex G-25 (PD-10; GE Healthcare), 1 mg of GE11(7) peptide was added in 100 mmol/L phosphate buffer (pH 7.0), and the mixture was stirred at room temperature for 1 hr. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mmol/L TEAA, 5% $CH_3CN$; Buffer B: $CH_3CN$) and the peak of the object product was separated. The separated fraction was subjected to ethanol precipitation and the resulting precipitate was dissolved in distilled water for injection (Otsuka Pharmaceutical Co., Ltd.). The absorbance at UV 260 nm was measured and the yield was calculated to give KH-0010-GE11(7) (0.3 mg) having a purity of 95.12%. Mass spectrometry: 16877.66 (Calculated: 16877.74). An HPLC chart after purification is shown in FIG. 6.

The structure of KH-0010-GE11(5) which is the peptide-conjugated single-stranded nucleic acid molecule of the present invention is shown below.

KH-0010-GE11(5) is a single-stranded nucleic acid molecule in which GE11(5) as a peptide shown by the aforementioned SEQ ID NO: 14 is bonded, via a GMBS linker, to the linker region (Lx) of the aforementioned KH-0010 by the below-mentioned method.

KH-0010-GE11(5) (SEQ ID NOs: 31 (guide strand) and 38 (passenger strand))

[Chem. KHGE11 (5)]

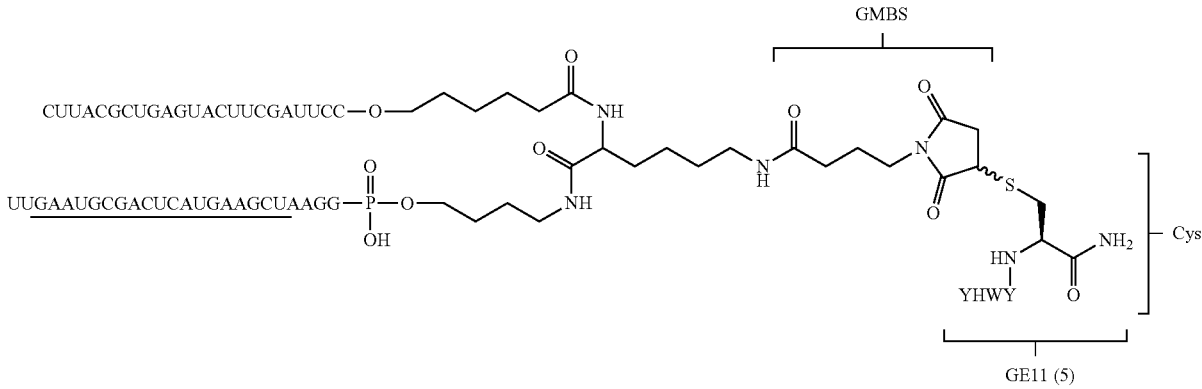

Synthesis of KH-0010-GE11(5)

Figure 7:
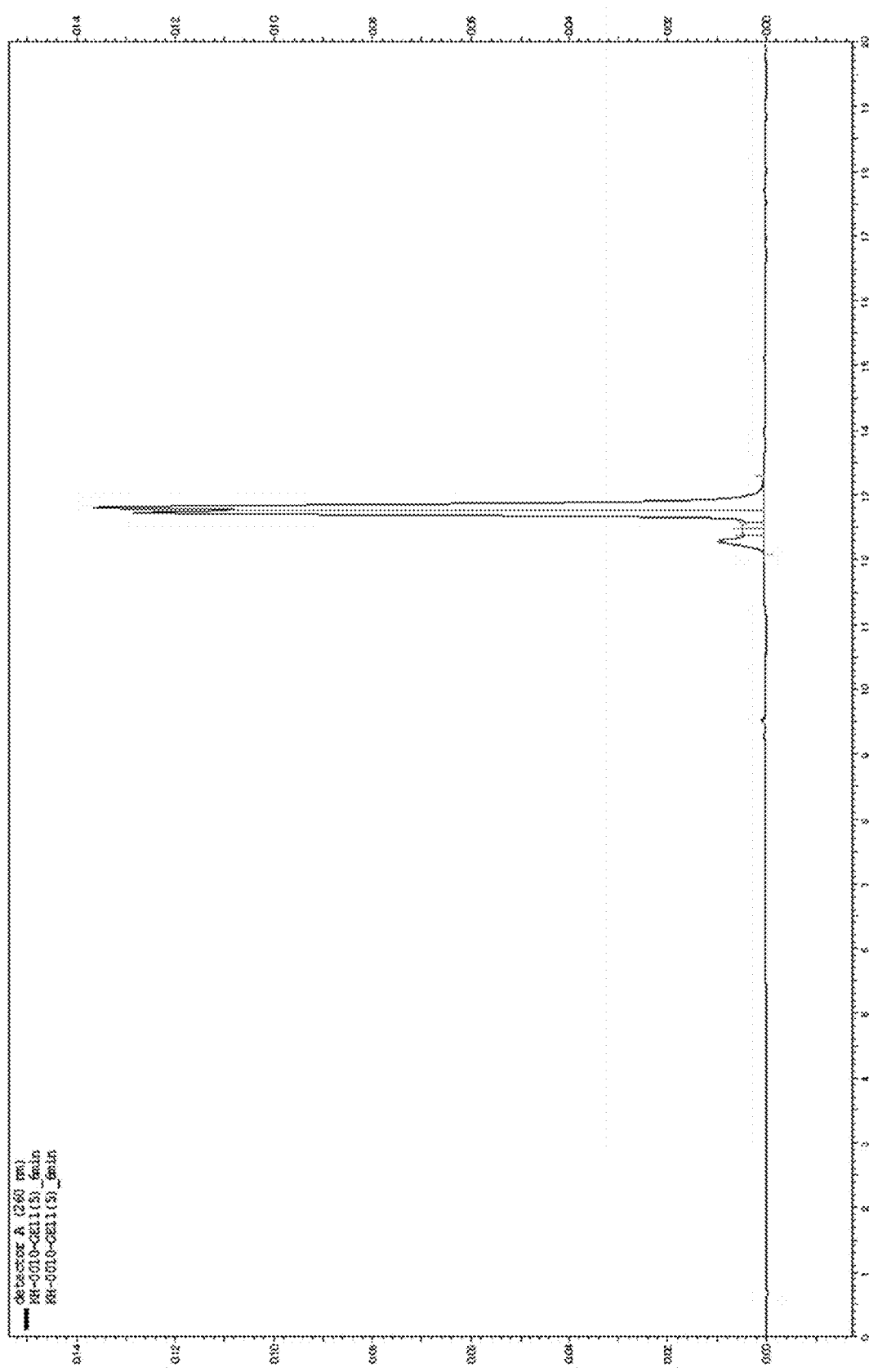
FIG. 7 is an HPLC chart of a GE11 (5)-conjugated single-stranded nucleic acid molecule after purification in an Example of the present invention.

500 μmol/L KH-0010 (200 μL), 4 mmol/L GMBS/DMF solution (500 μL), and phosphate buffer (pH 7.0, final concentration 120 mmol/L) were mixed, and the mixture was stirred at room temperature for 3 hr. The reaction mixture was purified by Sephadex G-25 (PD-10; GE Healthcare), 1 mg of GE11(5) peptide was added in 100 mmol/L phosphate buffer (pH 7.0), and the mixture was stirred at room temperature for 1 hr. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mmol/L TEAA, 5% $CH_3CN$; Buffer B: $CH_3CN$) and the peak of the object product was separated. The separated fraction was subjected to ethanol precipitation and the resulting precipitate was dissolved in distilled water for injection (Otsuka Pharmaceutical Co., Ltd.). The absorbance at UV 260 nm was measured and the yield was calculated to give KH-0010-GE11(5) (0.6 mg) having a purity of 92.12%. Mass spectrometry: 16657.41 (Calculated: 16657.54). An HPLC chart after purification is shown in FIG. 7.

The structure of KH-0001-GE11 which is the peptide-conjugated single-stranded nucleic acid molecule of the present invention is shown below.

KH-0001-GE11 is a single-stranded nucleic acid molecule in which GE11 as a peptide shown by the aforementioned SEQ ID NO: 12 is bonded, via a GMBS linker, to the linker region (Lx) of the aforementioned KH-0001 by the below-mentioned method.

KH-0001-GE11 (SEQ ID NOs: 29 (guide strand) and 37 (passenger strand))

[Chem. KH01GE11]

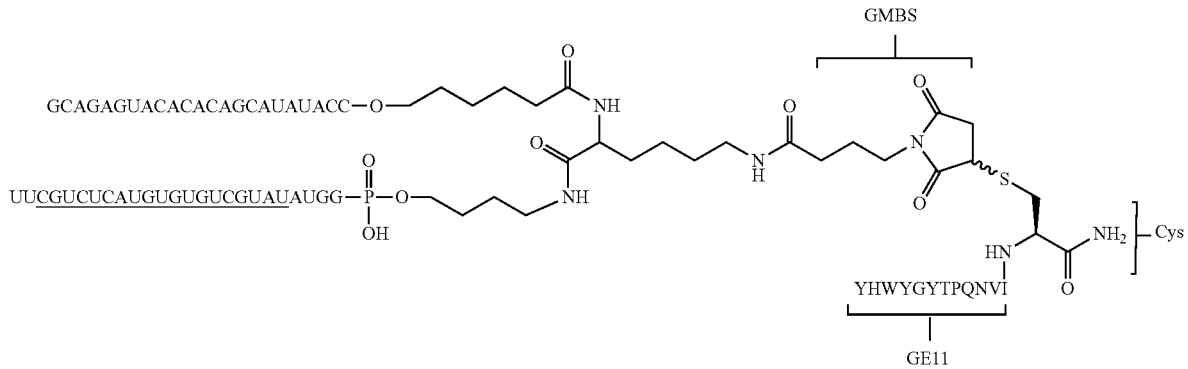

Synthesis of KH-0001-GE11

Figure 8:
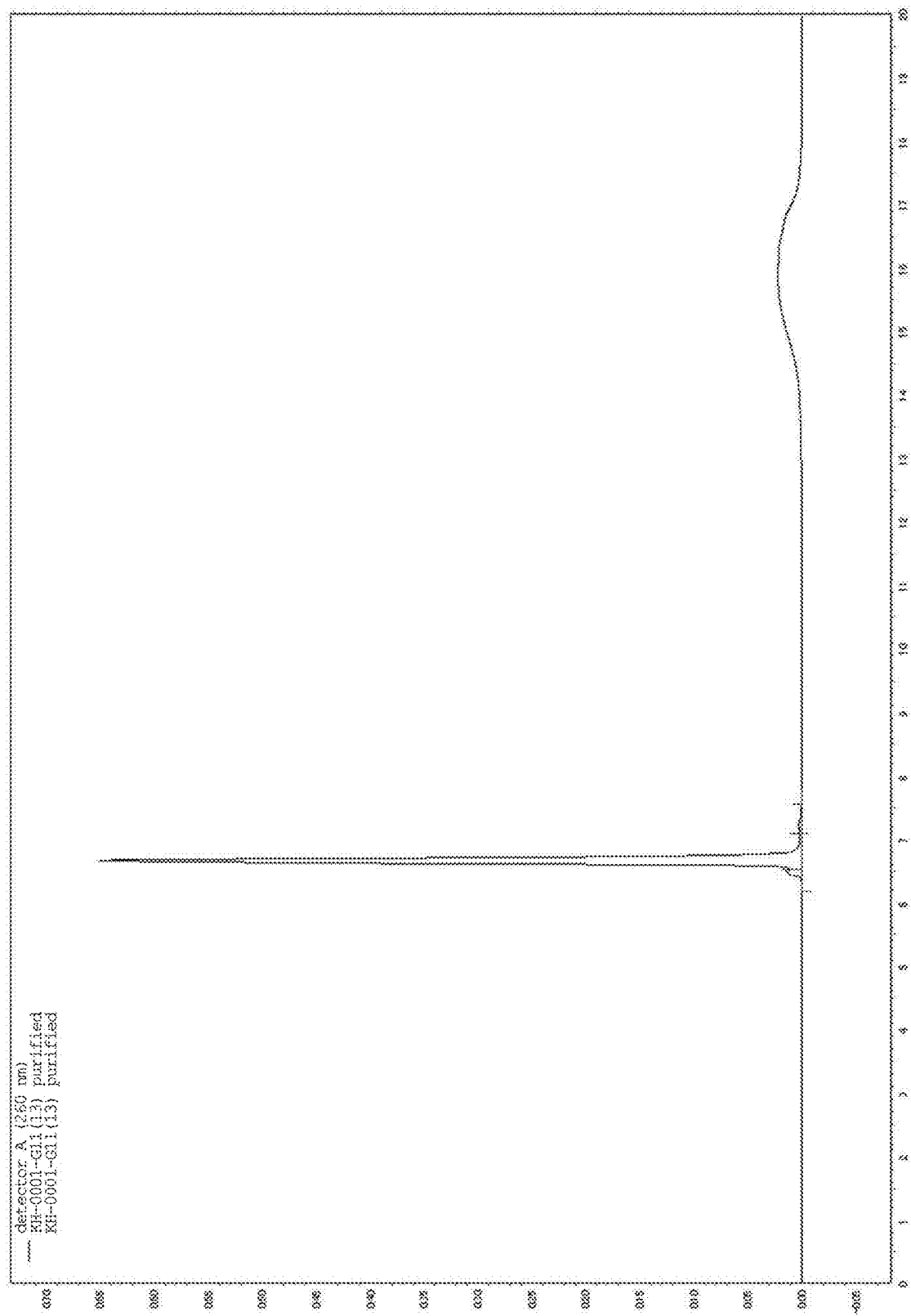
FIG. 8 is an HPLC chart of a GE11-conjugated single-stranded nucleic acid molecule after purification in an Example of the present invention.

500 μmol/L KH-0001 (800 μL), 4 mmol/L GMBS/DMF solution (2000 μL), 1 mol/L phosphate buffer (pH 7.0) (480 μL), and distilled water for injection (720 μL) were mixed, and the mixture was stirred at room temperature for 3 hr. The reaction mixture was purified by Sephadex G-25 (PD-10; GE Healthcare), and a ⅓ amount thereof was used for the next reaction. 1 mg of GE11 peptide was added in 100 mmol/L phosphate buffer (pH 7.0), and the mixture was stirred at room temperature for 1 hr. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mmol/L TEAA, 5% CH₃CN; Buffer B: CH₃CN) and the peak of the object product was separated. The separated fraction was subjected to ethanol precipitation and the resulting precipitate was dissolved in distilled water for injection (Otsuka Pharmaceutical Co., Ltd.). The absorbance at UV 260 nm was measured and the yield was calculated to give KH-0001-GE11 (1.1 mg) having a purity of 96.85%. Mass spectrometry: 17530.41 (Calculated: 17530.61). An HPLC chart after purification is shown in FIG. 8.

The structure of KH-0001-GE11(7) which is the peptide-conjugated single-stranded nucleic acid molecule of the present invention is shown below.

KH-0001-GE11(7) is a single-stranded nucleic acid molecule in which GE11(7) as a peptide shown by the aforementioned SEQ ID NO: 13 is bonded, via a GMBS linker, to the linker region (Lx) of the aforementioned KH-0001 by the below-mentioned method.

KH-0001-GE11(7) (SEQ ID NOs: 29 (guide strand) and 37 (passenger strand))

[Chem. KH01GE11(7)]

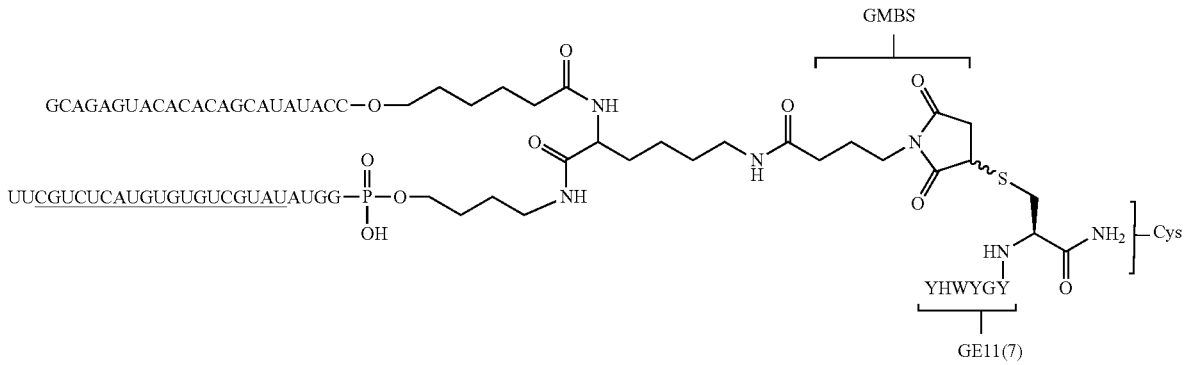

Synthesis of KH-0001-GE11(7)

Figure 9:
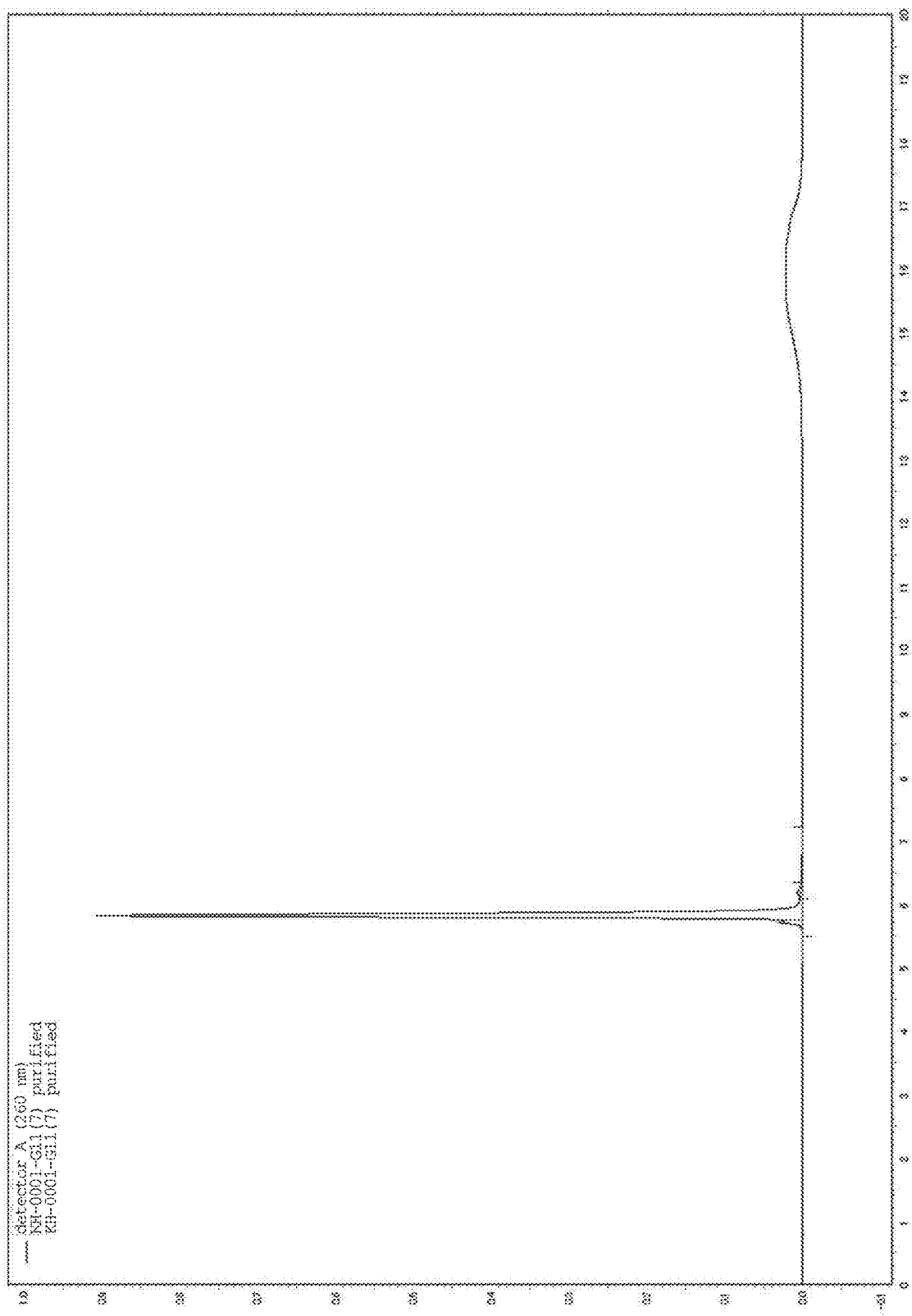
FIG. 9 is an HPLC chart of a GE11(7)-conjugated single-stranded nucleic acid molecule after purification in an Example of the present invention.

500 μmol/L KH-0001 (800 μL), 4 mmol/L GMBS/DMF solution (2000 μL), 1 mol/L phosphate buffer (pH 7.0) (480 μL), and distilled water for injection (720 μL) were mixed, and the mixture was stirred at room temperature for 3 hr. The reaction mixture was purified by Sephadex G-25 (PD-10; GE Healthcare), and a ⅓ amount thereof was used for the next reaction. 1 mg of GE11(7) peptide was added in 100 mmol/L phosphate buffer (pH 7.0), and the mixture was stirred at room temperature for 1 hr. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mmol/L TEAA, 5% $CH_3CN$; Buffer B: $CH_3CN$) and the peak of the object product was separated. The separated fraction was subjected to ethanol precipitation and the resulting precipitate was dissolved in distilled water for injection (Otsuka Pharmaceutical Co., Ltd.). The absorbance at UV 260 nm was measured and the yield was calculated to give KH-0001-GE11(7) (1.1 mg) having a purity of 96.40%. Mass spectrometry: 16877.65 (Calculated: 16877.74). An HPLC chart after purification is shown in FIG. 9.

The structure of KH-0001-GE11(5) which is the peptide-conjugated single-stranded nucleic acid molecule of the present invention is shown below.

KH-0001-GE11(5) is a single-stranded nucleic acid molecule in which GE11(5) as a peptide shown by the aforementioned SEQ ID NO: 14 is bonded, via a GMBS linker, to the linker region (Lx) of the aforementioned KH-0001 by the below-mentioned method.

KH-0001-GE11(5) (SEQ ID NOs: 29 (guide strand) and 37 (passenger strand))

[Chem. KH01GE11 (5)]

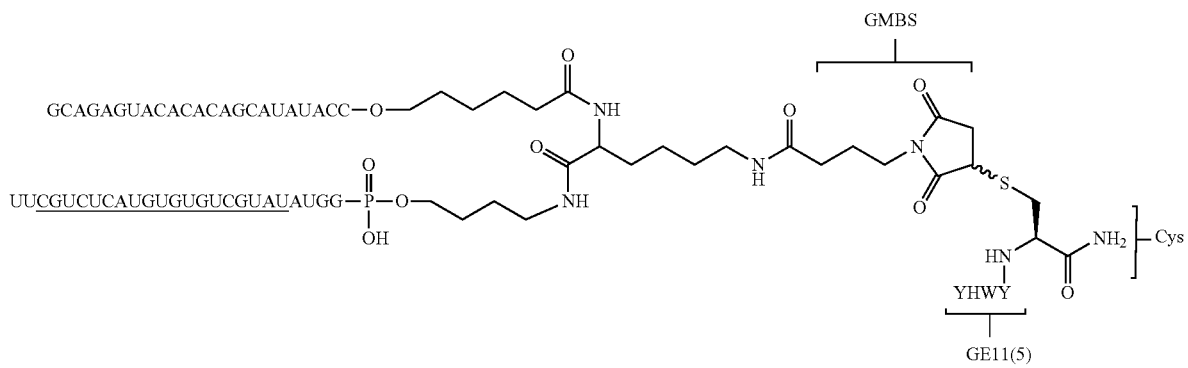

Synthesis of KH-0001-GE11(5)

Figure 10:
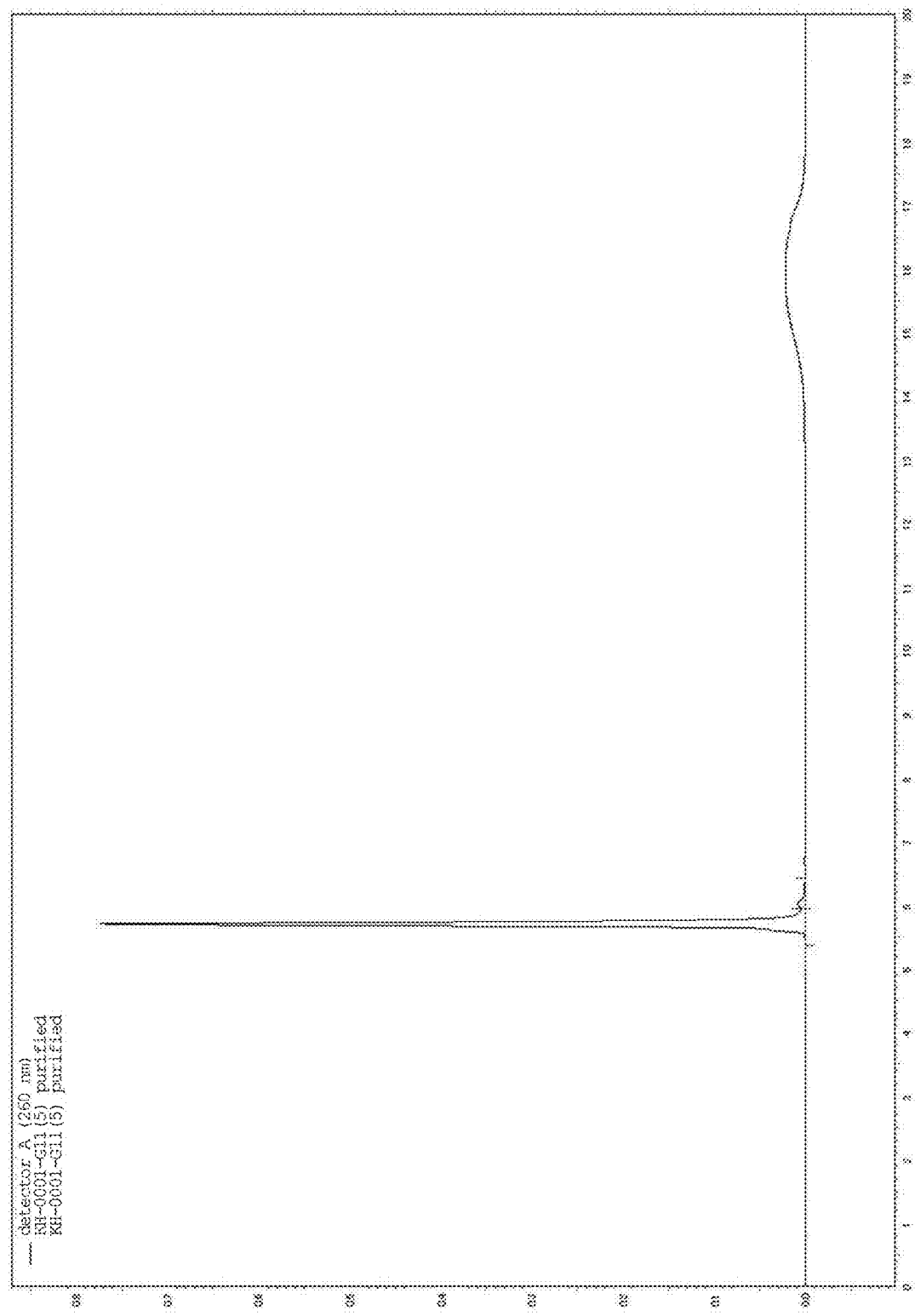
FIG. 10 is an HPLC chart of a GE11(5)-conjugated single-stranded nucleic acid molecule after purification in an Example of the present invention.

500 μmol/L KH-0001 (800 μL), 4 mmol/L GMBS/DMF solution (2000 μL), 1 mol/L phosphate buffer (pH 7.0) (480 μL), and distilled water for injection (720 μL) were mixed, and the mixture was stirred at room temperature for 3 hr. The reaction mixture was purified by Sephadex G-25 (PD-10; GE Healthcare), and a ⅓ amount thereof was used for the next reaction. 1 mg of GE11(5) peptide was added in 100 mmol/L phosphate buffer (pH 7.0), and the mixture was stirred at room temperature for 1 hr. The reaction mixture was purified by HPLC (column: Develosil C8-UG-5, 5 μm, 10×50 mm; flow rate: 4.7 mL/min; detection: UV 260 nm; column oven: 35° C.; Buffer A: 50 mmol/L TEAA, 5% $CH_3CN$; Buffer B: $CH_3CN$) and the peak of the object product was separated. The separated fraction was subjected to ethanol precipitation and the resulting precipitate was dissolved in distilled water for injection (Otsuka Pharmaceutical Co., Ltd.). The absorbance at UV 260 nm was measured and the yield was calculated to give KH-0001-GE11(5) (1.1 mg) having a purity of 98.09%. Mass spectrometry: 16657.49 (Calculated: 16657.54). An HPLC chart after purification is shown in FIG. 10.

Example B1: Gene Expression Inhibitory Effect of Lipid-Conjugated Single-Stranded Nucleic Acid Molecule The TGF-β1 gene expression inhibitory effect of lipid-conjugated single-stranded nucleic acid molecule KH-0001-C18 having an expression inhibitory sequence targeting TGF-β1 gene, which is synthesized in the aforementioned Example A1, and conjugate-free single-stranded nucleic acid molecule PH-0009 as Comparative Example was examined.

Each of the aforementioned single-stranded nucleic acid molecules was dissolved in distilled water for injection (Otsuka Pharmaceutical Co., Ltd.) to prepare a single-stranded nucleic acid molecule solution.

As the cells, A549 cells (DS Pharma Biomedical Co., Ltd.) were used. As the medium, DMEM (Invitrogen) containing 10% FBS was used. The culture conditions were 37° C., 5% $CO_2$.

First, the cells were cultured in the aforementioned medium, and the culture solution was dispensed to a 24-well plate such that each well contained 400 μL of the culture solution to achieve a density of $4\times10^4$ cells/well. The cells in the aforementioned well were transfected with the aforementioned single-stranded nucleic acid molecule by using a transfection reagent RNAiMAX (Invitrogen) according to the protocol of the aforementioned transfection reagent. Specifically, the transfection was carried out by setting the composition per well as follows. In the following composition, (A) is the aforementioned transfection reagent, (B) is Opti-MEM (Invitrogen), (C) is the aforementioned single-stranded nucleic acid molecule solution, and 98.5 μL of (B) and (C) in combination was added. In the aforementioned well, the final concentration of the aforementioned single-stranded nucleic acid molecule was 0.01, 0.1, 1 nmol/L.

TABLE 1

| (composition per well: μL) | |
|---|---|
| culture solution | 400 |
| (A) | 1.5 |
| (B) and (C) | 98.5 |
| total | 500 |

After the transfection, the cells in the aforementioned wells were cultured for 24 hours, and then, the RNA was collected using an RNeasy Mini Kit (Qiagen, Netherlands) according to the protocol supplied therewith. Subsequently, cDNA was synthesized from the aforementioned RNA using a reverse transcriptase (trade name: SuperScript III, Invitrogen) according to the protocol supplied therewith. Then, as shown below, PCR was carried out using the aforementioned synthesized cDNA as a template, and the expression level of the TGF-β1 gene and that of the β-actin gene as an internal standard were measured. The aforementioned expression level of the TGF-β1 gene was normalized with reference to that of the β-actin gene mentioned above.

The aforementioned PCR was carried out using a LightCycler FastStart DNA Master SYBR Green I (trade name, Roche) as a reagent and a Light Cycler DX400 (trade name, Roche) as an instrument (hereinafter the same). The aforementioned TGF-β1 gene and β-actin gene were amplified using the following primer sets, respectively.

```
PCR primer set for TGF-β1 gene
                              (SEQ ID NO: 33)
5'-TTGTGCGGCAGTGGTTGAGCCG-3'

(SEQ ID NO: 34)
5'-GAAGCAGGAAAGGCCGGTTCATGC-3' primer set for β-actin gene
                              (SEQ ID NO: 35)
5'-GCCACGGCTGCTTCCAGCTCCTC-3'

(SEQ ID NO: 36)
5'-AGGTCTTTGCGGATGTCCACGTCAC-3'
```

As control 1, regarding the cells in the aforementioned culture solution to which 100 μL of the aforementioned solution (B) alone was added, the expression levels of the genes also were measured (-). Furthermore, as control 2, regarding the cells subjected to the same transfection procedures as in the above except that the aforementioned RNA solution was not added and that the aforementioned (B) and 1.5 μL of the aforementioned (A) were added so that the total amount of (A) and (B) would be 100 μL, the expression level of the gene also was measured (mock).

As for the normalized expression level of the TGF-β1 gene, the relative value in the cell introduced with each single-stranded nucleic acid molecule was determined based on the expression level in the cells of the control (-) set as 1.

Figure 11:
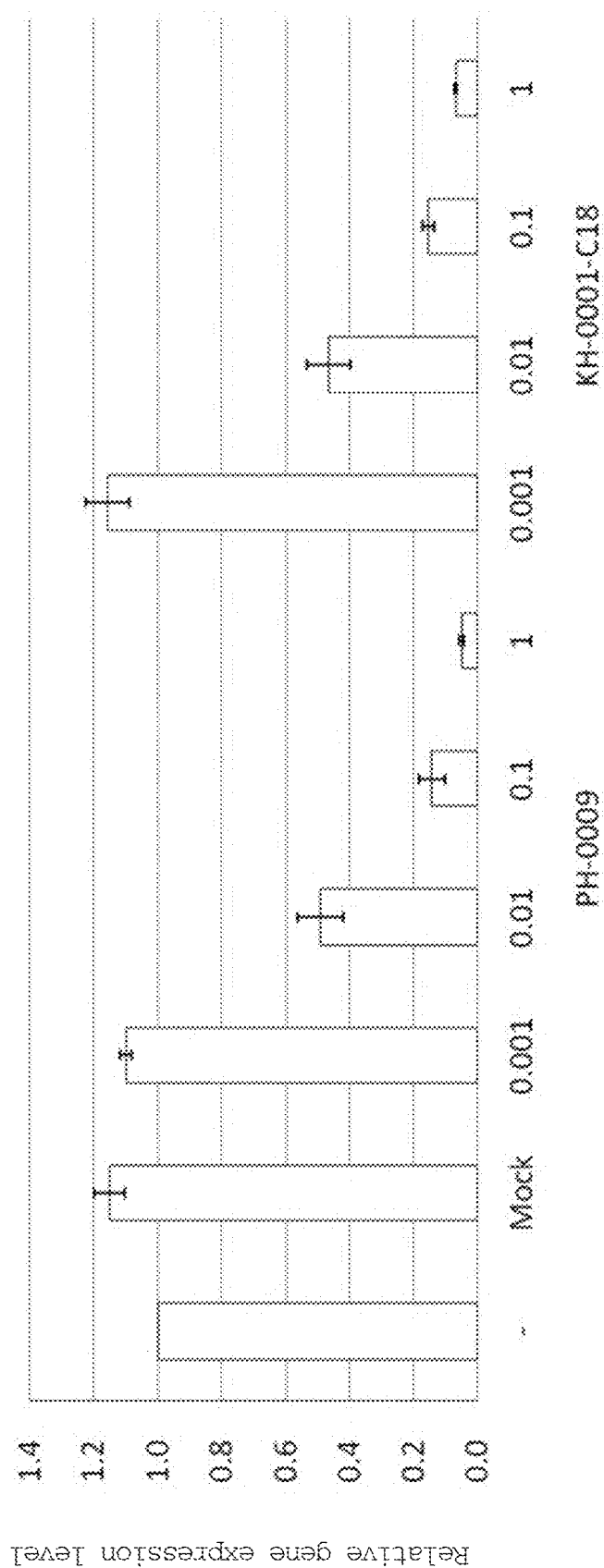
FIG. 11 is a graph showing relative values of TGF-β1 gene expression level in an Example of the present invention.

The results thereof are shown in FIG. 11. FIG. 11 is a graph showing the relative expression level of the TGF-β1 gene, and the vertical axis indicates the relative gene expression level. As shown in FIG. 11, KH-0001-C18 was found to have a strong gene expression inhibitory activity of the same level as PH-0009.

Example B2: Gene Expression Inhibitory Effect on Lipid-Conjugated Single-Stranded Nucleic Acid Molecule, Carbohydrate-Conjugated Single-Stranded Nucleic Acid Molecule and Peptide-Conjugated Single-Stranded Nucleic Acid Molecule TGF-β1 gene expression inhibitory effect of the following lipid-conjugated single-stranded nucleic acid molecule, carbohydrate-conjugated single-stranded nucleic acid molecule and peptide-conjugated single-stranded nucleic acid molecule synthesized in the aforementioned Example A1 and having an expression inhibitory sequence targeting TGF-β1 gene was studied. As the lipid-conjugated single-stranded nucleic acid molecule, KH-0001-C18, KH-0001-DOPE, KH-0001-Cho1 and KH-0030 were used, KH-0001-Lac, KH-0001-GalNAc and KH-0001-GlcNAc were used as the carbohydrate-conjugated single-stranded nucleic acid molecule, and KH-0001-GE11, KH-0001-GE11(7) and KH-0001-GE11(5) were used as the peptide-conjugated single-stranded nucleic acid molecule. As the negative control, PH-0000 was used, and KH-0001 and PH-0009, which are single-stranded nucleic acid molecules free of a conjugate, were used the Comparative Example.

In the consideration of the gene expression inhibitory effect of lipid-conjugated single-stranded nucleic acid molecule and peptide-conjugated single-stranded nucleic acid molecule, A549 cells (DS Pharma Biomedical Co., Ltd.) were used. In the consideration of the gene expression inhibitory effect of carbohydrate-conjugated single-stranded nucleic acid molecule, HepG2 cells (DS Pharma Biomedical Co., Ltd.) were used. As the medium, DMEM (Invitrogen) containing 10% FBS was used. The culture conditions were 37° C., 5% $CO_2$.

By a method similar to that of Example B1 except the following points, the gene expression level was measured. As reverse transcriptase, Transcriptor First Strand cDNA Synthesis Kit (trade name, Roche) was used, LightCycler480 SYBR Green I Master (trade name, Roche) was used as a reagent of PCR, and Light Cycler480 Instrument II (trade name, Roche) was used as an instrument for PCR. The final concentration of carbohydrate-conjugated single-stranded nucleic acid molecule and peptide-conjugated single-stranded nucleic acid molecule was set to 0.1 and 1 nmol/L, respectively, and the final concentration of the lipid-conjugated single-stranded nucleic acid molecule was set to 1 nmol/L.

As for the expression level of TGF-β1 gene after amendment, the relative value of the expression level in the cells introduced with each single-stranded nucleic acid molecule was determined with the expression level of the cells in control 2 (mock) as 1.

Figure 12:
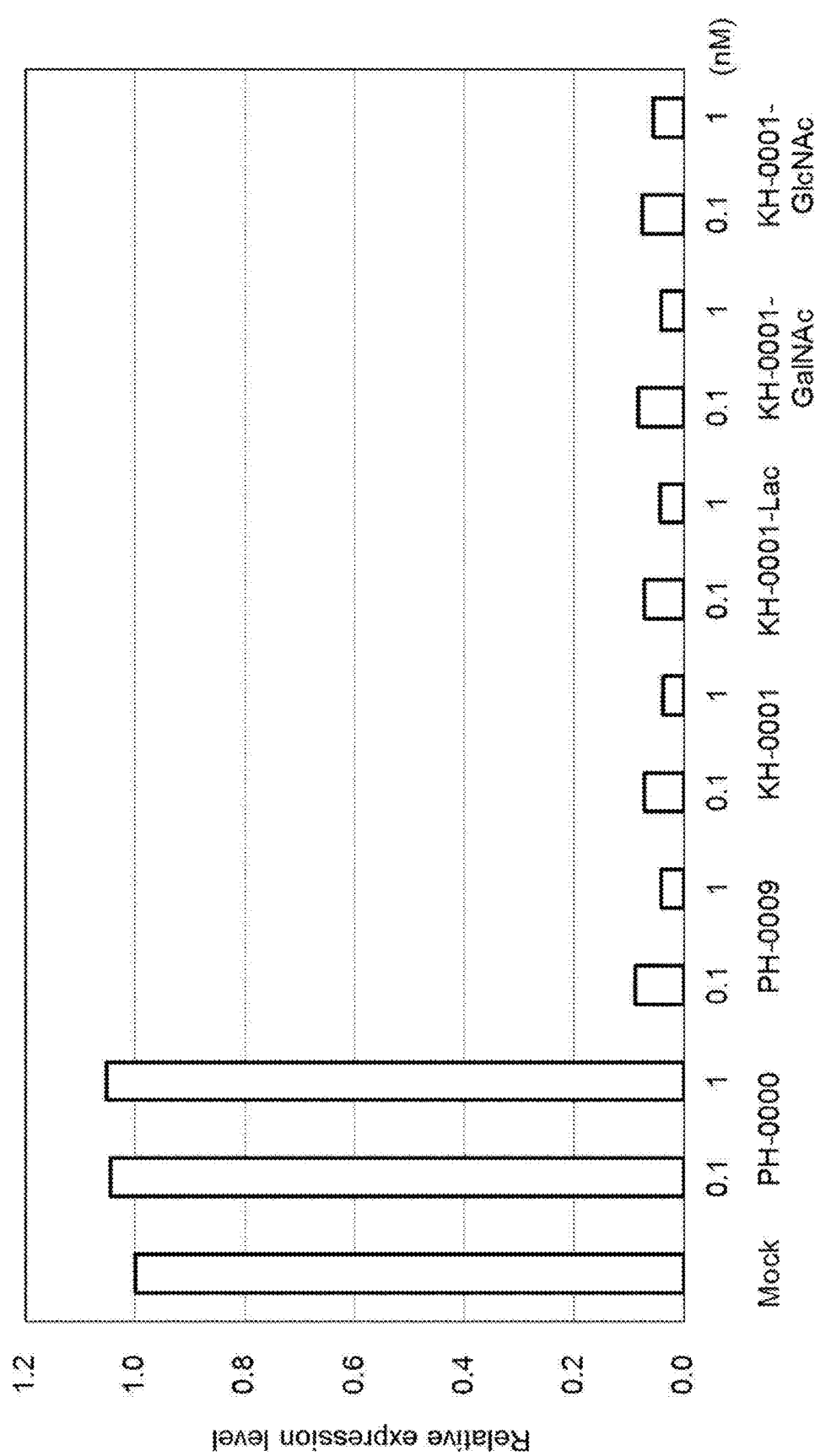
FIG. 12 is a graph showing relative values of TGF-β1 gene expression level in an Example of the present invention.
Figure 13:
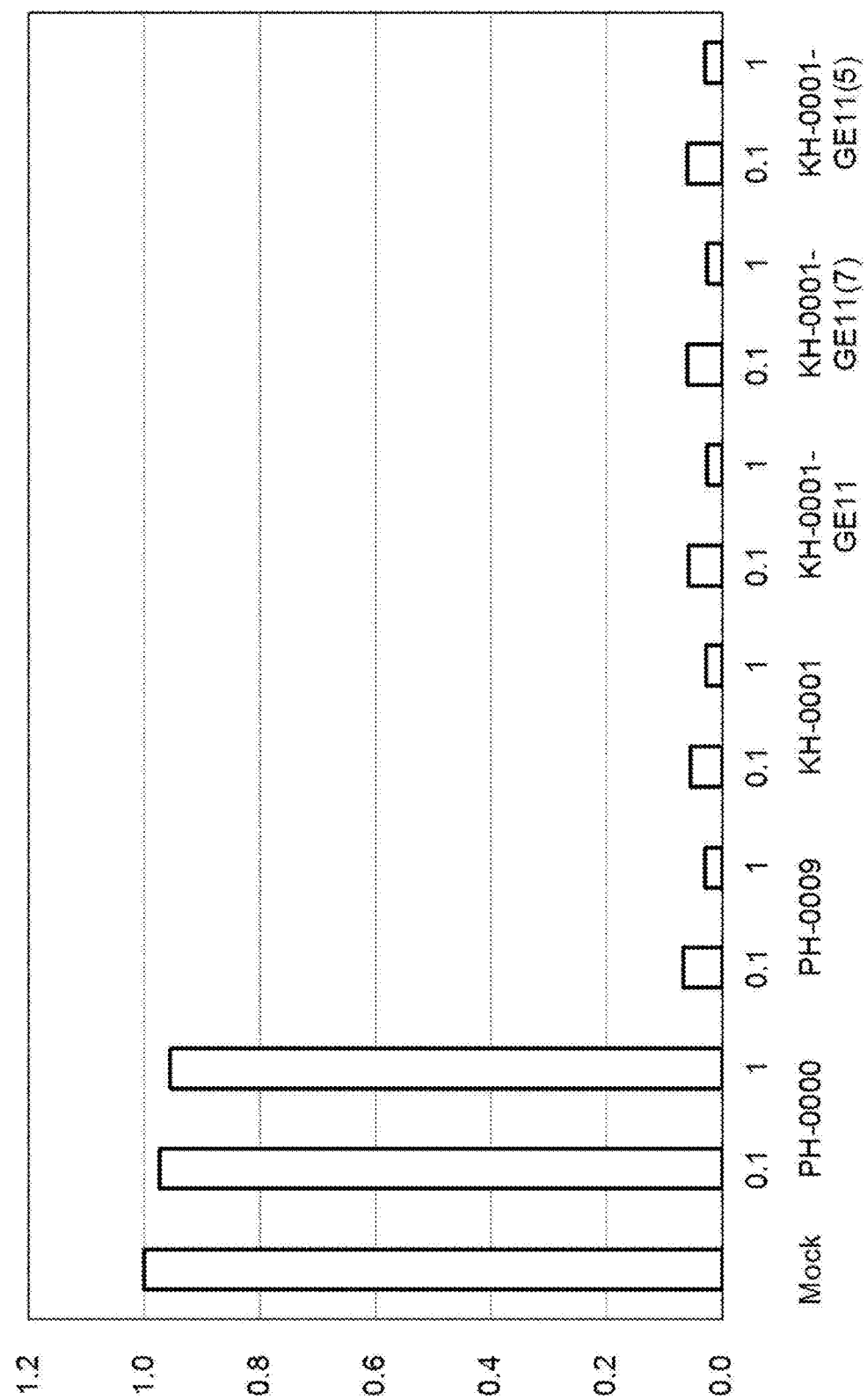
FIG. 13 is a graph showing relative values of TGF-β1 gene expression level in an Example of the present invention.
Figure 14:
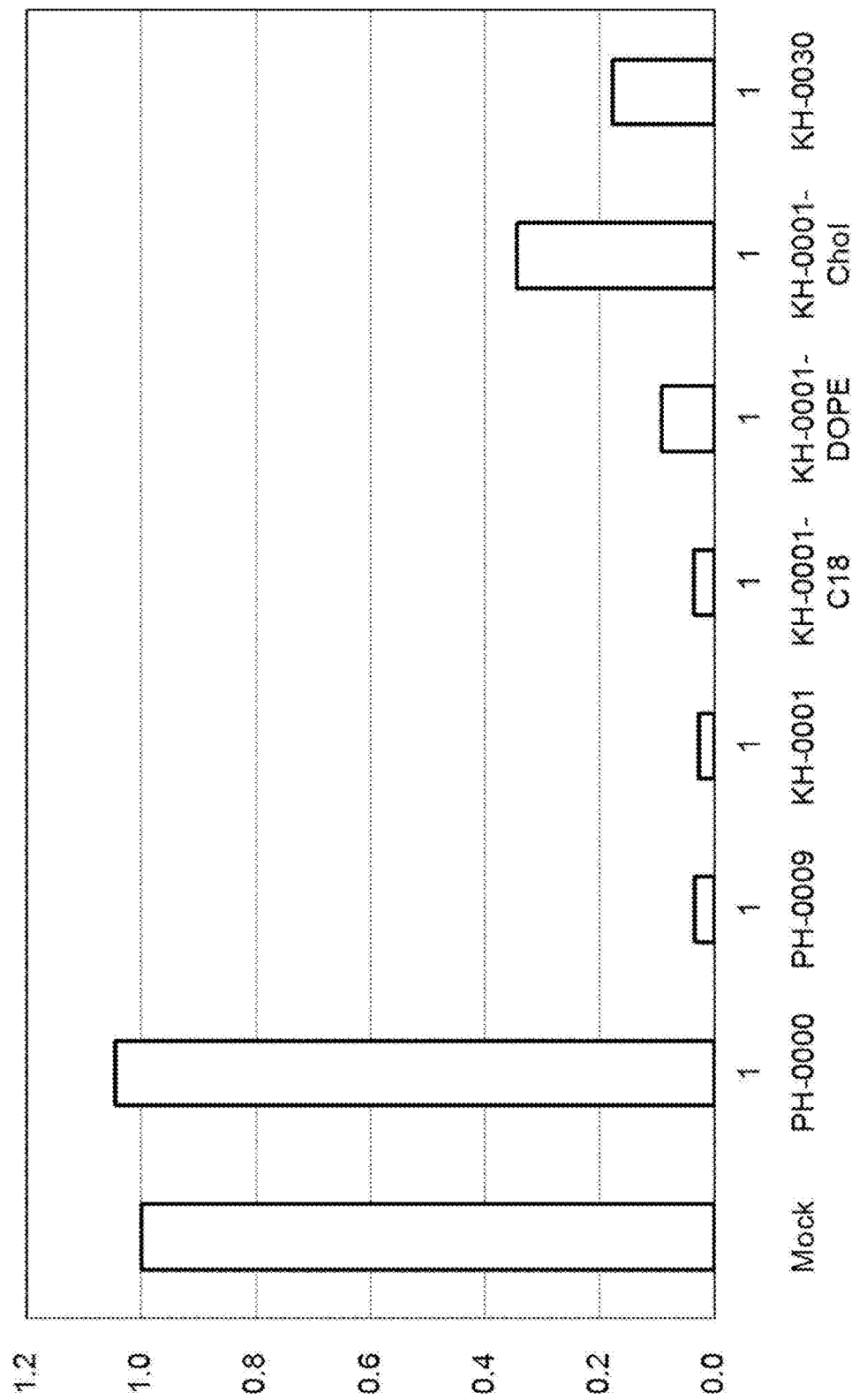
FIG. 14 is a graph showing relative values of TGF-β1 gene expression level in an Example of the present invention.

The results thereof are shown in FIGS. 12-14. Each Figure is a graph showing the relative value of TGF-β1 gene expression level, wherein the vertical axis shows relative gene expression level. FIG. 12 shows the results of carbohydrate-conjugated single-stranded nucleic acid molecule, FIG. 13 shows the results of peptide-conjugated single-stranded nucleic acid molecule, and FIG. 14 shows the results of lipid-conjugated single-stranded nucleic acid molecule. As shown in FIG. 12, all carbohydrate-conjugated single-stranded nucleic acid molecules showed a strong gene expression inhibitory activity of the same level as that of KH-0001 and PH-0009. As shown in FIG. 13, all peptide-conjugated single-stranded nucleic acid molecules showed a strong gene expression inhibitory activity of the same level as that of KH-0001 and PH-0009. As shown in FIG. 14, KH-0001-C18 showed a strong gene expression inhibitory activity of the same level as that of KH-0001 and PH-0009. The relative gene expression level of KH-0001-DOPE, KH-0001-Chol and KH-0030 was 0.1-0.35, thus showing a gene expression inhibitory activity.

Example C1: Reactivity of Lipid-Conjugated Single-Stranded Nucleic Acid Molecule with Dicer Protein The lipid-conjugated single-stranded nucleic acid molecule KH-0001-C18 synthesized in the aforementioned Example A1, and conjugate-free single-stranded nucleic acid molecule PH-0009 and single-stranded nucleic acid molecule NH-0005 in which linker region Lx consists of nucleotide residues alone, each of Comparative Example, were studied for the reactivity with Dicer protein.

Using Recombinant Human Dicer Enzyme Kit (trade name, Genlantis) as a reagent, and according to the attached protocol, a reaction mixture containing the aforementioned Dicer protein and the aforementioned nucleic acid molecule was prepared, and this was incubated at 37° C. The incubate time was set to 0, 2, 6, 24, 48, 72 hr. To the aforementioned reaction mixture after incubation for a given time was added a reaction quenching liquid of the aforementioned reagent, and the mixture was subjected to 7 M urea-20% polyacrylamide gel electrophoresis. Thereafter, the aforementioned polyacrylamide gel was stained with SYBR Green II (trade name, Lonza), and analyzed using ChemiDoc (trade name, Bio-Rad).

Figure 15:
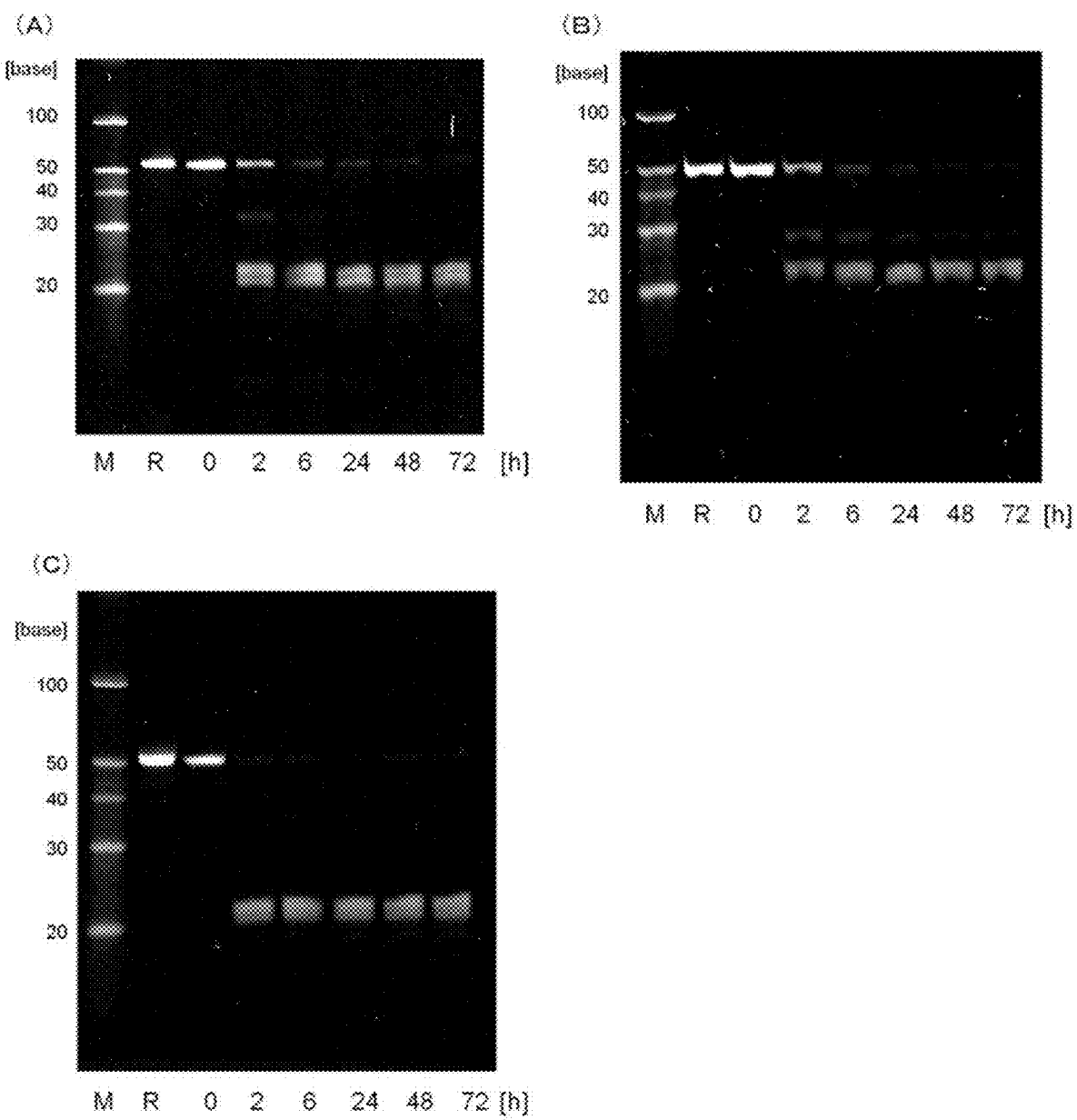
FIG. 15 shows the results of electrophoresis showing the reactivity with Dicer protein in an Example of the present invention.

The results thereof are shown in FIG. 15. FIG. 15(A) shows the results of electrophoresis showing the reactivity of NH-0005 with Dicer protein, FIG. 15(B) shows the results of electrophoresis showing the reactivity of PH-0009 with Dicer protein, and FIG. 15(C) shows the results of electrophoresis showing the reactivity of KH-0001-C18 with Dicer protein. In each Figure, lane "M" is a molecular weight marker (20, 30, 40, 50 and 100 bases), (h) is the time of the aforementioned incubation, and R is an untreated sample.

Conjugate-free PH-0009 and NH-0005 in which linker region consists of natural nucleotide, each of Comparative Example, gradually reacted with the aforementioned Dicer protein and the reaction continued until after 6 hr. In contrast, KH-0001-C18 having a lipid conjugate rapidly reacted with the aforementioned Dicer and the reaction was completed 2 hr later. To examine the reactivity of KH-0001-C18 with Dicer protein in detail, the incubate time was set to 0, 5, 10, 30, 60, 90, 120 min, and the reaction and analysis was performed in the same manner.

Figure 16:
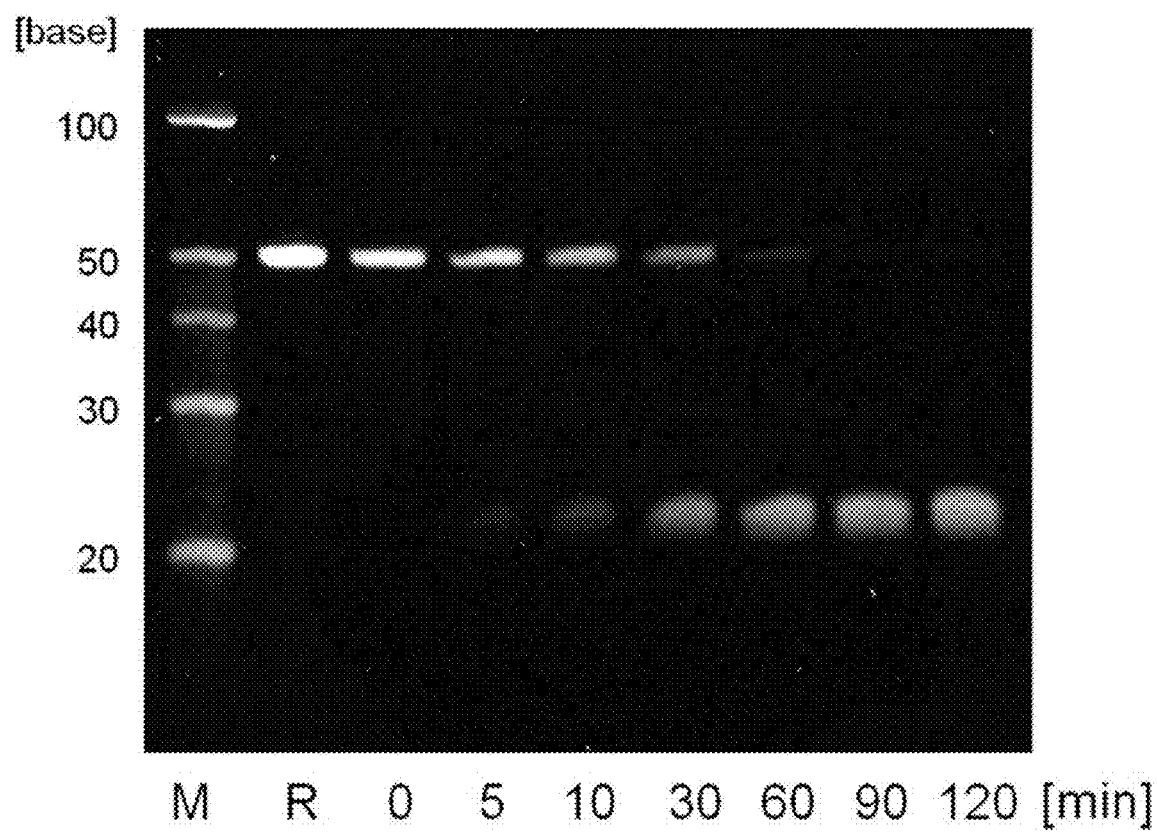
FIG. 16 shows the results of electrophoresis showing the reactivity with Dicer protein in an Example of the present invention.

The results thereof are shown in FIG. 16. Lane "M" is a molecular weight marker (20, 30, 40, 50 and 100 bases), (min) is the aforementioned incubation time (min), and R is an untreated sample. As shown in FIG. 16, KH-0001-C18 rapidly reacted with Dicer protein and the reaction was completed 60 min later.

From the above results, it was found that the reactivity of the lipid-conjugated single-stranded nucleic acid molecule of the present invention with Dicer protein was markedly improved. That is, when considered together with the results of gene expression inhibitory effect of the aforementioned Example B1, the lipid-conjugated single-stranded nucleic acid molecule of the present invention is considered to potentially have an ability to rapidly exert an RNA interfering effect after being introduced into the cell.

Example C2: Stability of Lipid-Conjugated Single-Stranded Nucleic Acid Molecule in Human Serum The lipid-conjugated single-stranded nucleic acid molecule KH-0001-C18 synthesized in the aforementioned Example A1, and conjugate-free single-stranded nucleic acid molecule PH-0009 and single-stranded nucleic acid molecule NH-0005 in which linker region Lx consists of nucleotide residues alone, each of Comparative Example, were studied for the stability in human serum.

First, a mixture (30 µL) of the aforementioned single-stranded nucleic acid molecule and normal human serum (MP Biomedicals) in 1×PBS was incubated at 37° C. In the aforementioned mixture (30 µL), the amount of the aforementioned single-stranded nucleic acid molecule was set to 60 µmol, and the amount of the aforementioned normal human serum was set to a final concentration of 10%. At 0 hr, 1 hr, 3 hr, 5 hr and 24 hr after the start of the incubation, the mixture was heat-treated at 95° C. for 10 min and rapidly cooled in ice to discontinue the reaction. Thereafter, the RNA fraction was extracted according to the Bligh&Dyer method (http://biochem2.umin.jp/contents/Manuals/manual54.html). The obtained extract was subjected to 7 M urea-20% polyacrylamide gel electrophoresis, stained with SYBR Green II (trade name, Lonza) and analyzed using ChemiDoc (trade name, Bio-Rad).

Figure 17:
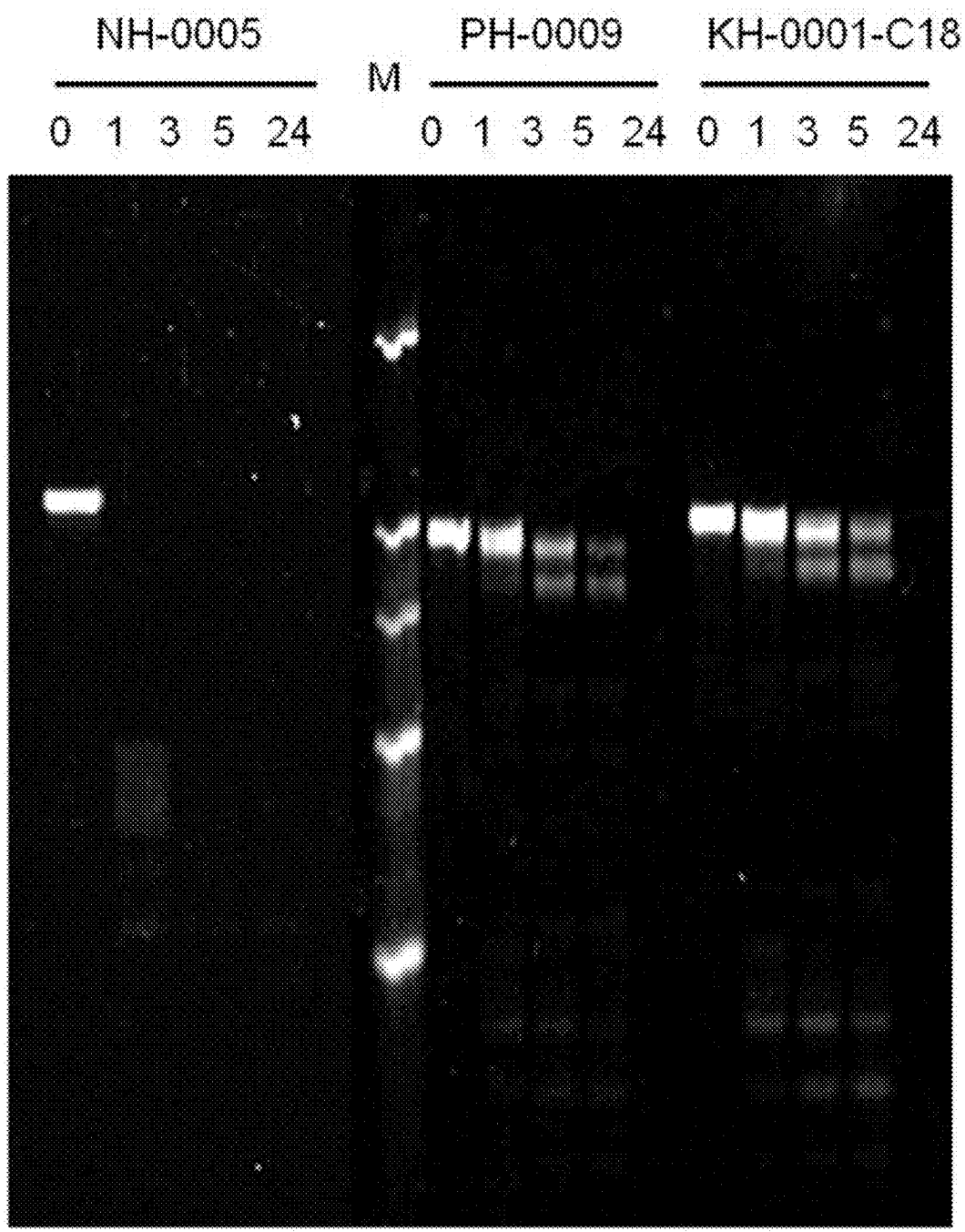
FIG. 17 shows the results of electrophoresis showing stability in an Example of the present invention.

The results thereof are shown in FIG. 17. In FIG. 17, lane "M" is a molecular weight marker, and (h) is an incubation time.

As shown in FIG. 17, it was confirmed that NH-0005 of Comparative Example in which linker region Lx consists of a nucleotide residues alone showed rapid progress of a decomposition reaction and complete decomposition was achieved 1 hr after incubation. In contrast, KH-0001-C18 of the present invention showed decomposition as mild as PH-0009 of the Comparative Example, and did not show complete decomposition even at 5 hr after the reaction.

From the results of the aforementioned Example B1, the aforementioned Example B2, the aforementioned Example C1, and the aforementioned Example C2, the lipid-conjugated single-stranded nucleic acid molecule of the present invention is considered to have stability in the body and potentially have an ability to rapidly exert an RNA interfering effect after being introduced into the cell.

Reference Example 1: Synthesis of Lys Amidite

According to the following scheme 6, DMTr-Lys amidite (7) which is a lysine (Lys) amidite, was synthesized. In the following scheme 6, "Tfa" is a trifluoroacetyl group.

scheme 6

[Chem. S6]

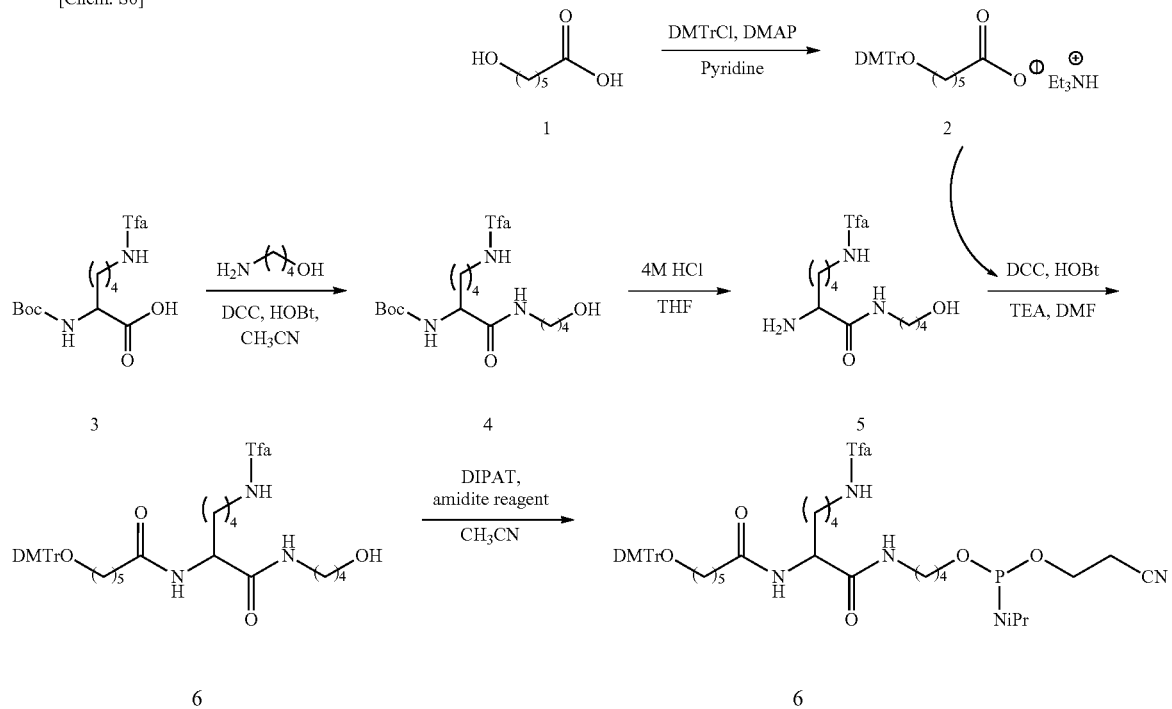

(1) Synthesis of Compound 2

To a pyridine solution (124 mL) of 6-hydroxyhexanoic acid (6 g, 15.1 mmol) were added 4,4'-dimethoxytrityl chloride (20 g, 1.3 eq.) and dimethylaminopyridine (0.5 g, 0.1 eq.), and the mixture was stirred at room temperature for 20 hr. After completion of the reaction, methanol (10 mL) was added, the mixture was stirred for 10 min, and the solvent was evaporated. The reaction liquid was diluted with ethyl acetate, washed three times with TEAA buffer (pH 8-9), and washed once with saturated brine. The organic layer was dried over sodium sulfate, and the solvent was evaporated under reduced pressure to give compound 2 (31 g, pyridine-containing) as a pale-yellow oil.

(2) Synthesis of Compound 4

To an acetonitrile solution (45 mL) of compound 3 (2.7 g, 7.9 mmol), dicyclohexylcarbodiimide (1.9 g, 1.2 eq.), and 1-hydroxybenzotriazole monohydrate (2.6 g, 2.4 eq.) was added an acetonitrile solution (5 mL) of 4-amino-1-butanol (0.86 g, 1.2 eq.), and the mixture was stirred at room temperature for 16 hr. After completion of the reaction, the precipitate was collected by filtration, and the solvent in the filtrate was evaporated by an evaporator. Dichloromethane was added to the obtained residue, and the mixture was washed three times with acetate buffer (pH 4) and three times with saturated aqueous sodium bicarbonate. The organic layer was dried over sodium sulfate, and the solvent was evaporated under reduced pressure. The obtained crude product was purified by silica gel column chromatography (eluent: dichloromethane/methanol=10/1) to give compound 4 (2.8 g, yield 85%) as a white solid. The instrumental analytical values of compound 4 are shown below.

compound 4;

$^1$H-NMR (400 MHz, CDCl$_3$) δ: 7.07 (br, 1H), 6.72 (t, J=5.6 Hz, 1H), 4.03 (m, 1H), 3.66 (d, J=4.9 Hz, 2H), 3.37 (dd, J=12.9, 6.3 Hz, 2H), 3.29 (dd, J=12.4, 6.3 Hz, 2H), 1.83 (s, 2H), 1.66-1.60 (m, 6H), 1.44 (s, 9H), 1.41-1.37 (m, 2H)

(3) Synthesis of Compound 5

Compound 4 (2.5 g, 6.1 mmol) was stirred in hydrochloric acid/tetrahydrofuran solution (4 M, 45 mL) at room temperature for 2 hr. After completion of the reaction, the solvent was evaporated under reduced pressure. The obtained residue was dissolved in ethanol, and azeotroped with toluene. The solvent was evaporated to give compound 5 (1.9 g) as a white solid. The instrumental analytical values of compound 5 are shown below.

compound 5;

$^1$H-NMR (400 MHz, CD$_3$OD) δ: 3.85-3.81 (m, 1H), 3.59-3.56 (m, 2H), 3.32-3.20 (m, 2H), 1.94-1.80 (m, 2H), 1.66-1.58 (m, 6H), 1.46-1.40 (m, 2H)

(4) Synthesis of Compound 6

To a solution (150 mL) of compound 2 (pyridine-containing, 24 g, 35.5 mmol), dicyclohexylcarbodiimide (8.8 g, 1.2 eq.), and 1-hydroxybenzotriazole monohydrate (7.2 g, 1.5 eq.) was added triethylamine (4.5 mL, 0.9 eq.), an N,N-dimethylformamide solution (30 mL) of compound 5 (10 g, 0.9 eq.) was further added, and the mixture was stirred at room temperature for 20 hr. After completion of the reaction, the precipitate was collected by filtration, and the solvent in the filtrate was evaporated by an evaporator. Dichloromethane was added to the obtained residue, and the mixture was washed three times with saturated aqueous sodium bicarbonate. The organic layer was dried over sodium sulfate, and the solvent was evaporated under reduced pressure. The obtained crude product was purified by silica gel column chromatography (eluent: dichloromethane/methanol=20/1+0.05% pyridine) to give compound 6 (16 g, yield 70%) as a pale-yellow solid. The instrumental analytical values of compound 6 are shown below.

compound 6;

¹H-NMR (400 MHz, CDCl₃) δ: 7.43-7.40 (m, 2H), 7.32-7.26 (m, 6H), 7.21-7.17 (m, 1H), 6.81 (d, J=8.8 Hz, 4H), 4.39-4.37 (m, 1H), 3.78 (s, 6H), 3.64-3.61 (m, 2H), 3.33-3.22 (m, 4H), 3.03 (t, J=6.6 Hz, 2H), 2.19 (t, J=7.6 Hz, 2H), 1.79-1.54 (m, 12H), 1.40-1.34 (m, 4H)

(5) Synthesis of Compound 7

To an anhydrous acetonitrile solution (3.5 mL) of the starting material (1.26 g, 1.73 mmol), which was azeotropically dried by acetonitrile, were added diisopropylammonium tetrazolide (394 mg, 1.3 eq.) and 2-cyanoethoxy-N,N,N',N'-tetraisopropyl phosphorodiamidite (700 mg, 1.3 eq.), and the mixture was stirred at room temperature for 2.5 hr. Dichloromethane was added, the mixture was washed with saturated aqueous sodium bicarbonate and saturated brine and dried over sodium sulfate, and the solvent was evaporated. The obtained crude product was purified by silica gel column chromatography (amino silica, eluent: n-hexane/ethyl acetate=2/3) to give compound 7 (1.3 g, yield 78%) as a white solid. The instrumental analytical values of compound 7 are shown below.

compound 7;

¹H-NMR (400 MHz, CDCl₃) δ: 7.43-7.41 (m, 2H), 7.32-7.17 (m, 7H), 6.81 (dt, J=9.3, 2.9 Hz, 4H), 4.42-4.37 (m, 1H), 3.78 (s, 6H), 3.88-3.54 (m, 6H), 3.32-3.20 (m, 4H), 3.03 (t, J=6.3 Hz, 2H), 2.19 (t, J=7.6 Hz, 2H), 1.83-1.53 (m, 12H), 1.42-1.31 (m, 4H), 1.28-1.24 (m, 2H), 1.18-1.16 (m, 12H) ³¹P-NMR (162 MHz, CDCl₃) δ: 146.9

Reference Example 2: Synthesis of Gly Amidite

According to the following scheme 7, DMTr-Gly amidite (compound 12) which is a glycine (Gly) amidite, was synthesized.

scheme 7

[Chem. S7]

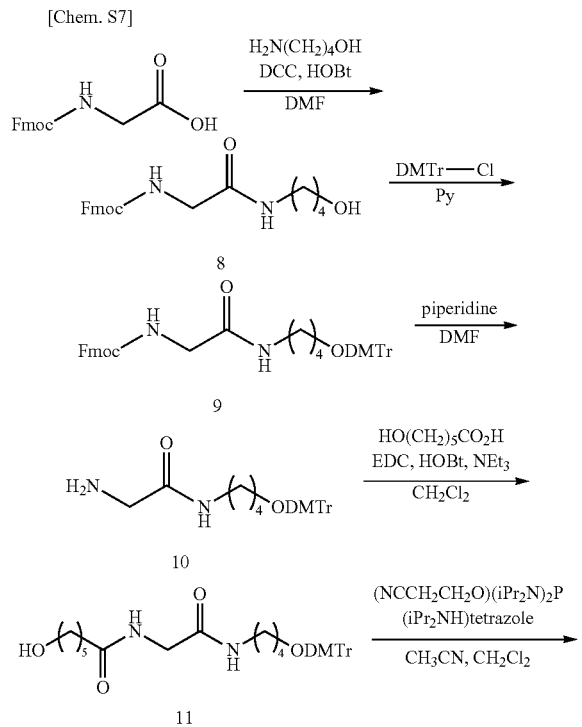

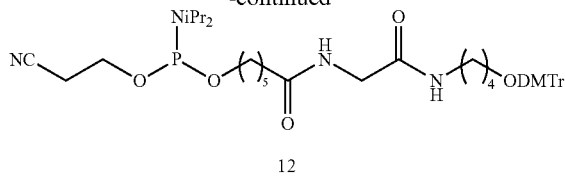

(1) N-(4-hydroxybutyl)-N$^α$-Fmoc-glycinamide (compound 8)

To an anhydrous N,N-dimethylformamide solution (100 mL) of Fmoc-glycine (4.00 g, 13.45 mmol), dicyclohexylcarbodiimide (3.33 g, 16.15 mmol) and 1-hydroxybenzotriazole monohydrate (4.94 g, 32.29 mmol) was added an anhydrous N,N-dimethylformamide solution (30 mL) of 4-aminobutanol (1.44 g, 16.15 mmol), and the mixture was stirred at room temperature overnight under an argon atmosphere. The resultant precipitate was separated by filtration, and the filtrate was concentrated under reduced pressure. Dichloromethane (200 mL) was added to the obtained residue, and the mixture was washed three times with saturated aqueous sodium bicarbonate, and further washed with saturated brine. After drying over sodium sulfate, the solvent was evaporated under reduced pressure. The obtained residue was subjected to silica gel column chromatography (eluent: dichloromethane-methanol (95:5) to give N-(4-hydroxybutyl)-N$^α$-Fmoc-glycinamide (8) (4.30 g, 87%). The instrumental analytical values of N-(4-hydroxybutyl)-N$^α$-Fmoc-glycinamide (8) are shown below.

N-(4-hydroxybutyl)-N$^α$-Fmoc-glycinamide (8)

¹H-NMR (400 MHz, CDCl₃): δ=7.78-7.76 (2H, d, J=7.3 Hz), 7.65-7.63 (2H, d, J=7.3 Hz), 7.42-7.41 (2H, t, J=7.6 Hz), 7.34-7.30 (2H, td, J=7.6, 1.1 Hz), 4.42-4.40 (2H, d, J=7.3 Hz), 4.25-4.22 (1H, t, J=6.8 Hz), 3.83 (2H, s), 3.60-3.55 (2H, m), 3.30-3.25 (2H, m), 1.61-1.55 (4H, m).

(2) N-(4-O-DMTr-hydroxybutyl)-N$^α$-Fmoc-glycinamide (compound 9)

Compound 8 (4.20 g, 11.40 mmol) was azeotropically dried three times with anhydrous pyridine. 4,4'-Dimethoxytrityl chloride (5.80 g, 17.10 mmol) and anhydrous pyridine (80 mL) were added to the residue by azeotropy, and the mixture was stirred at room temperature overnight. Methanol (20 mL) was added to the obtained reaction mixture and the mixture was stirred at room temperature for 30 min, and the solvent was evaporated under reduced pressure. Thereafter, dichloromethane (200 mL) was added, and the mixture was washed three times with saturated aqueous sodium bicarbonate, and further washed with saturated brine. After drying over sodium sulfate, the solvent was evaporated under reduced pressure to give unpurified N-(4-O-DMTr-hydroxybutyl)-N$^α$-Fmoc-glycinamide (9) (11.40 g).

(3) N-(4-O-DMTr-hydroxybutyl)-glycinamide (compound 10)

To the unpurified compound 9 (11.40 g, 16.99 mmol) were added N,N-dimethylformamide (45 mL) and piperidine (11.7 mL) at room temperature, and the mixture was stirred at room temperature overnight. The solvent in the reaction mixture was evaporated under reduced pressure, and the obtained residue was subjected to silica gel column chromatography (eluent: dichloromethane-methanol (9:1)+0.05% pyridine) to give glycine-4,4'-dimethoxytrityloxybutanamide (3) (4.90 g, 96%, 2 steps). The instrumental analytical values of N-(4-O-DMTr-hydroxybutyl)-glycinamide (10) are shown below.

N-(4-O-DMTr-hydroxybutyl)-glycinamide (10)

$^1$H-NMR (400 MHz, CDCl$_3$): δ=7.44-7.42 (2H, m), 7.33-7.26 (6H, m), 7.21-7.20 (1H, m), 6.83-6.80 (4H, m), 3.79 (6H, s), 3.49 (2H, s), 3.30-3.28 (2H, t, J=6.3 Hz), 3.09-3.06 (2H, t, J=5.9 Hz), 1.61-1.55 (4H, m).

(4) N-(4-O-DMTr-hydroxybutyl)-N$^α$-(6-hydroxyhexanoyl)-glycinamide (compound 11)

Compound 10 (4.80 g, 10.70 mmol) was azeotropically dried three times with anhydrous pyridine, 6-hydroxyhexanoic acid (1.70 g, 12.84 mmol), 1-ethyl-3-(3-dimethylaminopropyl)carbodiimide hydrochloride (2.46 g, 12.84 mmol), 1-hydroxybenzotriazole monohydrate (3.93 g, 25.69 mmol), and anhydrous dichloromethane (60 mL) were added at room temperature under an argon atmosphere, and the mixture was stirred for 10 min. Triethylamine (3.90 g, 38.53 mmol) was added to the thus-obtained mixture, and the mixture was stirred at room temperature overnight under an argon atmosphere. Dichloromethane (200 mL) was added to the obtained reaction mixture, and the mixture was washed three times with saturated aqueous sodium bicarbonate, and further washed once with saturated brine. The organic layer was separated and dried over sodium sulfate, and the solvent was evaporated under reduced pressure. The obtained residue was subjected to silica gel column chromatography (eluent: dichloromethane-methanol (95:5)+0.05% pyridine) to give N-(4-O-DMTr-hydroxybutyl)-N$^α$-(6-hydroxyhexanoyl)-glycinamide (11) (4.80 g, 80%). The instrument analytical values of N-(4-O-DMTr-hydroxybutyl)-N$^α$-(6-hydroxyhexanoyl)-glycinamide (11) are shown below.

N-(4-O-DMTr-hydroxybutyl)-N$^α$-(6-hydroxyhexanoyl)-glycinamide (11)

$^1$H-NMR (400 MHz, CDCl$_3$): δ=7.43-7.40 (2H, m), 7.33-7.26 (6H, m), 7.22-7.20 (1H, m), 6.83-6.80 (4H, m), 3.85 (2H, s), 3.78 (6H, s), 3.63-3.60 (2H, t, J=6.3 Hz), 3.26-3.23 (2H, t, J=6.1 Hz), 3.07-3.05 (2H, t, J=5.6 Hz), 2.26-2.22 (2H, t, J=7.3 Hz), 1.68-1.52 (8H, m). 1.41-1.36 (2H, m).

(5) N-(4-O-DMTr-hydroxybutyl)-N$^α$-(6-O-(2-cyanoethyl-N,N-diisopropylphosphityl)-hydroxyhexanoyl)-glycinamide (compound 12)

Compound 11 (4.70 g, 8.35 mmol) was azeotropically dried three times with anhydrous pyridine. Then, diisopropylammonium tetrazolide (1.72 g, 10.02 mmol) was added, the mixture was deaerated under reduced pressure and filled with argon gas, and anhydrous acetonitrile (5 mL) was added. Furthermore, a solution (4 mL) of 2-cyanoethoxy-N,N,N',N'-tetraisopropyl phosphorodiamidite (3.02 g, 10.02 mmol) in a 1:1 anhydrous acetonitrile-dichloromethane mixture was added, and the mixture was stirred at room temperature for 4 hr under an argon atmosphere. Dichloromethane (150 mL) was added to the obtained reaction mixture, and the mixture was washed twice with saturated aqueous sodium bicarbonate, and further washed once with saturated brine. The organic layer was separated and dried over sodium sulfate, and the solvent was evaporated under reduced pressure. The obtained residue was subjected to column chromatography using amino silica (eluent: n-hexane-acetone (3:2)+0.1% triethylamine) to give hydroxyhexanoic acid amide glycine-4,4'-dimethoxytrityloxybutanamide phosphoramidite (12) (4.50 g, 71%, HPLC 98.2%). The instrumental analytical values of N-(4-O-DMTr-hydroxybutyl)-N$^α$-(6-O-(2-cyanoethyl-N,N-diisopropylphosphityl)-hydroxyhexanoyl)-glycinamide (12) are shown below.

N-(4-O-DMTr-hydroxybutyl)-N$^α$-(6-O-(2-cyanoethyl-N,N-diisopropylphosphityl)-hydroxyhexanoyl)-glycinamide (12)

$^1$H-NMR (400 MHz, CDCl$_3$): δ=7.43-7.40 (2H, m), 7.33-7.26 (6H, m), 7.22-7.20 (1H, m), 6.83-6.80 (4H, m), 3.85-3.81 (4H, s), 3.78 (6H, s), 3.63-3.61 (2H, t, J=6.3 Hz), 3.26-3.23 (2H, t, J=6.1 Hz), 3.05-2.97 (4H, m), 2.64-2.62 (2H, t, J=6.4 Hz), 2.25-2.23 (2H, t, J=7.3 Hz), 1.68-1.52 (8H, m), 1.40-1.38 (2H, m), 1.13-1.20 (12H, m). $^{31}$P-NMR (162 MHz, CDCl$_3$): δ=146.57.

Reference Example 3: Synthesis of Proline Amidite

According to the following scheme 8, compound 17, which is an amidite containing a proline skeleton, was synthesized.

scheme 8

[Chem. S8]

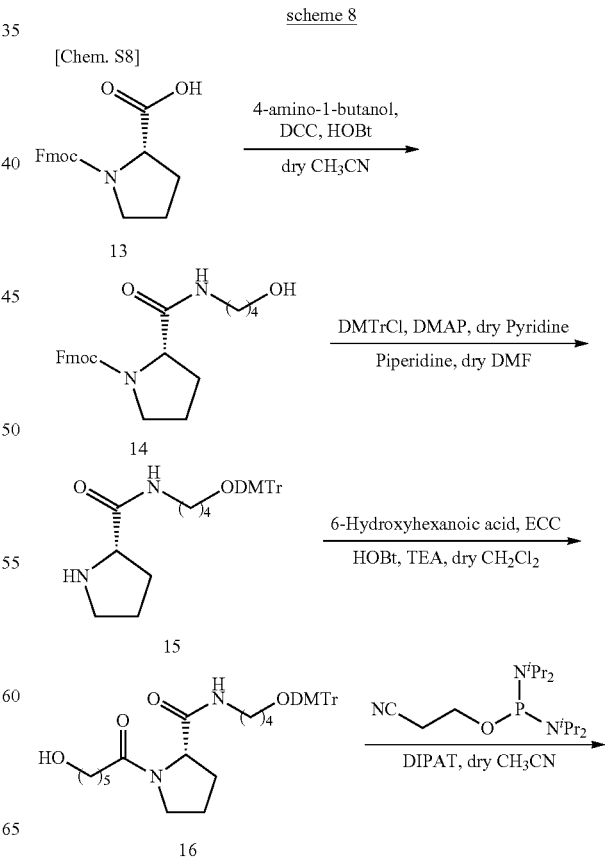

-continued

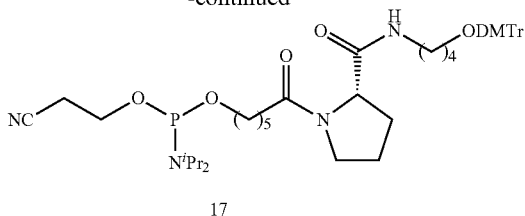

17

(1) N-(4-hydroxybutyl)-N^α-Fmoc-L-prolinamide (compound 14)

Compound 13 (Fmoc-L-proline) was used as a starting material. The aforementioned compound 13 (10.00 g, 29.64 mmol), 4-amino-1-butanol (3.18 g, 35.56 mmol), and 1-hydroxybenzotriazole (10.90 g, 70.72 mmol) were mixed together. The aforementioned mixture was deaerated under reduced pressure and filled with argon gas. Anhydrous acetonitrile (140 mL) was added to the aforementioned mixture at room temperature, and a solution (70 mL) of dicyclohexylcarbodiimide (7.34 g, 35.56 mmol) in anhydrous acetonitrile was further added thereto. Thereafter, this was stirred for 15 hours at room temperature under an argon atmosphere. After the completion of the reaction, the generated precipitate was removed by filtration, and the solvent in the collected filtrate was evaporated under reduced pressure. Dichloromethane (200 mL) was added to the obtained residue, and the mixture was washed with saturated aqueous sodium bicarbonate (200 mL). Then, an organic layer was collected and dried over magnesium sulfate. Thereafter, the aforementioned organic layer was filtered, and the solvent in the obtained filtrate was evaporated under reduced pressure. Diethyl ether (200 mL) was added to the residue, thereby turning the residue to powder. The thus-obtained powder was collected by filtration. Thus, compound 14 in the form of colorless powder was obtained (10.34 g, yield 84%). The instrument analytical values of the aforementioned compound 14 are shown below.

compound 14:
$^1$H-NMR (CDCl$_3$): δ7.76-7.83 (m, 2H, Ar—H), 7.50-7.63 (m, 2H, Ar—H), 7.38-7.43 (m, 2H, Ar—H), 7.28-7.33 (m, 2H, Ar—H), 4.40-4.46 (m, 1H, CH), 4.15-4.31 (m, 2H, CH$_2$), 3.67-3.73 (m, 2H, CH$_2$), 3.35-3.52 (m, 2H, CH$_2$), 3.18-3.30 (m, 2H, CH$_2$), 2.20-2.50 (m, 4H), 1.81-2.03 (m, 3H), 1.47-1.54 (m, 2H);
Ms (FAB+): m/z 409 (M+H$^+$).

(2) N-(4-O-DMTr-hydroxybutyl)-L-prolinamide (compound 15)

N-(4-hydroxybutyl)-N^α-Fmoc-L-prolineamide (compound 14) (7.80 g, 19.09 mmol) was mixed with anhydrous pyridine (5 mL), and the mixture was dried by azeotropic distillation at room temperature. To the obtained residue were added 4,4'-dimethoxytritylchloride (8.20 g, 24.20 mmol), DMAP (23 mg, 0.19 mmol) and anhydrous pyridine (39 mL). The mixture was stirred at room temperature for 1 hr, methanol (7.8 mL) was added, and the mixture was stirred at room temperature for 30 min. The mixture was diluted with dichloromethane (100 ml), washed with saturated aqueous sodium hydrogen carbonate (150 ml), and the organic layer was separated. The aforementioned organic layer was dried over sodium sulfate, and filtered. The solvent in the obtained filtrate was evaporated under reduced pressure. To the obtained unpurified residue were added anhydrous dimethylformamide (39 mL) and piperidine (18.7 mL, 189 mmol), and the mixture was stirred at room temperature for 1 hr. After completion of the reaction, the solvent in the aforementioned mixture was evaporated under reduced pressure at room temperature. The obtained residue was subjected to silica gel column chromatography (trade name Wakogel C-300, eluent CH$_2$Cl$_2$:CH$_3$OH=9:1, 0.05% pyridine-containing) to give compound 15 as a pale-yellow oil (9.11 g, yield 98%). The instrumental analytical values of the aforementioned compound 15 are shown below.

compound 15:
$^1$H-NMR (CDCl$_3$): δ7.39-7.43 (m, 2H, Ar—H), 7.30 (d, J=8.8 Hz, 4H, Ar—H), 7.21 (tt, 1H, 4.9, 1.3 Hz, Ar—H), 6.81 (d, J=8.8 Hz, 4H, Ar—H), 3.78 (s, 6H, OCH$_3$), 3.71 (dd, H, J=6.3 Hz, 5.4 Hz, CH), 3.21 (2H, 12.9, 6.3 Hz, 2H, CH$_2$), 3.05 (t, J=6.3 Hz, 2H, CH$_2$), 2.85-2.91 (m, 2H, CH$_2$), 2.08-2.17 (m, 1H, CH), 1.85-2.00 (m, 3H), 1.55-1.65 (m, 5H);
Ms (FAB+); m/z 489 (M+H$^+$), 303 (DMTr$^+$).

(3) N-(4-O-DMTr-hydroxybutyl)-N^α-(6-hydroxyhexanoyl)-L-prolinamide (compound 16)

An anhydrous dichloromethane solution (120 ml) of the obtained N-(4-O-DMTr-hydroxybutyl)-L-prolineamide (compound 15) (6.01 g, 12.28 mmol), EDC (2.83 g, 14.74 mmol), 1-hydroxybenzotriazole (3.98 g, 29.47 mmol) and triethylamine (4.47 g, 44.21 mmol) was mixed. To this mixture was further added 6-hydroxyhexane acid (1.95 g, 14.47 mmol) at room temperature under an argon atmosphere, and thereafter the mixture was stirred at room temperature for 1 hr under an argon atmosphere. The aforementioned mixture was diluted with dichloromethane (600 ml), and washed 3 times with saturated brine (800 ml). The organic layer was recovered, dried over sodium sulfate, and filtered. The solvent in the obtained filtrate was evaporated under reduced pressure, whereby the aforementioned compound 16 was obtained as pale-yellow bubbles (6.29 g, yield 85%). The instrumental analytical values of the aforementioned compound 16 are shown below.

compound 16:
$^1$H-NMR (CDCl$_3$): δ7.41-7.43 (m, 2H, Ar—H), 7.27-7.31 (m, 4H, Ar—H), 7.19-7.26 (m, 2H, Ar—H), 7.17-7.21 (m, 1H, Ar—H), 6.79-6.82 (m, 4H, Ar—H), 4.51-4.53 (m, 1H, CH), 3.79 (s, 6H$_2$OCH$_3$), 3.61 (t, 2H, J=6.4 Hz, CH$_2$), 3.50-3.55 (m, 1H, CH), 3.36-3.43 (m, 1H, CH), 3.15-3.24 (m, 2H, CH$_2$), 3.04 (t, J=6.3 Hz, 2H, CH$_2$), 2.38-2.45 (m, 1H, CH), 2.31 (t, 6.8 Hz, 2H, CH$_2$), 2.05-2.20 (m, 1H, CH), 1.92-2.00 (m, 1H, CH), 1.75-1.83 (m, 1H, CH), 1.48-1.71 (m, 8H), 1.35-1.44 (m, 2H, CH$_2$);
Ms (FAB+): m/z 602 (M$^+$), 303 (DMTr$^+$).

(4) N-(4-O-DMTr-hydroxybutyl)-N^α-(6-O-(2-cyanoethyl-N,N-diisopropylphosphityl)-hydroxyhexanoyl)-L-prolinamide (compound 17)

The obtained aforementioned N-(4-O-DMTr-hydroxybutyl)-N^α-(6-hydroxyhexanoyl)-L-prolineamide (compound 16) (8.55 g, 14.18 mmol) was mixed with anhydrous acetonitrile, and the mixture was dried by azeotropic distillation 3 times at room temperature. To the obtained residue was added diisopropylammoniumtetrazolide (2.91 g, 17.02 mmol), and the mixture was deaerated under reduced pressure and filled with argon gas. To the aforementioned mixture was added anhydrous acetonitrile (10 ml), and further, an anhydrous acetonitrile solution (7 mL) of 2-cyanoethoxy-N,N,N',N'-tetraisopropylphosphorodiamidite (5.13 g, 17.02 mmol) was added. The mixture was stirred at room temperature for 2 hr under an argon atmosphere, then diluted with dichloromethane, washed 3 times with saturated aqueous sodium hydrogen carbonate (200 ml), and washed with saturated brine (200 ml). The organic layer was recovered, dried over sodium sulfate, and filtered. The solvent in the obtained aforementioned filtrate was evaporated under reduced pressure. The obtained residue was subjected to column chromatography using amino silica gel as a filler (eluent hexane:ethyl acetate=1:3, 0.05% pyridine-containing) to give compound 17 as a colorless syrup (10.25 g, purity 92%, yield 83%). The instrumental analytical values of the aforementioned compound 17 are shown below.

compound 17:

$^1$H-NMR (CDCl$_2$): δ7.40-7.42 (m, 2H, Ar—H), 7.29-7.31 (m, 4H, Ar—H), 7.25-7.27 (m, 2H, Ar—H), 7.17-7.21 (m, 1H, Ar—H), 6.80-6.82 (m, 4H, Ar—H), 4.51-4.53 (m, 1H, CH), 3.75-3.93 (m, 4H), 3.79 (s, 6H$_2$OCH$_3$), 3.45-3.60 (m, 4H), 3.35-3.45 (m, 1H, CH), 3.20-3.29 (m, 1H, CH), 3.04 (t, J=6.4 Hz, 2H, CH$_2$), 2.62 (t, J=5.8 Hz, 2H, CH$_2$), 2.40-2.44 (m, 1H, CH), 2.31 (t, 7.8 Hz, 2H, CH$_2$), 2.03-2.19 (m, 1H, CH), 1.92-2.02 (m, 1H, CH), 1.70-1.83 (m, 1H, CH), 1.51-1.71 (m, 8H), 1.35-1.44 (m, 2H, CH$_2$), 1.18 (d, J=6.8 Hz, 6H, CH$_3$), 1.16 (d, J=6.8 Hz, 6H, CH$_3$);

$^{31}$P-NMR (CDCl$_3$): δ147.17;

Ms (FAB+): m/z 802 (M$^+$), 303 (DMTr$^+$), 201 (C$_8$H$_{19}$N$_2$OP$^+$)

Reference Example 4: Synthesis of lysine-cholesterolamidite

Compound 11 which is lysine-cholesterolamidite was produced according to the following scheme.

[Chem. 5]

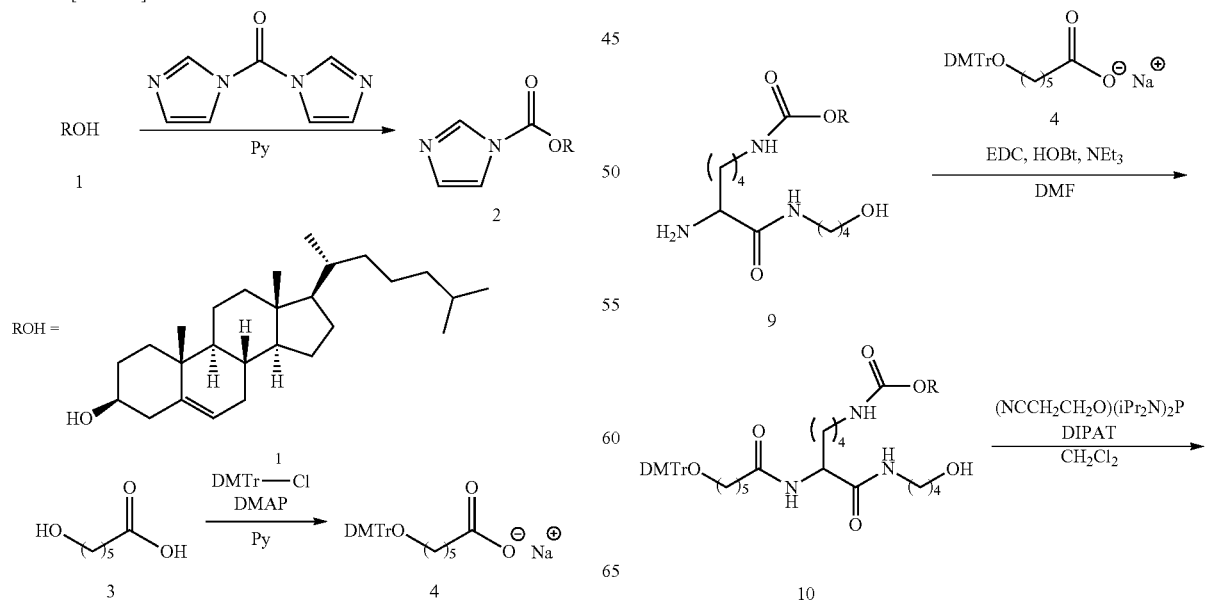

-continued

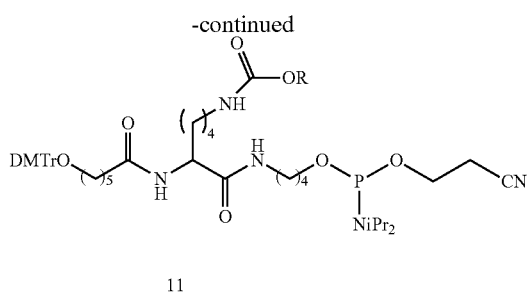

11

(1) Synthesis of (cholest-5-ene-3β-yl)imidazole-1-carboxylate (compound 2)

To a pyridine solution (200 mL) of cholesterol (compound 1) (8.0 g, 20 mmol) was added N,N-carbonyldiimidazole (6.6 g, 2.0 eq.), and the mixture was stirred at room temperature for 4 hr. The solvent evaporated by an evaporator, and the solution was diluted with dichloromethane. This solution was washed with 5% sodium dihydrogen phosphate aqueous solution, and then washed with saturated brine. The organic layer was dried over sodium sulfate, and the solvent was evaporated. The residue was dried under reduced pressure to give a white solid substance (9.8 g, yield 98%). The instrument analytical values of compound (2) are shown below.

$^1$H-NMR (500 MHz, CDCl$_3$) δ: 8.13 (s, 1H), 7.42 (s, 1H), 7.06 (s, 1H), 5.40-5.45 (m, 1H), 4.75-4.85 (m, 1H), 2.45-2.54 (m, 2H), 1.58-2.06 (m, 7H), 0.90-1.58 (m, 19H), 1.06 (s, 3H), 0.92 (d, 3H, J=6.3 Hz), 0.87 (d, 6H, J=6.8 Hz), 0.69 (s, 3H).

(2) Synthesis of 6-(4,4'-dimethoxytrityl)hexanoic acid (compound 4)

To a pyridine solution (75 mL) of 6-hydroxyhexanoic acid (compound 3) (3.0 g, 23 mmol) dried by azeotropic distillation and 4-dimethylaminopyridine (DMAP) (0.28 g, 0.1 eq.) was added 4,4-dimethoxytritylchloride (DMTrCl) (7.8 g, 1.0 eq.) and the mixture was stirred at room temperature for 5 hr. After confirmation of the disappearance of the starting material by TLC, methanol was added and the mixture was stirred for 30 min. The solvent was evaporated by an evaporator, and the solution was diluted with dichloromethane. This solution was washed with saturated aqueous sodium hydrogen carbonate solution, and washed with saturated brine. The organic layer was dried over sodium sulfate, and the solvent was evaporated. The mixture was triturated with hexane, and dried under reduced pressure to give an oil (7.8 g).

(3) Synthesis of t-butyl (1-((4-hydroxybutyl)amino)-1-oxo-6-(2,2,2-trifluoroacetamido)hexan-2-yl)carbamate (compound 6)

To an N,N-dimethylformamide solution (160 mL) of N-α-(t-butoxycarbonyl)-N-ε-trifluoroacetyl-L-lysine (compound 5) (8.0 g, 24 mmol) were added 4-amino-1-butanol (2.4 g, 1.2 eq.) and 1-hydroxybenzotriazolemonohydrate (HOBt) (8.6 g, 2.4 eq.) at 0° C. 1-Ethyl-3-(3-dimethylaminopropyl)carbodiimide hydrochloride (EDC) (5.4 g, 1.2 eq.) was added and the mixture was stirred at room temperature for 30 min. The mixture was stirred at room temperature overnight. The solvent was evaporated from the reaction solution by an evaporator. To the obtained residue was added dichloromethane, and the mixture was washed with a saturated aqueous sodium hydrogen carbonate solution and washed with saturated brine. The organic layer was dried over sodium sulfate, and the solvent was evaporated under reduced pressure. The residue was washed with hexane, and the precipitate was collected by filtration and dried under reduced pressure to give a solid substance (7.0 g, yield 73%). The instrument analytical values of compound (6) are shown below.

$^1$H-NMR (500 MHz, CDCl$_3$) δ: 7.16 (br, 1H), 6.77 (t, J=5.4 Hz, 1H), 4.04 (m, 1H), 3.66 (d, J=5.4 Hz, 2H), 3.37 (dd, J=12.9, 6.3 Hz, 2H), 3.29 (dd, J=12.4, 6.3 Hz, 2H), 1.84-1.79 (m, 2H), 1.66-1.56 (m, 6H), 1.44 (s, 9H), 1.41-1.37 (m, 2H).

(4) Synthesis of t-butyl(6-amino-1-((4-hydroxybutyl)amino)-1-oxohexan-2-yl)carbamate (compound 7)

To a methanol solution (30 mL) of compound 6 (3.0 g, 7.2 mmol) was added aqueous ammonia (26.5 mL, 50 eq.) and the mixture was stirred at room temperature for one day. Furthermore, aqueous ammonia (26.5 mL, 50 eq.) was added and the mixture was stirred at 40° C. for 7 hr. After completion of the reaction, the solvent was evaporated under reduced pressure. The residue was dried under reduced pressure to give an oil (2.3 g). The instrument analytical values of compound (7) are shown below.

ESI-MS: m/z 318.25 [M+H]$^+$

(5) Synthesis of t-butyl(cholest-5-ene-3β-yl) (6-((4-hydroxybutyl)amino)-6-oxohexane-1,5-diyl)dicarbamate (compound 8)

To a pyridine solution (100 mL) of compound 7 (2.3 g, 7.3 mmol) were added compound 2 (14 g, 4.0 eq.) and 4-dimethylaminopyridine (DMAP) (0.27 g, 0.3 eq.), and the mixture was stirred at 40° C. for 5 days. The solvent was evaporated by an evaporator, and the solution was diluted with dichloromethane. This solution was washed with saturated aqueous sodium hydrogen carbonate solution, and washed with saturated brine. The organic layer was dried over sodium sulfate, and the solvent was evaporated. The obtained residue was purified by silica gel column chromatography (eluent dichloromethane:methanol=20:1) to give a solid substance (3.5 g, yield 67%). The instrument analytical values of compound (8) are shown below.

$^1$H-NMR (500 MHz, CDCl$_3$) δ: 5.37 (s, 1H), 4.74 (m, 1H), 4.47 (m, 1H), 3.67 (m, 2H), 3.30 (m, 2H), 3.19-3.11 (m, 2H), 2.34 (d, 2H, J=6.3 Hz), 1.98 (m, 2H), 1.90-1.80 (m, 5H), 1.65-1.00 (m, 38H), 0.99 (s, 3H), 0.92 (d, 3H, J=6.3 Hz), 0.87 (d, 6H, J=6.8 Hz), 0.69 (s, 3H).

ESI-MS: m/z 730.59 [M+H]$^+$, 752.57 [M+Na]$^+$, 1460.19 [2 M+H]$^+$, 1482.16 [2 M+Na]$^+$

(6) Synthesis of cholest-5-ene-3β-yl (5-amino-6-((4-hydroxybutyl)amino)-6-oxohexyl)carbamate (compound 9)

Compound 8 (3.4 g, 4.7 mmol) was added to 2 M-hydrochloric acid/methanol solution (150 mL), and the mixture was stirred at room temperature for 3 hr. After completion of the reaction, the solvent was evaporated under reduced pressure. The residue was triturated with hexane and dried under reduced pressure to give a solid substance (2.7 g, yield 93%). The instrument analytical values of compound (9) are shown below.

ESI-MS: m/z 630.54 [M+H]$^+$, 1460.07 [2 M+H]$^+$ (7) Synthesis of cholest-5-ene-3β-yl (5-(6-(4,4'-dimethoxytrityl)hexaneamide)-6-((4-hydroxybutyl)amino)-6-oxohexyl)carbamate (compound 10)

To an N,N-dimethylformamide solution (90 mL) of compound 9 (2.5 g, 4.0 mmol) were added compound 4 (2.6 g, 1.5 eq.), 1-hydroxybenzotriazolemonohydrate (HOBt) (1.8 g, 3.0 eq.), and triethylamine (1.2 g, 3.0 eq.), and the mixture was stirred at 0° C. 1-Ethyl-3-(3-dimethylaminopropyl)carbodiimide hydrochloride (EDC) (1.1 g, 1.5 eq.) was added and the mixture was stirred for 30 min. Then the mixture was stirred at room temperature overnight. The solvent was evaporated from the reaction solution by an evaporator. To the obtained residue was added dichloromethane, and the mixture was washed with a saturated aqueous sodium hydrogen carbonate solution, and washed with saturated brine. The organic layer was dried over sodium sulfate, and the solvent was evaporated under reduced pressure. The obtained residue was purified by silica gel column chromatography (eluent ethyl acetate+0.05% pyridine→ethyl acetate:methanol (30:1)+0.05% pyridine) to give a solid substance (2.0 g, yield 50%). The instrument analytical values of compound (10) are shown below.

$^1$H-NMR (500 MHz, CDCl$_3$) δ: 7.42-7.41 (m, 2H), 7.32-7.26 (m, 6H), 7.21-7.18 (m, 1H), 6.81 (d, J=8.8 Hz, 4H), 5.37 (s, 1H), 4.79 (m, 1H), 4.32 (m, 1H), 3.78 (s, 6H), 3.64-3.61 (m, 2H), 3.29-3.25 (m, 2H), 3.18-3.09 (m, 2H), 3.02 (t, J=6.6 Hz, 2H), 2.35-2.26 (m, 2H), 2.19 (t, J=7.6 Hz, 2H), 2.06-1.58 (m, 9H), 1.58-0.90 (m, 33H), 0.99 (s, 3H), 0.92 (d, 3H, J=6.3 Hz), 0.87 (d, 6H, J=6.8 Hz), 0.69 (s, 3H).

ESI-MS: m/z 1068.72 [M+Na]$^+$, 1084.71 [M+K]$^+$ (8) Synthesis of cholest-5-ene-3β-yl (5-(6-(4,4'-dimethoxytrityl)hexaneamide)-6-((4-(((2-cyanoethoxy)(diisopropylamino)phosphino)oxy)butyl)amino)-6-oxohexyl)carbamate (compound 11)

To a dichloromethane solution (8 mL) of compound 10 (2.3 g, 2.2 mmol) dried by azeotropic distillation was added diisopropylammonium tetrazolide (DIPAT) (0.45 g, 1.2 eq.). A dichloromethane solution (2 mL) of 2-cyanoethoxy-N,N,N',N'-tetraisopropyl phosphorodiamidite (0.80 g, 1.2 eq.) was added, and the mixture was stirred at 40° C. for 3 hr. The mixture was diluted with dichloromethane and washed with saturated aqueous sodium hydrogen carbonate and saturated brine. The organic layer was dried over sodium sulfate, and the solvent was evaporated. The residue was subjected to column chromatography (eluent n-hexane:ethyl acetate (1:2)+0.1% triethylamine) using aminosilica to give a solid substance (2.2 g, yield 81%). The instrument analytical values of compound (11) are shown below.

$^1$H-NMR (500 MHz, CDCl$_3$) δ: 7.43-7.41 (m, 2H), 7.32-7.25 (m, 6H), 7.21-7.17 (m, 1H), 6.81 (d, J=8.8 Hz, 4H), 5.36 (s, 1H), 4.78 (m, 1H), 4.34 (m, 1H), 3.78 (s, 6H), 3.70-3.55 (m, 6H), 3.28-3.23 (m, 2H), 3.13-3.09 (m, 2H), 3.02 (t, J=6.6 Hz, 2H), 2.64 (t, J=6.5 Hz, 2H), 2.19 (t, J=7.6 Hz, 2H), 2.00-1.78 (m, 6H), 1.65-0.90 (m, 38H), 1.18-1.16 (m, 12H), 0.99 (s, 3H), 0.92 (d, 3H, J=6.3 Hz), 0.87 (d, 6H, J=6.8 Hz), 0.67 (s, 3H).

$^{31}$P-NMR (202 MHz, CDCl$_3$): β=148.074, 147.913

ESI-MS: m/z 1268.85 [M+Na]$^+$, 1284.82 [M+K]$^+$

Reference Example 5: Synthesis of Fatty Acid Active Ester Form

According to the following scheme 9, myristic acid-N-hydroxysuccinimide ester (C14-NHS), palmitic acid-N-hydroxysuccinimide ester (C16-NHS) or stearic acid-N-hydroxysuccinimide ester (C18-NHS) was each synthesized. In addition, according to the following scheme 10, oleic acid-N-hydroxysuccinimide ester (C18:1-NHS) was synthesized.

scheme 9

[Chem. S9]

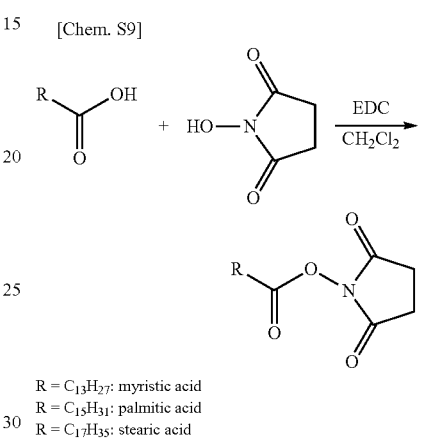

R = C$_{13}$H$_{27}$: myristic acid
R = C$_{15}$H$_{31}$: palmitic acid
R = C$_{17}$H$_{35}$: stearic acid scheme 10

[Chem. S10]

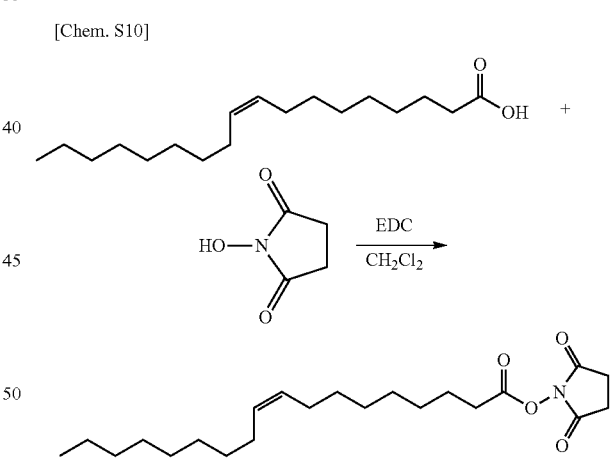

Synthesis of Myristic Acid-N-Hydroxysuccinimide Ester (C14-NHS)

Myristic acid (1.5 g, 6.6 mmol) was dissolved in dichloromethane (30 ml) and the mixture was stirred. To this solution were added N-hydroxysuccinimide (0.91 g, 1.2 eq.) and 1-ethyl-3-(3-dimethylaminopropyl)carbodiimide hydrochloride (EDC) (1.5 g, 1.2 eq.), and the mixture was stirred overnight. After washing twice with water, the mixture was washed once with saturated brine, dried over sodium sulfate, and the solvent was evaporated under reduced pressure. The obtained residue was purified by silica gel column chromatography (ethyl acetate/hexane=⅓) to give the object product (1.4 g, yield 67%). The NMR measurement results of the obtained myristic acid-N-hydroxysuccinimide ester (C14-NHS) are shown below.

myristic acid-N-hydroxysuccinimide ester
(C14-NHS)

$^1$H-NMR (CDCl$_3$) δ: 2.83 (4H, s), 2.60 (2H, t, J=7.6 Hz), 1.74 (2H, q, J=7.6 Hz), 1.44 (2H, q, J=6.9 Hz), 1.48-1.22 (18H, m), 0.88 (3H, t, J=6.8 Hz).

Synthesis of Palmitic Acid-N-Hydroxysuccinimide Ester (C16-NHS)

Palmitic acid (6.0 g, 23 mmol) was dissolved in dichloromethane (110 ml) and the mixture was stirred. To this solution were added N-hydroxysuccinimide (3.2 g, 1.2 eq.) and 1-ethyl-3-(3-dimethylaminopropyl)carbodiimide hydrochloride (EDC) (5.4 g, 1.2 eq.), and the mixture was stirred overnight. After washing twice with water, the mixture was washed once with saturated brine, dried over sodium sulfate, and the solvent was evaporated under reduced pressure. The obtained residue was purified by silica gel column chromatography (ethyl acetate/hexane=½) to give the object product (7.8 g, yield 94%). The NMR measurement results of the obtained palmitic acid-N-hydroxysuccinimide ester (C16-NHS) are shown below.

palmitic acid-N-hydroxysuccinimide ester
(C16-NHS)

$^1$H-NMR (CDCl$_3$) δ: 2.84 (4H, s), 2.60 (2H, t, J=7.6 Hz), 1.74 (2H, q, J=7.6 Hz), 1.38 (2H, q, J=6.9 Hz), 1.43-1.20 (m, 22H), 0.88 (3H, t, J=6.8 Hz).

Synthesis of Stearic Acid-N-Hydroxysuccinimide Ester (C18-NHS)

Stearic acid (3.0 g, 11 mmol) was dissolved in dichloromethane (100 ml) and the mixture was stirred. To this solution were added N-hydroxysuccinimide (1.5 g, 1.2 eq.) and 1-ethyl-3-(3-dimethylaminopropyl)carbodiimide hydrochloride (EDC) (2.4 g, 1.2 eq.), and the mixture was stirred for 2 days. After washing twice with water, the mixture was washed once with saturated brine, dried over sodium sulfate, and the solvent was evaporated under reduced pressure. The obtained residue was purified by silica gel column chromatography (ethyl acetate/hexane=⅓) to give the object product (2.8 g, yield 70%). The NMR measurement results of the obtained stearic acid-N-hydroxysuccinimide ester (C18-NHS) are shown below.

stearic acid-N-hydroxysuccinimide ester
(C18-NHS)

$^1$H-NMR (CDCl$_3$) δ: 2.84 (4H, m), 2.60 (2H, t, J=7.6 Hz), 1.74 (2H, q, J=7.6 Hz), 1.38 (2H, q, J=6.9 Hz), 1.43-1.20 (m, 26H), 0.88 (3H, t, J=6.8 Hz).

Synthesis of oleic acid-N-hydroxysuccinimide ester
(C18:1-NHS)

Oleic acid (4.0 g, 14 mmol) was dissolved in dichloromethane (70 ml) and the mixture was stirred. To this solution were added N-hydroxysuccinimide (2.0 g, 1.2 eq.) and 1-ethyl-3-(3-dimethylaminopropyl)carbodiimide hydrochloride (EDC) (3.3 g, 1.2 eq.), and the mixture was stirred overnight. After washing twice with water, the mixture was washed once with saturated brine, dried over sodium sulfate, and the solvent was evaporated under reduced pressure. The obtained residue was purified by silica gel column chromatography (ethyl acetate/hexane=⅓) to give the object product (5.2 g, yield 97%). The NMR measurement results of the obtained oleic acid-N-hydroxysuccinimide ester (C18:1-NHS) are shown below.

oleic acid-N-hydroxysuccinimide ester
(C18:1-NHS)

$^1$H-NMR (CDCl$_3$) δ: 5.35 (2H, m), 2.83 (4H, s), 2.60 (2H, t, J=7.6 Hz), 2.01 (4H, m), 1.75 (2H, q, J=7.6 Hz), 1.41-1.27 (20H, m), 0.88 (3H, t, J=6.8 Hz).

While the present invention has been described above with reference to illustrative embodiments, the present invention is by no means limited thereto. Various changes that may become apparent to those skilled in the art may be made in the configuration and specifics of the present invention without departing from the scope of the present invention.

INDUSTRIAL APPLICABILITY

The single-stranded nucleic acid molecule of the present invention can perform superior delivery to a target without essentially requiring, for example, a carrier for the delivery, and can realize efficient regulation of gene expression. Therefore, for example, the toxicity of the carrier does not need to be considered, and a study for setting various conditions relating to the formation of a complex of a nucleic acid molecule and a carrier can be obviated. Consequently, for example, the labor and cost in terms of production and use can be reduced.

This application is based on a patent application No. 2015-065770 filed in Japan (filing date: Mar. 27, 2015), the contents of which are incorporated in full herein.

The invention claimed is:

1. A single-stranded nucleic acid molecule for inhibiting expression of a target gene, which consists of a region (X), a linker region (Lx) and a region (Xc), wherein
said region (X) is complementary to said region (Xc),
at least one of said region (X) and said region (Xc) comprises an expression inhibitory sequence that inhibits expression of the target gene,
said linker region (Lx) comprises formula (I-4):

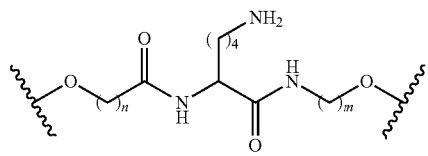

(I-4)

wherein n is an integer from 0 to 30, and m is an integer from 0 to 30,
a bio-related substance having a delivery function is bonded to formula (I-4) in said linker region (Lx) of the single-stranded nucleic acid molecule for inhibiting expression of a target gene,
said bio-related substance is a lipid,
said region (Xc) is perfectly complementary to the entire region or part of the said region (X),
said region (X) consists of any of the following residues (1) to (3): (1) an unmodified nucleotide residue(s), (2) a modified nucleotide residue(s), and (3) an unmodified nucleotide residue(s) and a modified nucleotide residue(s), and
the base number (X) of said region (X) and the base number (Xc) of said region (Xc) satisfy the formula: X-Xc=1 or 2.

2. The single-stranded nucleic acid molecule according to claim 1, wherein said lipid is a simple lipid, a complex lipid, a derived lipid, a single-chain lipid, a double-chain lipid, a glycolipid, a liposoluble vitamin or steroid.

3. The single-stranded nucleic acid molecule according to claim 1, wherein said lipid is at least one selected from the group consisting of palmitic acid, myristic acid, stearic acid, oleic acid, DOPE and cholesterol.

4. The single-stranded nucleic acid molecule according to claim 1, wherein said formula (I-4) is formula (I-4a):

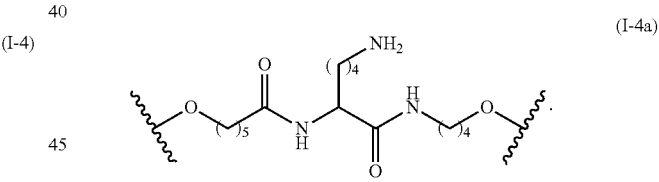

(I-4a)

5. The single-stranded nucleic acid molecule according to claim 1, wherein said linker region (Lx) comprises the following formula:

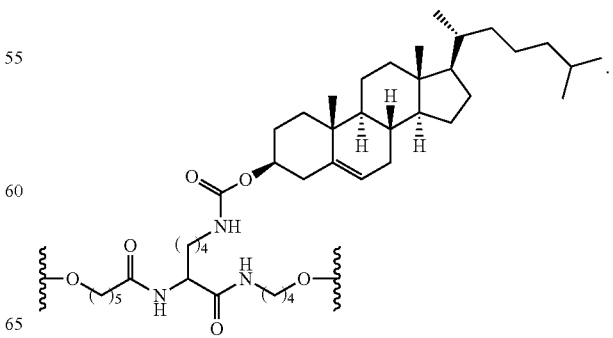

6. The single-stranded nucleic acid molecule according to claim 1, wherein the base number (Xc) of said region (Xc) is 19-30.

7. The single-stranded nucleic acid molecule according to claim 1, which is an RNA molecule.

8. The single-stranded nucleic acid molecule according to claim 1, wherein a total base number of said single-stranded nucleic acid molecule is not less than 38.

9. The single-stranded nucleic acid molecule according to claim 1, comprising at least one modified residue.

10. The single-stranded nucleic acid molecule according to claim 1, comprising a stable isotope.

11. The single-stranded nucleic acid molecule according to claim 1, wherein said expression inhibitory sequence is a mature miRNA sequence.

12. The single-stranded nucleic acid molecule according to claim 1, wherein said region (X) and said region (Xc) are respectively:
    (1) SEQ ID NO:29 and SEQ ID NO:37, or
    (2) SEQ ID NO:31 and SEQ ID NO:38.

13. A composition for inhibiting expression of a target gene, comprising the single-stranded nucleic acid molecule according to claim 1.

14. A pharmaceutical composition comprising the single-stranded nucleic acid molecule according to claim 1.

15. A method of inhibiting expression of a target gene, comprising a step of administering the single-stranded nucleic acid molecule according to claim 1 to a cell, tissue, or organ.

16. The method according to claim 15, wherein said single-stranded nucleic acid molecule is administered in vivo or in vitro.

17. The method according to claim 15, wherein the gene expression is inhibited by RNA interference.

18. A method of treating a disease, comprising a step of administering the single-stranded nucleic acid molecule claim 1 to a patient, wherein said single-stranded nucleic acid molecule comprises, as said expression inhibitory sequence, a sequence that inhibits expression of a gene causing said disease.

19. The method according to claim 18, wherein the single-stranded nucleic acid molecule is administered to a patient suffering from inflammatory diseases, and wherein the gene causing the disease is TGF-β1 gene.

20. The method according to claim 16, wherein the single-stranded nucleic acid molecule is administered to a subject suffering from inflammatory diseases in vivo, and wherein the target gene is TGF-β1 gene.

21. A nucleic acid molecule for use in the treatment of a disease, wherein said nucleic acid molecule is the single-stranded nucleic acid molecule according to claim 1, and said single-stranded nucleic acid molecule comprises, as said expression inhibitory sequence, a sequence that inhibits expression of a gene causing said disease.

22. The single-stranded nucleic acid molecule according to claim 1, wherein said lipid is bonded to $NH_2$ of formula (I-4) in said linker region (Lx) of the single-stranded nucleic acid molecule.

* * * * *

SEQUENCE LISTING

```
<160> NUMBER OF SEQ ID NOS: 39

<210> SEQ ID NO 1
<211> LENGTH: 9
<212> TYPE: PRT
<213> ORGANISM: Artificial Sequence
<220> FEATURE:
<223> OTHER INFORMATION: Synthetic polyarginine peptide

<400> SEQUENCE: 1
```

```
Arg Arg Arg Arg Arg Arg Arg Arg Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polyarginine peptide

<400> SEQUENCE: 2

Arg Arg Arg Arg Arg Arg Arg
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic penetratin

<400> SEQUENCE: 3

Arg Gln Ile Lys Ile Trp Phe Gly Asn Arg Arg Met Lys Trp Lys Lys
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic penetratin

<400> SEQUENCE: 4

Arg Arg Met Lys Trp Lys Lys
1               5

<210> SEQ ID NO 5
<211> LENGTH: 14
<212> TYPE: PRT
<213> ORGANISM: Artificial Sequence
<220> FEATURE:
<223> OTHER INFORMATION: Synthetic Tat fragment

<400> SEQUENCE: 5

Gly Arg Lys Lys Arg Arg Gln Arg Arg Arg Pro Pro Gln Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic Tat fragment

<400> SEQUENCE: 6

Tyr Gly Arg Lys Lys Arg Arg Gln Arg Arg Arg Pro Pro Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Tat fragment

<400> SEQUENCE: 7

Tyr Gly Arg Lys Lys Arg Arg Gln Arg Arg Arg
```

<210> SEQ ID NO 8
<211> LENGTH: 9
<212> TYPE: PRT
<213> ORGANISM: Artificial Sequence
<220> FEATURE:
<223> OTHER INFORMATION: Synthetic Tat fragment

<400> SEQUENCE: 8

Arg Lys Lys Arg Arg Gln Arg Arg Arg
1               5

<210> SEQ ID NO 9
<211> LENGTH: 26
<212> TYPE: PRT
<213> ORGANISM: Artificial Sequence
<220> FEATURE:
<223> OTHER INFORMATION: Synthetic transportan

<400> SEQUENCE: 9

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 10
<211> LENGTH: 21
<212> TYPE: PRT
<213> ORGANISM: Artificial Sequence
<220> FEATURE:
<223> OTHER INFORMATION: Synthetic transportan

<400> SEQUENCE: 10

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 11
<211> LENGTH: 18
<212> TYPE: PRT
<213> ORGANISM: Artificial Sequence
<220> FEATURE:
<223> OTHER INFORMATION: Synthetic amphiphilic model peptide

<400> SEQUENCE: 11

Lys Leu Ala Leu Lys Leu Ala Leu Lys Ala Leu Lys Ala Ala Leu Lys
1               5                   10                  15

Leu Ala

<210> SEQ ID NO 12
<211> LENGTH: 12
<212> TYPE: PRT
<213> ORGANISM: Artificial Sequence
<220> FEATURE:
<223> OTHER INFORMATION: Synthetic GE11

<400> SEQUENCE: 12

Tyr His Trp Tyr Gly Tyr Thr Pro Gln Asn Val Ile
1               5                   10

<210> SEQ ID NO 13
<211> LENGTH: 6
<212> TYPE: PRT

<213> ORGANISM: Artificial Sequence
<220> FEATURE:
<223> OTHER INFORMATION: Synthetic GE11(7)

<400> SEQUENCE: 13

Tyr His Trp Tyr Gly Tyr
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic GE11(5)

<400> SEQUENCE: 14

Tyr His Trp Tyr
1

<210> SEQ ID NO 15
<211> LENGTH: 18
<212> TYPE: PRT
<213> ORGANISM: Artificial Sequence
<220> FEATURE:
<223> OTHER INFORMATION: Synthetic PVEC

<400> SEQUENCE: 15

Leu Leu Ile Ile Leu Arg Arg Arg Ile Arg Lys Gln Ala His Ala His
1               5                   10                  15

Ser Lys

<210> SEQ ID NO 16
<211> LENGTH: 16
<212> TYPE: PRT
<213> ORGANISM: Artificial Sequence
<220> FEATURE:
<223> OTHER INFORMATION: Synthetic K-FGF

<400> SEQUENCE: 16

Ala Ala Val Ala Leu Leu Pro Ala Val Leu Leu Ala Leu Leu Ala Pro
1               5                   10                  15

<210> SEQ ID NO 17
<211> LENGTH: 10
<212> TYPE: PRT
<213> ORGANISM: Artificial Sequence
<220> FEATURE:
<223> OTHER INFORMATION: Synthetic Ku70

<400> SEQUENCE: 17

Val Pro Met Leu Lys Pro Met Leu Lys Glu
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Synthetic muscarinic receptor activating
      peptide

<400> SEQUENCE: 18

Tyr Thr Trp Tyr Thr Pro
1               5

<210> SEQ ID NO 19

-continued

```
<211> LENGTH: 6
<212> TYPE: PRT
<213> ORGANISM: Artificial Sequence
<220> FEATURE:
<223> OTHER INFORMATION: Synthetic muscarinic receptor activating
      peptide

<400> SEQUENCE: 19

Tyr Ser Trp Tyr Thr Pro
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic muscarinic receptor activating
      peptide

<400> SEQUENCE: 20

His Trp His Thr Pro
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic muscarinic receptor activating
      peptide

<400> SEQUENCE: 21

Tyr His Arg His Thr Pro
1               5

<210> SEQ ID NO 22
<211> LENGTH: 14
<212> TYPE: PRT
<213> ORGANISM: Artificial Sequence
<220> FEATURE:
<223> OTHER INFORMATION: Synthetic muscarinic receptor activating
      peptide

<400> SEQUENCE: 22

Asn Ala Tyr Thr Trp Tyr Thr Pro Glu Trp His Thr Pro Ala
1               5                   10

<210> SEQ ID NO 23
<211> LENGTH: 18
<212> TYPE: PRT
<213> ORGANISM: Artificial Sequence
<220> FEATURE:
<223> OTHER INFORMATION: Synthetic SAP

<400> SEQUENCE: 23

Val Arg Leu Pro Pro Pro Val Arg Leu Pro Pro Pro Val Arg Leu Pro
1               5                   10                  15

Pro Pro

<210> SEQ ID NO 24
<211> LENGTH: 6
<212> TYPE: PRT
<213> ORGANISM: Artificial Sequence
<220> FEATURE:
<223> OTHER INFORMATION: Synthetic MMP-1 inhibitor peptide

<400> SEQUENCE: 24
```

```
<210> SEQ ID NO 24 (continued)
```

Val Thr Tyr Gly Asn Pro
1               5

```
<210> SEQ ID NO 25
<211> LENGTH: 6
<212> TYPE: PRT
<213> ORGANISM: Artificial Sequence
<220> FEATURE:
<223> OTHER INFORMATION: Synthetic MMP-1 inhibitor peptide

<400> SEQUENCE: 25
```

Val Thr Val Gly Asn Pro
1               5

```
<210> SEQ ID NO 26
<211> LENGTH: 21
<212> TYPE: PRT
<213> ORGANISM: Artificial Sequence
<220> FEATURE:
<223> OTHER INFORMATION: Synthetic Pep-1

<400> SEQUENCE: 26
```

Lys Glu Thr Trp Trp Glu Thr Trp Trp Thr Glu Trp Ser Gln Pro Lys
1               5                   10                  15

Lys Lys Arg Lys Val
            20

```
<210> SEQ ID NO 27
<211> LENGTH: 15
<212> TYPE: PRT
<213> ORGANISM: Artificial Sequence
<220> FEATURE:
<223> OTHER INFORMATION: Synthetic Pep-7

<400> SEQUENCE: 27
```

Ser Asp Leu Trp Glu Met Met Met Val Ser Leu Ala Cys Gln Tyr
1               5                   10                  15

```
<210> SEQ ID NO 28
<211> LENGTH: 12
<212> TYPE: PRT
<213> ORGANISM: Artificial Sequence
<220> FEATURE:
<223> OTHER INFORMATION: Synthetic HN-1

<400> SEQUENCE: 28
```

Thr Ser Pro Leu Asn Ile His Asn Gly Gln Lys Leu
1               5                   10

```
<210> SEQ ID NO 29
<211> LENGTH: 25
<212> TYPE: RNA
<213> ORGANISM: Artificial Sequence
<220> FEATURE:
<223> OTHER INFORMATION: Synthetic single-stranded nucleic acid molecule

<400> SEQUENCE: 29
```
gguauaugcu guguguacuc ugcuu                                          25

```
<210> SEQ ID NO 30
<211> LENGTH: 55
<212> TYPE: RNA
<213> ORGANISM: Artificial Sequence
<220> FEATURE:
<223> OTHER INFORMATION: Synthetic single-stranded nucleic acid molecule

<400> SEQUENCE: 30
```
gcagaguaca cacagcauau accccacacc gguauaugcu guguguacuc ugcuu      55

<210> SEQ ID NO 31
<211> LENGTH: 25
<212> TYPE: RNA
<213> ORGANISM: Artificial Sequence
<220> FEATURE:
<223> OTHER INFORMATION: Synthetic single-stranded nucleic acid molecule

<400> SEQUENCE: 31
ggaaucgaag uacucagcgu aaguu                                      25

<210> SEQ ID NO 32
<211> LENGTH: 25
<212> TYPE: RNA
<213> ORGANISM: Artificial Sequence
<220> FEATURE:
<223> OTHER INFORMATION: Synthetic single-stranded nucleic acid molecule

<400> SEQUENCE: 32
ggaacuucgc gugucgaaua guauu                                      25

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
ttgtgcggca gtggttgagc cg                                         22

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
gaagcaggaa aggccggttc atgc                                       24

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35
gccacggctg cttccagctc ctc                                        23

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
aggtctttgc ggatgtccac gtcac                                      25

<210> SEQ ID NO 37
<211> LENGTH: 23
<212> TYPE: RNA

```
<213> ORGANISM: Artificial Sequence
<220> FEATURE:
<223> OTHER INFORMATION: Synthetic single-stranded nucleic acid molecule

<400> SEQUENCE: 37
gcagaguaca cacagcauau acc                                          23

<210> SEQ ID NO 38
<211> LENGTH: 23
<212> TYPE: RNA
<213> ORGANISM: Artificial Sequence
<220> FEATURE:
<223> OTHER INFORMATION: Synthetic single-stranded nucleic acid molecule

<400> SEQUENCE: 38
cuuacgcuga guacuucgau ucc                                          23

<210> SEQ ID NO 39
<211> LENGTH: 23
<212> TYPE: RNA
<213> ORGANISM: Artificial Sequence
<220> FEATURE:
<223> OTHER INFORMATION: Synthetic single-stranded nucleic acid molecule

<400> SEQUENCE: 39
uacuauucga cacgcgaagu ucc                                          23
```